(12) United States Patent
Parilov et al.

(10) Patent No.: US 7,949,480 B2
(45) Date of Patent: May 24, 2011

(54) METHOD FOR DETERMINING AN INTERACTION BETWEEN AN ELECTROMAGNETIC RADIATION AND A MATERIAL

(75) Inventors: Evgueni Parilov, Brooklyn, NY (US); Mary Potasek, Princeton, NJ (US)

(73) Assignee: Simphotek, Inc., Newark, NJ (US)

( * ) Notice: Subject to any disclaimer, the term of this patent is extended or adjusted under 35 U.S.C. 154(b) by 1159 days.

(21) Appl. No.: 11/559,093

(22) Filed: Nov. 13, 2006

(65) Prior Publication Data
US 2007/0290147 A1    Dec. 20, 2007

Related U.S. Application Data

(60) Provisional application No. 60/813,980, filed on Jun. 14, 2006.

(51) Int. Cl.
*G01B 5/30* (2006.01)
(52) U.S. Cl. ............. 702/40; 702/86; 702/179; 702/189
(58) Field of Classification Search .................... 702/40, 702/86, 179, 189; 73/576, 578; 34/245, 34/248, 259, 266, 275
See application file for complete search history.

(56) References Cited

U.S. PATENT DOCUMENTS

| 7,031,571 B2 * | 4/2006 | Mihailov et al. ................ 385/37 |
| 2003/0203502 A1 | 10/2003 | Zenhausern et al. |
| 2004/0142484 A1 | 7/2004 | Berlin et al. |
| 2005/0139484 A1 * | 6/2005 | Brooks et al. ................ 205/687 |

OTHER PUBLICATIONS

Ellen S. Marmur et al., "A Review of Laser and Photodynamic Therapy for the Treatment of Nonmelanoma Skin Cancer", America Society for Dermatological Surgery, Inc. 2004; 30 pp. 264-271.
M. Potasek et al., "All-Optical Power Limiting", Journal of Nonlinear Optical Physics & Materials, 2000, vol. 9, No. 3, pp. 343-364.
A. Kobyakov er al., "Analytical approach to dynamics of reverse saturable absorbers", Optical Society of America, Nov. 2000, vol. 17, No. 11, pp. 1884-1893.
C.W. Gardiner et al., "Driving atoms with light of arbitrary statistics", The American Physical Society, Aug. 1994, vol. 50, No. 2, pp. 1792-1808.
Paras N. Prasad, "Emerging Opportunities at the Interface of Photonics, Nanotechnology and Biotechnology", Mol. Cryst. Liq. Cryst. 2004 vol. 415, pp. 1-7.

(Continued)

*Primary Examiner* — Michael P Nghiem
*Assistant Examiner* — Elias Desta
(74) *Attorney, Agent, or Firm* — Ward & Olivo LLP

(57) ABSTRACT

The exemplary embodiments of the method, system, software arrangement and computer-accessible medium according to the present invention facilitates an analysis of interactions between nonlinear absorbing materials and an incident electromagnetic wave based on material properties and characteristics of the incident beam of the electromagnetic energy. Using the exemplary embodiments of the present invention, it is possible to determine laser beam propagation in a variety of multiphoton absorbing materials. Energy levels associated with such materials, which may be associated with various electron absorption and/or relaxation phenomena, may be added to and/or removed from the analysis. Incident laser beams can vary from continuous wave to attoseconds in duration and a numerical solution can be obtained that is radially and/or temporally dependent. Certain exemplary embodiments of the present invention can also be used to determine certain contributions of individual electronic energy levels within the materials to the total 15 absorption.

21 Claims, 25 Drawing Sheets

OTHER PUBLICATIONS

Richard L. Sutherland et al., "Excited-state characterization and effective three-photon absorption model of two-photon-induced excited-state absorption in organic push-pull charge-transfer chromophores", Optical Society of America, Sep. 2005, vol. 22, No. 9, pp. 1939-1948.

Chunfei Li et al., "Excited-state nonlinear absorption in multi-energy-level molecular systems", The American Physical Society, Jan. 1995, vol. 51, No. 1, pp. 569-575.

Haridas E. Pudavar et al., "High-density three-dimensional optical data storage in a stacked compact disk format with two-photon writing and single photon readout", American Institute of Physics, Mar. 1999 vol. 74, No. 9, pp. 1338-1340.

Bruce A. Reinhardt et al., "Highly Active Two-Phonton Dyes: Design, Synthesis, and Characterization toward Application", American Chemical Society 1998 vol. 10, No. 7, pp. 1863-1874.

Duo-Yuan Wang et al., "Large optical power limiting induced by three-photon absorption of two stilbazolium-like dyes", Chemical Physics Letters 2006, pp. 621-626.

Alberto Barchielli, "Measurement theory and stochastic differential equations in quantum mechanics", The American Physical Society, Sep. 1986 vol. 34, No. 3, pp. 1642-1649.

S. Hughes et al., "Modeling of picosecond-pulse propagation for optical limiting applications in the visible spectrum", Optical Society of America, Nov. 1997 vol. 14, No. 11, pp. 2925-2929.

I.C. Khoo et al., "Molecular photonics of a highly nonlinear organic fiber core liquid for picosecond-nanosecond optical limiting application", Chemical Physics 1999, pp. 517-531.

D. G. McLean et al., "Nonlinear absorption study of a $C_{60}$-toluene solution", Optics Letters Jun. 1993, vol. 18, No. 11, pp. 858-860.

Dmitriy I. Kovsh et al., "Nonlinear optical beam propagation for optical limiting", Applied Optics, Aug. 1999, vol. 38, No. 24, pp. 5168-5180.

Sean M. Kirkpatrick et al., "Nonlinear Saturation and Determination of the Two-Photon Absorption Cross Section of Green Fluorescent Protein" J. Phys. Chem. 2001, pp. 2867-2873.

Iam Choon Khoo et al., "Nonlinear-absorbing fiber array for large-dynamic-range optical limiting application against intense short laser pulses", Optical Society of America, Jun. 2004, vol. 21, No. 6, pp. 1234-1240.

Wenling Jia et al., "Optical limiting of semiconductor nanoparticles for nanosecond laser pulses" Applied Physics Letters, Dec. 2004, vol. 85, No. 26, pp. 6326-6328.

Iam-Choo Khoo et al., "Passive Optical Limiting of Picosecond-Nanosecond Laser Pulses Using Highly Nonlinear Organic Liquid Cored Fiber Array", IEEE Journal on Selected Topics in Quantum Electronics, Sep./Oct. 2001, vol. 7, No. 5, pp. 760-768.

George Witzgall et al., "Single-shot two-photon exposure of commercial photoresist for the production of three-dimensional structures" Optical Society of America, Nov. 1998 vol. 23, No. 22, pp. 1745-1747.

Nicole Allard, "The effect of neutral nonresonant collisions on atomic spectral lines" The American Physical Society, Oct. 1982 vol. 54, No. 4, pp. 1103-1182.

Shekhar Guha et al., "Third-order optical nonlinearities of metallotetrabenzoporphyrins and a platinum poly-yne", Optical Society of America, Feb. 1992 vol. 17, No. 4, pp. 264-266.

Ramanurthi Kannan et al., "Toward Highly Active Two-Photon Absorbing Liquids Syntheses and Characterization of 1,3,5-Triazine-Based Octupolar Molecules", American Chemical Society, 2004, pp. 185-194.

Shoji Maruo et al., "Two-Photon-Absorbed Near-Infrared Photopolymerization for Three-Dimensional Microfabrication", Journal of Microelectromechanical Systems, Dec. 1998 vol. 7, No. 4, pp. 411-415.

Joy E. Rogers et al., "Understanding the one-photon photophysical properties of a two-photon absorbing chromophore", Journal of American Physical Chemical Society, 2004, pp. 5514-5520.

Alexander Baev et al., "General theory for pulse propagation in two-photon active media", Journal of Chemical Physics, Oct. 2002, vol. 117, No. 13, pp. 6214-6220.

Brian H. Cumpston et al., "Two-photon polymerization initiators for three-dimensional optical data storage and microfabrication", Nature, Mar. 1999, vol. 398, pp. 51-54.

Guang S. He et al., "Degenerate two-photon-absorption spectral studies of highly two-photon active organic chromophores", American Institute of Physics, Mar. 2004 vol. 120, No. 11, pp. 5275-5284.

Lee W. Tutt et al., "A Review of Optical Limiting Mechanisms and Devices Using Organics, Fullerenes, Semiconductors and Other Materials", Prog. Quant. Electr. 1993 vol. 17, pp. 299-338.

W. Blau et al., "Reverse Saturable Absorption in Tetraphenylporphyrins", Optics Communications, Nov. 1985, vol. 56, No. 1.

Alexander Baev et al., "General Theory for Pulse Propagation in two-photon active media", Journal of Chemical Physics, Oct. 2002, vol. 117, No. 13.

Martin Klessinger et al., "Excited States and Photochemistry of Organic Molecules", Library of Congress Cataloging-in-Publication Data, pp. 20-33 and 243-307.

U. Siegner et al., "Nonlinear Optical Processes for Ultrashort Pulse Generation", Handbook of Optics vol. IV Fiber Optics and Nonlinear Optics, Second Edition, pp. 25.1-25.31.

International Search Report and Written Opinion mailed Sep. 8, 2008 for PCT/US07/71018.

* cited by examiner

METHOD FOR DETERMINING AN INTERACTION BETWEEN AN ELECTROMAGNETIC RADIATION AND A MATERIAL

CROSS-REFERENCE TO RELATED APPLICATION(S)

This application claims priority from U.S. Patent Application Ser. No. 60/813,980, filed Jun. 14, 2006, the entire disclosure of which is incorporated herein by reference.

STATEMENT REGARDING FEDERALLY SPONSORED RESEARCH

The present invention was developed, at least in part, using U.S. Government support under Grant No. FA9550-04-1-0219 awarded by the Air Force Office of Scientific Research. Therefore, the Federal Government may have certain rights in the invention.

FIELD OF THE INVENTION

The present invention relates to exemplary embodiments of a method, system and software arrangement which can determine interactions between an absorbing material and an incident coherent electromagnetic wave based on both material properties and characteristics of the incident beam of coherent electromagnetic energy. The absorbing material can be, e.g., a linear or nonlinear absorber and it may absorb one or more photons (e.g., $N_A \geq 1$). In particular, an exemplary procedure can be provided to determine laser beam propagation with a wide range of temporal durations in a variety of multiphoton absorbing materials. For example, incident laser beams can vary from continuous wave to attoseconds in duration, and a numerical solution can be obtained that is radially and/or temporary dependent. In addition, certain contributions of individual electronic energy levels within the materials to the total absorption can also be obtained using exemplary methods, systems and/or software arrangements in accordance with the present invention.

BACKGROUND INFORMATION

Previously there has been a significant increase in the development and use of materials that exhibit nonlinear multi-photon behavior. These materials may be used for such applications as, e.g., a high precision medical diagnostics tools usage, effective treatments for various cancers, biological detectors (e.g., markers), three-dimensional ("3D") micro- and/or nano-fabrication, fluorescent imaging systems, optical limiters, optical storage, semiconductor nano-sized probes, etc.

Conventional experiments that may be used to characterize the optical properties of nonlinear materials such as multi-photon organic/inorganic materials, semiconductors, fluids, gases or nanostructured materials include, e.g., z-scan procedures, optical transmission techniques, and pump-probe techniques. Facilities that are equipped to characterize such materials may require millions of dollars of equipment including, for example, lasers which can operate at different wavelengths in the ultraviolet, visible, near infrared ("IR"), mid IR and far IR regions. A laser beam can have an infinite duration (e.g., a continuous wave), or a finite duration which can be on the order of, e.g., nanoseconds ("ns"), picoseconds ("ps"), or femtoseconds ("fs"). Such facilities can also include various detectors, measurement electronics and data gathering computers that may be used to characterize these materials. A laser pulse duration or width can refer to, e.g., a continuous wave or a wave having a finite duration.

Pulse widths provided by the lasers which may be used to characterize and activate such optical materials can vary by about 12 orders of magnitude. This can make it difficult for a single numerical code to accurately and robustly characterize all possible interactions in order to reduce the need for costly experiments. Additionally, many experiments may need to be performed on a single material over many orders of magnitude of laser energies, where different electronic states of the nonlinear material can contribute to the total absorption behavior at different energy ranges. However, conventional codes may neglect higher energy levels. This simplification can yield reasonable results for particular energy ranges and incorrect results for other ranges.

Optical transmission measurements can be made using a particular laser such as, e.g., a Nd:YAG laser, a Ti:sapphire laser, a fiber laser, a semiconductor laser, a photonic crystal nanolaser, a quantum cascade laser, etc. The Nd:YAG laser can produce nanosecond pulses, whereas a Ti:sapphire laser can produce picosecond or femtosecond pulses. Each individual optical transmission measurement can be performed using a selected pulse width and a particular wavelength. However, a further measurement can be required for a different sample thickness. The number of experiments which may be required for characterizing these materials over a range of conditions and parameters can be large, and costs and time associated with such measurements can also be significant. For example, it may take many months to investigate a new material. Conventional simulation codes that can be used to model these measurements may be applicable only to a specific material interacting with a particular laser system at a certain intensity, and such codes may use simplifying assumptions that can further limit their applicability with respect to, e.g., wavelength, pulse widths, concentration of absorbing particles, and/or sample thickness. Such codes may not be capable of predicting the effects of variations in these parameters on the optical transmission behavior of a material based on one experimental measurement or a limited number of such measurements.

Conventional theoretical and/or numerical analyses of a laser beam transmission through nonlinear absorbing materials can utilize a number of assumptions that can limit their general applicability. Such nonlinear absorbing materials are described, e.g., in N. Allard et al., "The effect of neutral nonresonant collisions on atomic spectral lines," Rev. Mod. Phys. 54, 1103-1182 (1982). Shorter pulsed lasers and multi-photon processes are becoming important in this field as described, e.g., in U. Siegner et al., "Nonlinear optical processes for ultrashort pulse generation," in *Handbook of Optics*, M. Bass et al., eds., McGraw-Hill, New York, 2001, vol. IV, pp. 25-31. Thus, there may be a need for a more general approach which can increase the range of applicability of the equations used and the assumptions involved.

Conventional propagation and/or transmission analyses may neglect several molecular excited states as described, for example, in Y. R. Shen, *The Principle of Nonlinear Optics*, Wiley, New York, 1984. These excited states may be used to explain experimental data, particularly at high incident energy. Approximate theories of propagation and/or transmission through nonlinear materials have been formulated by various researchers in conjunction with their particular experimental data. These approximate theories may require numerical solutions, and approximate analytic expressions based on simplifying assumptions may often be used to reduce a required computational time. However, such approximate numerical solutions may not adequately describe the laser beam propagation through the material.

Additionally, because conventional approaches may often be used in conjugation with specific laser systems (e.g., with a specific wavelength and pulse duration), the resulting theoretical or numerical analysis may have a limited applicability. This approach can thus limit predictive capabilities of the analysis. For example, a theoretical description for a ns pulsed laser may not be capable of describing the effects of a ps or fs duration laser pulse interacting with the same material. Conventional theoretical or numerical analyses may provide agreement with specific experiments for specific materials and yield some insight, particularly in absorbers which may be described using single-photon processes. However, such conventional analyses may need to be modified and/or expanded to provide accurate descriptions and predictions of phenomena involving, e.g., a laser transmission through absorbers.

Changing the material or the laser beam characteristics associated with an absorption interaction may require a different numerical method and/or computer code to analyze the optical response. For example, new energy levels in the absorbing material may become accessible with an increase in laser intensity, and a new set of coupled equations may be required to describe the laser-absorber interaction. Because analytical solutions may not be possible, except in very simple cases, new computer codes may need to be written. An algorithm and/or code describing two energy levels of an absorber may not provide accurate results when three or more energy levels may contribute to a particular laser-absorber interaction. Defining new algorithms and writing new numerical codes to describe such absorption interactions can involve, e.g., months or years of effort.

Multi-photon-absorbing materials may also be used as nonlinear absorbers, including those described in, e.g., L. W. Tutt et al., "A review of optical limiting mechanisms and devices using organics, fullerenes, semiconductors and other materials," Prog. Quantum. Elect. 17, 299-305 (1993); J. E. Rogers et al., "Understanding the one-photon photophysical properties of a two-photon absorbing chromophore," J. Phys. Chem. A 108, 5514-5520 (2004); J. W. Perry, "Organic and metal-containing reverse saturable absorbers for optical limiters," in *Nonlinear Optics of Organic Molecules and Polymers*, H. S. Nalwa and S. Miyata, eds. (Boca Raton, Fla.: CRC 1997), pp. 813-839; M. J. Potasek et al., "All optical power limiting," J. Nonlinear Optical Physics and Materials 9, 343-365 (2000); M. J. Potasek, "High-Bandwidth Optical Networks and Communication, *Photodetectors and Fiber Optics* ed. H. S. Nalwa (Academic Press, 2001) pp. 459-543; D. I. Kovsh et al., "Nonlinear Optical Beam Propagation for Optical Limiting," Appl. Opt. 38, 5168-5180 (1999); and W. Jia et al., "Optical limiting of semiconductor nanoparticles for nanosecond laser pulses," Appl. Phys. Lett. 85, 6326-6328 (2004).

Photon absorbing materials may also be used in applications such as biological detectors as described in, e.g., S. M. Kirkpatrick et al., "Nonlinear saturation and determination of the two-photon absorption cross section of green fluorescent protein," J. Phys. Chem. B 105, 2867-2873 (2001), and three-dimensional microfabrication procedures such as those described in, for example, S. Maruo et al., "Two-photon-absorbed near-infrared photopolymerization for three-dimensional microfabrication," J. Microelectromechanical Systems 7, 411-415 (1998); B. H. Cumpston et al., "Two-photon polymerization initiators for three-dimensional optical data storage and microfabrication," Nature 398, 51-54 (1999); and G. Witzgall et al., "Single-shot two-photon exposure of commercial photoresist for the production of three-dimensional structures," Opt. Let. 23, 1745-1748 (1998).

Further applications of photon absorbing materials may include fluorescent imaging systems such as those described in W. Denk et al., "Two-photon laser scanning fluorescence microscopy," Science 248, 73-76 (1990), and optical storage systems as described, for example, in H. E. Pudavar et al., "High-density three-dimensional optical data storage in a stacked compact disk format with two-photon writing and single photon readout," Appl. Phys. Lett. 74, 1338-1340 (1999); and in P. N. Prasad, "Emerging opportunities at the interface of photonics, nanotechnology and biotechnology," Mol. Cryst. Liq. Cryst. 415, 1-10 (2004).

A nonlinear absorbing material in which an excited state absorption is large, as compared to a ground state absorption, can be referred to as a reversible saturable absorber ("RSA"). Such materials can exhibit a large absorption at high input laser energies, but their performance may be limited by an accompanying linear absorption at low input energy. A transparency (e.g., low absorption) at low input energy, combined with high absorption at high input energy, can be achieved with multi-photon absorber ("MPA") materials in which two or more photons may be absorbed simultaneously. For examples, the materials that exhibit a large two-photon absorption ("TPA") behavior may be important for a wide range of applications. Examples of TPA materials are described, for example, in M. Albota et al., "Design of organic molecules with large two-photon absorption cross sections," Science 281, 1653-1656 (1998); and B. A. Reinhardt et al., "Highly active two-photon dyes: Design, synthesis, and characterization toward application," Chem. Mater. 10, 1863-1874 (1998).

MPA materials can exhibit complex absorption mechanisms involving higher level electronic states. For example, TPA may be followed by excited state absorption ("ESA") which is described, e.g., in J. Kleinschmidt et al., "Measurement of strong nonlinear absorption in stilbene-chloroform solution, explained by the superposition of two-photon absorption and one-photon absorption from the excited state," Chem. Phys. Lett. 24, 133-135 (1974). Nonlinear transmission measurements and Z-scan measurements of organic materials can indicate the presence of ESA. These measurements are described, e.g., in D. A. Oulianov et al., "Observations on the measurements of two-photon absorption cross-section," Opt. Comm. 191, 235-243 (2001); and S. Guha et al., "Third-order optical nonlinearities of metallotetrabenzoporphyrins and a platinum poly-yne," Opt. Lett. 17, 264-266 (1992).

ESA can be the primary absorption mechanism in a nanosecond (ns) regime in a TPA material such as, e.g., D-π-A chromophore from the AFX group. TPA can be a primary mechanism for populating the excited states in such materials. However, TPA may dominate the total absorption behavior in the femtosecond regime. To analyze and predict the experimentally observable behavior of such materials under laser irradiation may require a solution to a nonlinear system of differential equations. Although some material systems can be described accurately by equations having a simple form which can be solved analytically, it may be important to have effective and robust numerical simulation tools to provide useful information for a wide variety of materials under a broad range of conditions.

For many RSA and TPA materials such as those described, e.g., in G. S. He et al., "Degenerate two-photon-absorption spectral studies of highly two-photon active organic chromophores," J. Chem. Phys. 120, 5275-5284 (2004); and R. Kannan et al., "Toward highly active two-photon absorbing liquids. Synthesis and characterization of 1,3,5-triazine-based octupolar molecules," Chem. Mater. 16, 185-194 (2004), simulation calculations can be based on a solution of a coupled system of propagation and rate equations. The rate equations may be formulated using a phenomenological five-level absorption model which is described, for example, in R. L. Sutherland et al., "Excited state characterization and effective three-photon absorption model of two-photon-induced excited state absorption in organic push-pull charge-transfer chromophores," J. Opt. Soc. Am. B 22, 1939-1948 (2005).

The propagated light in the RSA materials may attenuate as a result of electron excitations from the ground state and from singlet and/or triplet excited states. The absorption mechanism in the TPA materials can be similar to that in RSA materials, except that two photons can be absorbed during a transition from the ground state to the first singlet excited state. Depending on the pulse width and intensity of the incident light, the electron population densities may change which can alter the transmittance characteristics of the material. Solving equations describing light propagation in three-photon absorption ("3PA") materials such as, e.g., PPAI, which is described, e.g., in D.-Y. Wang et al., "Large optical power limiting induced by three-photon absorption of two stibazolium-like dyes," Chem. Phys. Lett. 369, 621-626 (2002), may be less problematic because the absorption model may include just two levels. In such materials, an incident pulse intensity may decrease due to simultaneous absorption of three photons from the ground level to the lowest singlet excited state. However, experimental investigations of 3PA materials are in an early stage and more complex nonlinear absorption models should be used for these materials.

Numerical methods may often be used to solve coupled equations describing laser-matter interactions, because there are few analytic solutions for such equations. New numerical code may be written to describe each energy level diagram representing a particular material of interest and an associated laser interaction. Such codes can vary in their degree of sophistication and in any approximations used, which may limit their applicability to certain lasers, as well as to particular temporal and/or radial domains. New numerical codes may be required to describe an increasing variety of possible interactions between lasers and materials. For example, a large number of individual computer codes have been written to solve various approximate sub-sets of laser-material interactions. As more lasers are developed having new wavelengths and/or pulse widths, many additional codes or modifications of existing codes may need to be written to describe them quantitatively.

Thus, there may be a need overcome the above-described deficiencies and issues to facilitate the effective and robust numerical simulation tools to measure, analyze, and predict the behavior of photon absorbing materials that are exposed to a laser irradiation. Further, there may be a need for a uniform solver which is capable of modeling a variety of nonlinear materials having different absorption configurations under a range of the irradiation conditions such as, e.g., different wavelengths, pulse widths, sample thicknesses, etc. Such exemplary simulation tools may provide guidelines for developing new functional materials, e.g., for designing molecular or semiconductor quantum dots or wires that may reduce development costs. The numerical method or computer program for such a simulation tool may not need to be rewritten when the material or laser conditions are changed.

SUMMARY OF THE INVENTION

One object of the present invention is to provide a system, method, software arrangement, and computer-accessible medium for determining and/or predicting interactions between generic photoactive materials and electromagnetic waves or electric fields such as, e.g., a laser pulse or a series of such pulses. The electromagnetic waves or electric fields may be coherent, and certain properties of such waves may be provided such as, e.g., pulse duration, intensity, wavelength, and intervals between successive pulses. The determinations can be based on one or more energy level diagrams associated with the material, which can also be provided in a form of an energy level string. The energy level diagrams and/or energy level strings can be expressed in terms of absorption blocks and/or relaxation blocks, and they may be used to formulate relationships such as, e.g., mathematical equations describing rates of energy level changes and propagation of the electromagnetic wave through the material. For example, equations describing propagation and/or absorption of the electromagnetic wave or electric field in the material can include, e.g., matrices and/or vectors which can be determined based on the energy level diagrams or energy level strings. Such energy level diagrams and/or strings may be modified as appropriate to provide determined results with an additional accuracy using corresponding modified rate and propagation equations.

In exemplary embodiments of the present invention, a numerical method, system and software arrangement are provided which are capable of describing interactions between photoactive "generic" materials (e.g., materials which can be characterized using absorption and/or relaxation blocks) and an electromagnetic wave or electric field. Such interactions can include, e.g., propagation phenomena such as diffraction, stimulated emission and/or cylindrically symmetric guided waves. For example, a variety of laser-generic material interactions can be described quantitatively using a common numerical code when changes are made to the energy level diagrams or energy level strings associated with the material, or to the properties of the laser such as, e.g., wavelength, pulse duration, radial beam diameter, etc.

Computational building blocks (e.g. absorption building blocks or relaxation building blocks) can provide terms to matrices and/or vectors which can be used to formulate rate and propagation equations. Mathematical equations describing energy level population dynamics can include a power series describing the intensity or electric field and one or more matrices. Such matrices can describe, e.g., relaxation rates, the intensity or electric field, and/or an $\alpha$-th power of the intensity or electric field. The propagation equation can include, for example, a series of terms having a form of vectors multiplied by an intensity of the electromagnetic wave or the electric field raised to an exponent $\beta$. Such vectors may contain absorption coefficients of the material of interest, where the coefficients can be related to the energy level diagram or energy level strings associated with the material.

In certain exemplary embodiments of the present invention, the propagation of a short-pulsed laser beam in a multi-level multi-photon absorbing material can be evaluated, where the propagation is determined to be in the presence of multi-photon absorption and/or one or more single photon excited state absorptions. Interactions may also be determined between the absorbing materials and laser pulses having a duration or pulse width which can range from nanoseconds to femtoseconds.

In further exemplary embodiments of the present invention, contributions of each electronic level to the total absorption within a material can be determined. This can provide insight into the roles of and relationships among the various energy levels that may be present in complex multi-photon absorbing materials. Absorption profiles and/or intensity distributions may also be determined with respect to both depth and radius in a material, which can provide a more accurate prediction of photon-induced effects in absorbing materials than conventional radially constant techniques used to predict pulse propagation within such materials.

In still further exemplary embodiments of the present invention, the effects of a diffraction on absorption and propagation of the laser pulse or other coherent wave in the absorbing material can also be determined. Effects of stimulated emission within the material can also be determined using certain exemplary embodiments of the present invention.

In yet further exemplary embodiments of the present invention, the propagation of the laser intensity or the electric field through a cylindrically symmetric guide or core structure, which can contain or be doped a generic photoactive material, may be described.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 3d is an exemplary graph of absolute contributions to absorption from different active electronic levels corresponding to the conditions provided in FIG. 3a;

FIG. 4d is an exemplary graph of the absolute contributions to the absorption from different active electronic levels corresponding to the conditions provided in FIG. 4a;

FIG. 8b is an exemplary graph of the contributions of active electron levels to the absorption, superimposed with a total intensity absorption, in the AF455 slab for the conditions provided in FIG. 8a;

Figure 1:
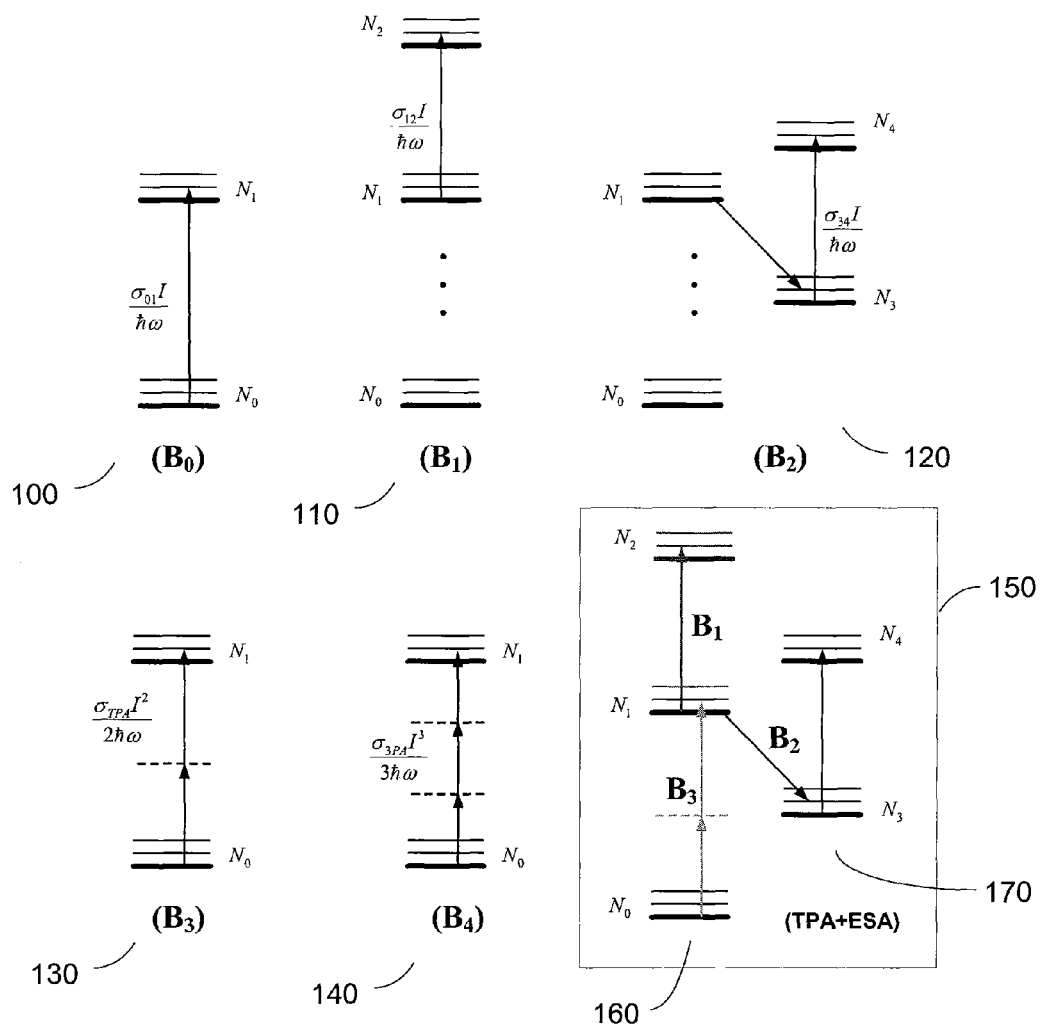
FIG. 1 shows five exemplary absorption diagrams, $B_0$-$B_4$, which can be used to describe an absorption configuration of generic materials, together with an energy level diagram that can be utilized to describe an absorption in a $C_{60}$-toluene solution.

Throughout the figures, the same reference numerals and characters, unless otherwise stated, are used to denote like features, elements, components or portions of the illustrated embodiments. Moreover, while the present invention will now be described in detail with reference to the figures, it is done so in connection with the illustrative embodiments.

DETAILED DESCRIPTION OF EXEMPLARY EMBODIMENTS

In certain exemplary embodiments of the method, system and software arrangement according to the present invention, certain measured parameters such as, for example, absorption cross sections and decay rates can be used. For example, certain exemplary procedures may be used for a numerical calculation of macroscopic rate equations where these parameters may not be easily derived either from microscopic quantum mechanical theories or from experimentally measured transmittance data. To provide a more comprehensive numerical method that can have a broad range of applicability with respect to both material characteristics and/or energy characteristics, basic computational building block diagrams may be used to describe properties of photoactive materials as described herein below.

An appropriate wave equation in the presence of an electric field can be provided by Maxwell's equation in scalar form, which may be written as:

$$\nabla^2 E_c(z, r, t) - \frac{1}{c_0^2} \frac{\partial^2}{\partial t^2} E_c(z, r, t) = \frac{1}{\varepsilon_0 c_0^2} \frac{\partial^2}{\partial t^2} P_c(z, r, t). \quad (1)$$

In this exemplary equation, it is assumed that $\nabla \cdot E_c = 0$, $\epsilon_0$ can refer to permittivity, and $c_0$ can represent the speed of light in vacuum. The electric field E and the induced nonlinear polarization P can be written as:

$$E_c(z,r,t) = \tilde{E}(z,r,t) \exp[-i(\omega_0 t - k_0 z)] + c.c.;$$

$$P_c(z,r,t) = \tilde{P}(z,r,t) \exp[-i(\omega_0 t - k_0 z)] + c.c., \quad (2)$$

where $\omega_0$ ($k_0$) is a frequency (e.g., wave number) of the incident electromagnetic wave, and $\tilde{E}(z,r,t)$ and $\tilde{P}(z,r,t)$ can represent real-valued slowly varying envelopes of the electric field and polarization vector, respectively. These exemplary equations can be simplified using a slowly varying envelope approximation ("SVEA"), where the pulse envelope may be assumed to vary slowly in time compared to an optical period. A paraxial approximation may also be used, where the envelope can be assumed to vary slowly along the propagation direction. The SVEA and the paraxial approximation are described, for example, in P. N. Butcher et al., *The Elements of Nonlinear Optics*, Cambridge University Press, Cambridge, UK, 1990.

Using these approximations, the scalar wave equation in Eq. (1) may be written as:

$$\left(\frac{\partial}{\partial z} + \frac{1}{c_0} \frac{\partial}{\partial t} - \frac{i}{2k_0} \nabla_\perp^2\right) \tilde{E}(z, r, t) = \frac{ik_0}{\varepsilon_0} \tilde{P}(z, r, t), \quad (3)$$

where $\nabla_\perp^2$, can represent an operator for the transverse variables. The intensity of the light can be defined by $\tilde{I}(z,r,t) = 2c_0 n \epsilon_0 |\tilde{E}(z,r,t)|^2$, where n is a linear index of refraction, and photon flux at a carrier frequency $\omega_0$ may be defined as $\tilde{\phi}(z,r,t) = \tilde{I}(z,r,t)/\hbar\omega_0$. The incident intensity of the laser pulse can be written as $\tilde{I}(z=0,r,t) = \tilde{I}_0 f(r,t)$, where f(r,t) may describe a radial and temporal shape of an incident pulse, or as $\tilde{I}(z=0, r) = \tilde{I}_0 f(r)$ to describe, for example, a pulse width of very long or infinite duration, e.g., a temporal continuous wave ("cw"). The term "pulse width" can refer to, for example, either a finite duration or a very long or infinite duration (e.g., a continuous wave). The term "laser pulse" can refer to, e.g., a pulse provided directly by a laser or a cw laser beam which may be pulsed by an external modulator. $\tilde{I}_0$ can represent a peak value of a pulse intensity, which may be expressed as $\tilde{I}_0 = 2c_0 n \epsilon_0 \tilde{E}_0^2$ with $\tilde{E}(z=0,r,t) = \tilde{E}_0 f(r,t)$ or $\tilde{E}(z=0,r) = \tilde{E}_0 f(r)$, where $\tilde{E}_0$ can represent a peak value of a corresponding electric field.

Temperature effects may be ignored in the exemplary procedure described herein in accordance with certain exemplary embodiments of the present invention, because they may not be significant in extremely short time scales (e.g., ns to fs) that can be characteristic of the absorption processes of interest. Significant thermal effects may be incorporated using techniques such as those described, e.g., in the Kovsh publication. Further, the effects of laser damage in absorbing materials, which can occur at very high intensities, may not be directly accounted for. Effects of optical elements such as, for example, lenses, apertures, beam splitters and/or mirrors which may be present in an optical path between the laser beam and the material may be incorporated in the propagating electromagnetic wave using techniques such as those described, e.g., in P. W. Milonni and J. H. Eberly, *Lasers*, New York, N.Y.: John Wiley, 1988, and in B. E. A. Saleh and M. C. Teich, *Fundamentals of Photonics*, New York, N.Y.: John Wiley, 1991.

In certain exemplary embodiments of the present invention, diffraction effects may be neglected. This approximation can provide accurate results, for example, if a sample thickness is limited to at most a few diffraction lengths. Also, diffraction was not observed in certain absorption experiments described herein. However, techniques which allow calculation of diffraction effects are also described herein below.

An absorbing medium may include two components: a chromophore and a solvent or polymer that can surround the chromophore. A polarization vector of the solvent/chromophore material may include a dispersion term and a Kerr nonlinearity, which can give rise to effects such as, for example, self-(de)focusing, self-steepening, and a Raman effect. For the materials that include a solvent and chromophore that are exposed to input intensities in the ranges described herein, these effects may not be significant, and can possibly be ignored. However, such effects can be incorporated into the exemplary techniques described herein using conventional procedures.

A polarization vector for the chromophore can be described by a density matrix. Such vector is described, e.g., in L. Allen et al., *Optical resonance and two-level atoms*, Plenum Press, New York, 1975; A. I. Maimistov et al., *Nonlinear Optical Waves*, Kluwer Academic Publishers, Dordrecht, The Netherlands 1999; and R. L. Sutherland, *Handbook of Nonlinear Optics*, Marcel Dekker, New York, 2003.

A Hamiltonian $\hat{H}$ of an absorbing system can be described by an unperturbed Hamiltonian $\hat{H}_0$ and an additional Hamiltonian term $\hat{H}_{int}$ (e.g., a perturbation term) such that $\hat{H}=\hat{H}_0+\hat{H}_{int}$. $\hat{H}_{int}$ can express an interaction between light and a molecular system using an electric-dipole approximation, e.g., $\hat{H}_{int}=-d_x E_x=-dE$, as described, for example, in Moloney et al., "Nonlinear Optics," Westview Press, Boulder, Colo., 2004. In such approximation, d can refer to an electric-dipole operator, which can further include an assumption that the laser is linearly polarized, and d and E may each be aligned along an x-axis.

Eigenvalue and Eigenenergy corresponding to an $s^{th}$ level may be written as $|s\rangle$ and $\epsilon_s$ respectively, as described, e.g., in C. W. Gardiner et al., "Input and output in damped quantum systems: Quantum stochastic differential equations and the master equation," Phys. Rev. A, 31, 3761-3774 (1985). Using these expressions, the wave function and unperturbed Hamiltonian can be written as $$|\psi\rangle = \sum_s a_s |s\rangle, \hat{H}_o |s\rangle = \epsilon_s |s\rangle,$$

respectively. A density matrix operator may be defined as $\hat{g}=|\psi\rangle\langle\psi|$, and a corresponding equation of motion can be written as $$\frac{\partial \hat{g}}{\partial t} = \frac{-i}{\hbar}[\hat{H}, \hat{g}], \text{ or } \frac{\partial g_{s_1 s_2}}{\partial t} = \frac{-i}{\hbar}\sum_{s_3}(H_{s_1 s_3} g_{s_3 s_2} - g_{s_2 s_3} H_{s_3 s_1}), \quad (4)$$

where matrix elements $g_{s_1 s_2}$ can represent a polarization induced by a transition between energy levels $s_1$ and $s_2$.

Photons from incident light can be absorbed by the molecular system, which may enable the atoms and/or molecules to occupy excited energy states (e.g., electronic, vibrational, and/or rotational). Thus, the polarization for $n_a$ atoms or molecules per unit volume, can be expressed as:

$$\vec{P} = n_a \hat{e} \cdot \int \psi\psi^* \vec{R} d\vec{R} = n_a \sum_{s_1 s_2} g_{s_1 s_2} d_{s_2 s_1} = n_a Tr(dg), \quad (5)$$

where $\hat{e}$ can represent a unit electric charge, and R can describe a distance between separated charges in a dipole moment approximation. After the excitation to higher energy states, the system may relax to a ground state through radiative and/or nonradiative transitions. In a semi-classical approach, the relaxation terms can be added to the equations of motion of the density matrix using a phenomenological technique. In general, quantum mechanical determinations of the relaxation terms may be quite involved as described, e.g., in C. W. Gardiner et al., "Driving atoms with light of arbitrary statistics," Phys. Rev. A, 50, 1792-1806 (1994); M. Lax, "Quantum noise IV. Quantum theory of noise sources," Phys. Rev. 145, 110-129 (1966); and A. Barchielli, "Measurement Theory and stochastic differential equations in quantum mechanics," Phys. Rev. A 34, 1642-1649 (1986).

For further understanding of the behavior of an ensemble of radiators (e.g., atoms, molecules, excitons, or impurities in a crystal) in a field of resonant or nonresonant coherent electromagnetic waves, it can be beneficial to characterize time scales of the various processes. The interaction of the radiators with non-resonant atoms (e.g., those present in a solvent) can give rise to a dephasing rate $\gamma_{s_1 s_2}$, which can be described by the expression:

$$\frac{\partial g_{s_1 s_2}}{\partial t} = -(\gamma_{s_1 s_2} + i\omega_{s_1 s_2})g_{s_1 s_2} + \frac{-i}{\hbar}\sum_{s_3}(H_{s_1 s_3}^{int} g_{s_3 s_2} - g_{s_2 s_3} H_{s_3 s_1}^{int}). \quad (6)$$

Rate equations for an exemplary absorbing material such as $C_{60}$ can be determined based on Eq. (4) above. Equations of motion for density-matrix elements can be written as:

$$\frac{\partial g_{s_1 s_2}}{\partial t} = -(\Gamma_{s_1 s_2} + i\omega_{s_1 s_2})g_{s_1 s_2} + \frac{i\tilde{E}}{\hbar}\sum_{s_3}(d_{s_1 s_3} g_{s_3 s_2} - g_{s_2 s_3} d_{s_3 s_1}), \quad (7)$$

where d can be taken along the direction of $\tilde{E}$, $\Gamma_{s_1 s_2}$ can represent a transverse relaxation time arising from various non-radiative behaviors such as, e.g., irreversible losses and elastic scattering, and $\omega_{s_1 s_2}=\omega_{s_1}-\omega_{s_2}$ and $\omega=\omega_0$. The decay rate for the off-diagonal terms can be expressed as $|\Gamma_{s_1 s_2} g_{s_1 s_2}|>>|\partial g_{s_1 s_2}/\partial t + i\omega_{s_1 s_2} g_{s_1 s_2}|$ for $s_1 \neq s_2$. It may be preferable to denote an absorption cross section from state $|s_1\rangle$ to state $|s_2\rangle$ as:

$$\sigma_{s_1 s_2} = \frac{\omega \Gamma_{s_1 s_2} |d_{s_1 s_2}|^2}{\hbar n c \varepsilon_0 [\Gamma_{s_1 s_2}^2 + (\omega_{s_1 s_2} - \omega)^2]}. \quad (8)$$

An approximation that $\omega_{s_1 s_2}=\omega_0$ can also be used. The equations of motion for the density-matrix elements can be written as:

$$\frac{\partial g_{00}}{\partial t} = \sigma_{01}\tilde{\phi}(g_{11} - g_{00}) + k_{10}g_{11} + k_{30}g_{33} \quad (9)$$

-continued $$\frac{\partial g_{11}}{\partial t} = \sigma_{12}\tilde{\phi}(g_{22}-g_{11}) - \sigma_{01}\tilde{\phi}(g_{11}-g_{00}) + k_{21}g_{22} - (k_{13}+k_{10}g_{11})$$

$$\frac{\partial g_{22}}{\partial t} = -\sigma_{12}\tilde{\phi}(g_{22}-g_{11}) - k_{21}g_{22}$$

$$\frac{\partial g_{33}}{\partial t} = \sigma_{34}\tilde{\phi}(g_{44}-g_{33}) + k_{43}g_{44} - k_{30}g_{33}$$

$$\frac{\partial g_{44}}{\partial t} = -\sigma_{34}\tilde{\phi}(g_{44}-g_{33}) - k_{43}g_{44}$$

where $k_{s_1 s_2}$ can represent longitudinal relaxation times and $\tilde{\phi}(z,r,t)=\tilde{I}(z,r,t)/\hbar\omega_0$. Decay of the vibrational states may be very fast (e.g., on the order of femtoseconds), whereby stimulated emission may be negligible and the term $\sigma_{s_1 s_2}(g_{s_1 s_1}-g_{s_2 s_2})$ can be approximated as $-\sigma_{s_1 s_2} g_{s_2 s_2}$. An approximation $g_{s_2 s_2}=\tilde{N}_{s_2}$ may also be used. The rate equations can thus be written in a form of:

$$\frac{\partial \tilde{N}_0}{\partial t} = -\sigma_{01}\tilde{\phi}\tilde{N}_0 + k_{10}\tilde{N}_1 + k_{30}\tilde{N}_3 \quad (10)$$

$$\frac{\partial \tilde{N}_1}{\partial t} = -\sigma_{01}\tilde{\phi}\tilde{N}_0 - (\sigma_{12}\tilde{\phi}+k_{13}+k_{10})\tilde{N}_1 + k_{21}\tilde{N}_2$$

$$\frac{\partial \tilde{N}_2}{\partial t} = \sigma_{12}\tilde{\phi}\tilde{N}_1 - k_{21}\tilde{N}_2$$

$$\frac{\partial \tilde{N}_3}{\partial t} = -(\sigma_{34}\tilde{\phi}+k_{30})\tilde{N}_3 + k_{43}\tilde{N}_4$$

$$\frac{\partial \tilde{N}_4}{\partial t} = \sigma_{34}\tilde{\phi}\tilde{N}_3 - k_{43}\tilde{N}_4$$

The polarization can be described by the equation:

$$\tilde{P}(z,r,t) = \quad (11)$$
$$-\frac{inc_0 \varepsilon_0}{\omega_0}\bigl(\sigma_{10}\tilde{N}_1(z,r,t) + \sigma_{12}\tilde{N}_2(z,r,t) + \sigma_{34}\tilde{N}_3(z,r,t)\bigr)\tilde{I}(z,r,t).$$

Combining Eq. (11) with Maxwell's equation, Eq. (1), can provide a corresponding propagation equation which may be written as:

$$\left(\frac{\partial}{\partial z} + \frac{1}{c}\frac{\partial}{\partial t}\right)\tilde{I}(z,r,t) = \quad (12)$$
$$-\bigl(\sigma_{10}\tilde{N}_0(z,r,t) + \sigma_{12}\tilde{N}_1(z,r,t) + \sigma_{34}\tilde{N}_3(z,r,t)\bigr)\tilde{I}(z,r,t),$$

where $c=c_0/n$. This equation may be used to describe propagation of light in a $C_{60}$ solution.

Stimulated Emission

Equations similar to Eq. (10) above can be derived that include effects of stimulated emission. In general, stimulated emission may occur from only one of the electronic levels, and spontaneous emission can occur from other electronic levels. Thus, the expressions provided in Eq. (10) can describe one exemplary behavior that may occur, e.g., stimulated emission, and both stimulated and spontaneous emission can occur in certain materials. The exemplary equations that include a description of stimulated emission may be written as:

$$\frac{\partial \tilde{N}_0}{\partial t} = \sigma_{01}\tilde{\phi}(\tilde{N}_1-\tilde{N}_0) + k_{10}\tilde{N}_1 + k_{30}\tilde{N}_3 \quad (13)$$

$$\frac{\partial \tilde{N}_1}{\partial t} =$$
$$-\sigma_{01}\tilde{\phi}(\tilde{N}_1-\tilde{N}_0) + \sigma_{12}\tilde{\phi}(\tilde{N}_2-\tilde{N}_1) + (k_{13}+k_{10})\tilde{N}_1 + k_{21}\tilde{N}_2$$

$$\frac{\partial \tilde{N}_2}{\partial t} = -\sigma_{12}\tilde{\phi}(\tilde{N}_2-\tilde{N}_1) - k_{21}\tilde{N}_2$$

$$\frac{\partial \tilde{N}_3}{\partial t} = \sigma_{34}\tilde{\phi}(\tilde{N}_4-\tilde{N}_3) + k_{43}\tilde{N}_4 - k_{30}\tilde{N}_3$$

$$\frac{\partial \tilde{N}_4}{\partial t} = -\sigma_{34}\tilde{\phi}(\tilde{N}_4-\tilde{N}_3) - k_{43}\tilde{N}_4$$

A corresponding propagation equation that includes the effects of stimulated emission can be written as $$\left(\frac{\partial}{\partial z} + \frac{1}{c}\frac{\partial}{\partial t}\right)\tilde{I}(z,r,t) = \quad (14)$$
$$\bigl(\sigma_{01}[\tilde{N}_1(z,r,t)-\tilde{N}_0(z,r,t)] + \sigma_{12}[\tilde{N}_2(z,r,t)-\tilde{N}_1(z,r,t)] +$$
$$\sigma_{34}[\tilde{N}_4(z,r,t)-\tilde{N}_3(z,r,t)]\bigr)\tilde{I}(z,r,t)$$

As described herein, the relaxation time of the vibrational states of the electronic levels can be assumed to be very fast (e.g., on the order of femtoseconds), so that effects of stimulated emission may be neglected in such systems. The appropriate dephasing rate can be determined for a specific material of interest. For organic molecules that can be provided in solvents, a dephasing time $\gamma_{s_1 s_2}^{-1}$ can be between approximately 7 and 70 fs. The dephasing time can be selected as an upper limit for a laser pulse width $T_0$, such that, approximately, $T_0 > \gamma_{s_1 s_2}^{-1}$. A lifetime of the lowest excited electronic state $\gamma_{ss}^{-1}$ can be approximately 1 ns as described, e.g., in J. Turro, *Modern Molecular Photochemistry*, Benjamin, N.Y., 1978. Thus, a laser pulse width can be selected to be approximately within the range $\gamma_{s_1 s_1}^{-1} > T_0 > \gamma_{s_1 s_2}^{-1}$.

Absorption Energy Diagrams

An analysis using the density matrix approach, which may be guided by a phenomenological Jablonski diagram for a single photon excitation, is described herein below. A similar analysis applicable to RSA materials including, e.g., copper phthalocyanine, $C_{60}$, and cadmium texaphyrin is described in C. Li et al., "Excited-state nonlinear absorption in multi-energy-level molecular systems," Phys. Rev. A, 51, 569-575 (1995). Utilization of a density matrix approach to investigate a pulse width dependence of the TPA cross-sections of PRL-101 measured in the ns and fs regions is described, e.g., in A. Baev et al., "General theory for pulse propagation in two-photon active media," J. Chem. Phys. 117, 6214-6220 (2002).

Organic molecules may exhibit multiphoton absorption involving both singlet and triplet states with increasing laser intensities. This behavior can be difficult to describe based solely on quantum calculations. Therefore, a phenomenological model based on spectroscopic and kinetic data can be provided that includes a description of nonlinear absorbers which further includes state diagrams or Jablonski diagrams, and is described, e.g., in M. Klessinger et al., *Excited States and Photochemistry of Organic Molecules*, VCH, Deerfield Beach, Fla. 1995. This type of an exemplary model can provide a representation of population dynamics, which can generate corresponding rate equations. Experimental data used in this exemplary procedure can includes an absorption cross section and decay rates of various electronic levels.

Exemplary procedures in accordance with exemplary embodiments of the present invention described herein can provide a description of the absorption behavior of a variety of nonlinear materials using e.g., a single generalized numerical method. Several types of absorption mechanisms may be present within certain nonlinear materials, and the mechanisms can depend on the number of photons absorbed simultaneously and/or on the states in which absorption occurs. The exemplary embodiments of the methods, system, software arrangement and computer accessible medium according to the present invention can be used to describe, e.g., N-photon absorbers with both singlet and triplet levels.

Five exemplary types of absorption mechanisms can be used to model absorption behavior. These mechanisms 100-140 are shown in FIG. 1 as transition diagrams and labeled ($B_0$)-($B_4$). Electronic states in FIG. 1 are labeled $N_0$-$N_4$, and absorption cross-sections can be labeled with a σ identifier. As shown in FIG. 1, upward arrows may represent photoexcitation transitions, and downward arrows may represent intersystem electron decay events. In accordance with appropriate exemplary selection rules, single-photon absorption can occur along singlet-singlet transitions from a ground state 100 and/or a lowest excited state 110. Single-photon absorption can also occur along a triplet-triplet transition 120 from a lowest triplet excited state, which may be populated by electrons relaxed along an intersystem crossing link. These exemplary mechanisms do not explicitly consider ultrafast relaxations that may occur from vibronic intermediate states.

TPA can occur from the ground state by simultaneous absorption of two photons, which may promote electrons to the lowest excited singlet state. Such transition 130 as shown in FIG. 1 can be followed by two further transitions: a singlet-singlet transition 110, or a singlet-triplet transition 120 from $N_1$ to $N_3$. Three-photon absorption (3PA) may involve a promotion of ground state electrons to the lowest excited singlet state by simultaneous absorption of three photons, as shown in the transition diagram 140 of FIG. 1.

Transition diagrams 100-140 of FIG. 1 can represent computational "building blocks" that may be combined to describing general absorption behavior of nonlinear absorbing materials. For example, the absorption in a $C_{60}$-toluene solution—a nonlinear RSA material—can be described using a five-level model as described, e.g., in D. G. McLean et al., "Nonlinear absorption study of a C60-toluene solution," Opt. Lett. 18, 858-860 (1993). This exemplary model can be obtained by combining the absorption diagrams 100-120 as shown in FIG. 1 (e.g., $B_0 \cup B_1 \cup B_2$).

A five-level absorption model of a chromophore from an AFX group exhibiting TPA-assisted excited state absorption is described, e.g., in the He et al. and Kannon et. al. publications. This exemplary model, which includes TPA and ESA. can also be obtained, for example, by combining the absorption diagrams 110-130 shown in FIG. 1 (e.g., $B_1 \cup B_2 \cup B_3$).

The term "generic" material can refer to a nonlinear absorbing material having an absorption energy diagram that may be described by a combination of one or more basic transition diagrams such as, e.g., $B_0$-$B_4$ 100-140 shown in FIG. 1.

Rate and Propagation Equations

An absorption energy diagram obtainable as a combination of transition diagrams can specify the corresponding rate and propagation equations. For example, in accordance with the exemplary derivation described herein, a rate equation in a moving time frame (e.g., (z,t=t'−$k_1$z)) for a generic nonlinear material can be expressed in matrix form as:

$$\frac{d\tilde{N}(z,r,t)}{dt} = \left[\hat{D}_0 + \sum_{\alpha=1}^{N_A} \frac{\hat{D}_\alpha}{\alpha\hbar\omega_0}\tilde{I}^\alpha(z,r,t)\right]\tilde{N}(z,r,t), \quad (15)$$

where $\tilde{N}=[\tilde{N}_0,\tilde{N}_1,\ldots,\tilde{N}_S]^T$ can represent a population density vector function $\tilde{N}(z,r,t)$ for a system with S electronic levels, $\hat{D}_0 \equiv \hat{D}_0(\{k_{s_1 s_2}\})$, $\hat{D}_1 \equiv \hat{D}_1(\{\sigma_{s_1 s_2}\})$, $\hat{D}_2 \equiv \hat{D}_2(\sigma_{TPA})$, $\hat{D}_3 \equiv \hat{D}_3(\sigma_{3PA})$, ..., $\hat{D}_{N_A} \equiv \hat{D}_{N_A}(\sigma_{[N_A]PA})$ can be $N_A+1$ constant S×S sparse matrices having decay rates $k_{s_1 s_2}$, single photon $\sigma_{s_1 s_2}$, two-photon $\sigma_{TPA}$, three-photon $\sigma_{3PA}$, and, possibly, $N_A$-photon $\sigma_{[N_A]PA}$ molar cross-sections respectively, and $\tilde{I}(z,r,t)$ can be a function of a photon flux density. The propagation equation for such material may be expressed in a vector form as:

$$\frac{d\tilde{I}(z,r,t)}{dz} = -\sum_{\beta=1}^{N_B}(\sigma_\beta \cdot \tilde{N}(z,r,t))\tilde{I}^\beta(z,r,t) - \tilde{c}\tilde{I}(z,r,t), \quad (16)$$

where $\sigma_1 \equiv \sigma_1(\{\sigma_{s_1 s_2}\})$, $\sigma_2 \equiv \sigma_2(\sigma_{TPA})$, $\sigma_3 \equiv \sigma_3(\sigma_{3PA})$, ..., $\sigma_{N_B} \equiv \sigma_{N_B}(\sigma_{[N_B]PA})$ can be $N_B$ constant (mostly sparse) S-dimensional vectors which may include certain elements of corresponding $\hat{D}_\beta$ matrices, and $\tilde{c}$ can represent a linear absorption coefficient. The constant vectors and matrices in the above equations are described herein below in more detail.

Certain solutions to the coupled system of Eqs. (15) and (16) can be formulated using various mathematical and numerical techniques. For example, a numerical solution of the propagation equation using steady-state estimates of population densities is described, e.g., in D. G. McLean et al., "Nonlinear absorption study of a C60-toluene solution," Opt. Lett. 18, 858-860 (1993). An analytic solution of a three-level approximation for the five-level population density system of RSA $C_{60}$ is described, e.g., in A. Kobyakov et al., "Analytical approach to dynamics of reverse saturable absorbers," J. Opt. Soc. Am. B. 17, 1884-1894 (2000).

Analytic solutions may been formulated in the ns regime for TPA AF455 as described, e.g., in the Sutherland et al. publication and in the ps regime for TPA $L_{34}$ and for 3PA PPAI dye as described, e.g., in the Wang et al. publication. A Runge-Kutta numerical solution may also be used such as that described, e.g., in I.-C. Khoo et al., "Passive optical limiting of picosecond-nanosecond laser pulses using highly nonlinear organic liquid cored fiber array," IEEE J. Sel. Top. Quantum Electron. 7, 760-768 (2001). A beam-propagation technique used to model RSA CAP dye in toluene and TPA ZnSe is described, e.g., in S. Hughes et al., "Modeling of picosecond-pulse propagation for optical limiting applications in the visible spectrum," J. Opt. Soc. Am. B. 11, 2925-2929 (1997). Other exemplary solution procedures that may be used can include, for example, spectral and Crank-Nicholson finite difference methods which can included an instantaneous Kerr effect, diffraction, thermal effects for RSA SiNc, and Z-scan of a 2PA. An analytic approximation of these exemplary equations capable of accounting for the effects of long pulses and a numerical solution of an integro-differential equation for short pulses to model general TPA+singlet-singlet ESA organic absorbers can be used as described, e.g., in the Baev et al. publication.

Exemplary analytical solutions to the coupled system of Eqs. (15) and (16) can use stringent assumptions about photophysical properties of the materials and/or the range of temporal pulse durations. For example, the assumptions that may be used to account for photophysical properties can include: (a) a "negligible ground-state depopulation approximation," which assumes that the population density of the ground state is approximately constant; (b) the excited states of the singlet and triplet states are proportional to $I^2(t)$, which can correspond to a quasi-steady-state regime where the time dependence of the population densities approximates that of the intensity; (c) electronic states $N_2$ and $N_4$ may be neglected or electronic state $N_2$ may be neglected; (d) repopulation of the ground state due to the lowest triplet state relaxation may be ignored; and (e) singlet-triplet intersystem crossing and spatial diffusion may be ignored.

Laser Pulses

An incident electromagnetic wave (e.g., a laser pulse) interacting with a nonlinear absorbing material can be characterized using a variety of parameters which may specify certain properties of the wave. For example, such parameters can include coherency (or lack thereof), frequency (e.g., a single frequency or a set of discrete frequencies), a pulse, or a series of consecutive pulses (e.g., a "pulse train"), etc. A single pulse can be further characterized, e.g., by a temporal pulse width and/or a radial width. Multiple pulses or a pulse train can be further characterized, e.g., by a pulse duration, a separation time between pulses, a number of pulses or overall duration of a pulse train and/or an incident intensity or energy of each pulse.

Parameters which may be used to characterize or describe a laser pulse or other incident electromagnetic wave can be obtained using various procedures. For example, such parameters can be based on experimental measurements or manufacturer's specifications. A frequency may be modified using nonlinear optical techniques. A temporal pulse width may be modified using further nonlinear optical techniques such as, e.g., solutions and/or transform-limited nonlinear pulse compression techniques. The pulses may be created using a continuous wave laser by applying an external modulator such as, e.g., an electro-optic modulator. Also, a radial beam waist may be modified, e.g., by using a lens, an aperture and/or a nonlinear optical material which may be self-focusing.

An incident electromagnetic wave that includes multiple pulses and/or a pulse train can be characterized by a temporal pulse separation and/or a repetition rate. The pulses in such fields can be created or modified, e.g., by using intra-(laser) cavity procedures such as, e.g., mode-locking, Q-switching, or Q-switched mode-locking. External (laser) cavity procedures may also be used such as, e.g., an electro-optic modulator. Exemplary optical procedures such as, e.g., beam splitting, time delay, and/or recombination may also be used.

Certain limitations on a pulse duration (e.g., a ns pulse duration, a ps pulse duration, a sub-range of ns pulse duration, or a range of up to a few ns) can be assumed or estimated to obtain certain solutions to these equations. Certain conventional solution procedures may include a radial variable, although frequently it is assumed that the spatially-dependent functions are constant in the radial domain. Further, these conventional procedures may have been developed to describe the behavior of particular materials and/or for certain pulse temporal widths.

Solution Techniques

In accordance with certain exemplary embodiments of the present invention, a time-resolved radially-dependent finite-difference numerical scheme can be provided which may be used to describe absorption and/or relaxation behavior of any generic material interacting with an incident pulse over a broad range of temporal pulse widths (e.g., pulse durations).

The coupled exemplary system described by Eqs. (15) and (16) can be converted to a dimensionless form using the following transformations $\eta=z/L_{df}$, $\rho=r/R_0$, $\tau=t/T_0$, $I(\eta,\rho,\tau)=\tilde{I}(\eta,\rho,\tau)/\tilde{I}_0$, $N_\beta(\eta,\rho,\tau)=\tilde{N}_\beta(\eta,\rho,\tau)/N$, $L_{df}=\pi R_0^2 n_1/\lambda$, where $T_0$, $R_0$ are a pulse width and a beam radius, respectively, associated with the incident pulse shape. N can represent a total population electron density of the material, which may be independent of time, e.g., $$N = \sum_\beta \tilde{N}_\beta(\eta, \rho, \tau).$$

The incident pulse can be described by a general formula, $I(\eta=0,\rho,\tau)=\tilde{I}_0 f(\rho,\tau)$ or $I(\eta=0,\rho)=\tilde{I}_0 f(\rho)$ for cw. In additional exemplary embodiments of the present invention, described in more detail herein below, a standard Gaussian distribution may be used to describe the form of the incident pulse.

Using the transformations provided above, Eqs. (15) and (16) may be rewritten as:

$$\frac{dN(\eta, \rho, \tau)}{d\tau} = T_0\left[\hat{D}_0 + \sum_{\alpha=1}^{N_A} \frac{\hat{D}_\alpha I_0^\alpha}{\alpha \hbar \omega_0} I^\alpha(\eta, \rho, \tau)\right] N(\eta, \rho, \tau), \quad (17)$$

$$\frac{dI(\eta, \rho, \tau)}{d\eta} = \quad (18)$$

$$-L_{df} N \sum_{\beta=1}^{N_B} (\sigma_\beta \cdot N(\eta, \rho, \tau)) I_0^{(\beta-1)} I^\beta(\eta, \rho, \tau) - L_{df} \tilde{c} I(z, r, t),$$

respectively. The mathematical analysis that can be performed to describe the absorption and relaxation behavior of generic materials can be based on a solution of Eqs. (17) and (18).

For example, a family of identical 2D grids $\Omega$, which may be indexed by a radius $\rho$, can be defined such that:

$$\Omega = \{\Omega(\rho_j), \rho_j = j\Delta\rho\}, \quad (19)$$

$$\Omega(\rho_j) = (\Omega_N(j), \Omega_I(j)). \quad (20)$$

For every $\rho_j$ sample, a member from $\Omega$ can correspond to a pair of interleaved grids in the $\eta$–$\tau$ parametric domain. One such grid can be represented as $$\Omega_N(j) = \{(\eta_{n+1/2}, \rho_j, \tau_{i+1/2}), \eta_{n+1/2} = (\eta_0 + \Delta\eta/2) + n\Delta\eta, \tau_{i+1/2} = (\tau_0 + \Delta\tau/2) + i\Delta\tau\}, \quad (21)$$

and may be used to sample the population density $N(\eta,\rho,\tau)$. Another such grid, which can be represented as:

$$\Omega_I(j) = \{(\eta_n, \rho_j, \tau_i), \eta_n = \eta_0 + n\Delta\eta, \tau_i = \tau_0 + i\Delta\tau\},$$

$$\text{or } \Omega_E(j) = \{(\eta_n, \rho_j, \tau_i), \eta_n = \eta_0 + n\Delta\eta, \tau_i = \tau_0 + i\Delta\tau\} \quad (22)$$

may be used to sample the intensity $I(\eta,\rho,\tau)$ or the electric field $E(\eta,\rho,\tau)$.

The exemplary dimensionless equations provided in Eqs. (17) and (18) can be integrated as described herein below, using small step sizes $\Delta\tau$, $\Delta\eta$ at $\Omega_N(j)$, $\Omega_I(j)$ grid points, respectively. For example, the system of rate equations can be integrated to yield a spatially-resolved solution in a current moving frame (e.g., a reference system of the "pulse rest"), while the average intensity, $$\frac{1}{2}[I(\eta_n, \rho_j, \tau_i) + I(\eta_{n+1}, \rho_j, \tau_i)],$$

is held constant. Further, the propagation equation may be solved over a thin slice $[\eta,\eta+\Delta\eta]$, by using an available average population density, $$\frac{1}{2}[N(\eta_{n+1/2}, \rho_j, \tau_{i-1/2}) + N(\eta_{n+1/2}, \rho_j, \tau_{i+1/2})],$$

as an approximation to electronic populations.

An exemplary procedure to integrate the exemplary coupled system of rate and propagation equations provided in Eqs. (17) and (18) can be based on the following mathematical derivation. For example, the following expression can be derived from Eq. (17) as follows:

$$\frac{\partial \ln N(\eta, \rho, \tau)}{\partial \tau} = T_0 \left[ \hat{D}_0 + \sum_{\alpha=1...N_A} \frac{\hat{D}_\alpha I_0^\alpha}{\alpha \hbar \omega_0} I^\alpha(\eta, \rho, \tau) \right] \quad (23)$$

$\Delta\tau$ step can be applied to this equation, which leads to the following expression:

$$N(\eta, \rho, \tau + \Delta\tau) = N(\eta, \rho, \tau) \times \exp\left( \int_\tau^{\tau+\Delta\tau} T_0 \left[ \hat{D}_0 + \sum_{\alpha=1...N_A} \right. \right. \quad (24)$$

$$\left. \left. \frac{\hat{D}_\alpha I_0^\alpha}{\alpha \hbar \omega_0} I^\alpha(\eta, \rho, \tau') \right] d\tau' \right)$$

$$\approx N(\eta, \rho, \tau) \exp\left( \Delta\tau T_0 \hat{D}_0 + \Delta\tau T_0 \sum_{\alpha=1...N_A} \right. \quad (25)$$

$$\left. \frac{\hat{D}_\alpha I_0^\alpha}{\alpha \hbar \omega_0} I^\alpha(\eta, \rho, \tau) \times \frac{1}{2} \{ I^\alpha(\eta - \Delta\eta/2, \rho, \tau + \Delta\tau/2) + I^\alpha(\eta + \Delta\eta/2, \rho, \tau + \Delta\tau/2) \} \right).$$

Calculation of a propagation equation can be performed using Eq. (18), which can be rearranged to obtain the following expression:

$$\frac{\partial \ln I(\eta, \rho, \tau)}{\partial \eta} = -L_{df} N \sum_{\beta=1}^{N_B} (\sigma_\beta \cdot \tilde{N}(\eta, \rho, \tau)) I_0^{(\beta-1)} I^{\beta-1}(\eta, \rho, \tau) - L_{df} \tilde{c} \quad (26)$$

$\Delta\tau$ step can be applied to this equation, which leads to the following expression:

$$I(\eta + \Delta\eta, \rho, \tau) = I(\eta, \rho, \tau) \times \exp\left( -L_{df} N \sum_{\beta=1}^{N_B} \right. \quad (27)$$

$$\left\{ \sigma_\beta \cdot \int_\eta^{\eta+\Delta\eta} I_0^{(\beta-1)} I^{\beta-1}(\eta', \rho, \tau) \right\} \times$$

$$N(\eta', \rho, \tau) d\eta' \right\} \times$$

$$\exp\left( -L_{df} \int_\eta^{\eta+\Delta\eta} \tilde{c} d\eta' \right)$$

$$\approx I(\eta, \rho, \tau) \exp(-L_{df} N \Delta\eta \times \quad (28)$$

$$\sum_{\beta=1}^{N_B} \left\{ \left[ \sigma_\beta \cdot \frac{N(\eta + \Delta\eta/2, \rho, \tau - \Delta\tau/2) + N(\eta + \Delta\eta/2, \rho, \tau + \Delta\tau/2)}{2} \right] \times \right.$$

-continued $$\times \frac{I_0^{\beta-1}}{2} \left[ \begin{array}{c} I^{\beta-1}(\eta, \rho, \tau) + \\ I^{\beta-1}(\eta + \Delta\eta, \rho, \tau) \end{array} \right] \right\} - L_{df} \Delta\eta \tilde{c} \right).$$

Equations (25) and (28) may be used when performing a calculation of the coupled Eqs. (17) and (18).

The resulting system of coupled equations can be written as $$N_{n+1/2,j,i+1/2}^{(k)} \approx \quad (29)$$

$$\exp\left( \Delta\tau T_0 \hat{D}_0 + \Delta\tau T_0 \frac{\hat{D}_1 I_0}{\hbar\omega_0} \frac{1}{2} \{ I_{n,j,i} + I_{n+1,j,i}^{(k)} \} + \Delta\tau T_0 \frac{\hat{D}_2 I_0^2}{2\hbar\omega_0} \frac{1}{2} \right.$$

$$\left. \{ I_{n,j,i}^2 + I_{n+1,j,i}^{(k)2} \} + \Delta\tau T_0 \frac{\hat{D}_3 I_0^3}{3\hbar\omega_0} \frac{1}{2} \{ I_{n,j,i}^3 + I_{n+1,j,i}^{(k)3} \} \right) N_{n+1/2,j,i-1/2}^{(k)}$$

$$I_{n+1,j,i}^{(k+1)} \approx \quad (30)$$

$$\exp\left( -L_{df} N \Delta\eta \left\{ \sigma_1 \cdot \frac{N_{n+1/2,j,i-1/2}^{(k)} + N_{n+1/2,j,i+1/2}^{(k)}}{2} \right\} - L_{df} N \Delta\eta I_0 \right.$$

$$\left\{ \sigma_2 \cdot \frac{N_{n+1/2,j,i-1/2}^{(k)} + N_{n+1/2,j,i+1/2}^{(k)}}{2} \right\} \frac{1}{2} \{ I_{n,j,i} + I_{n+1,j,i}^{(k)} \} -$$

$$L_{df} N \Delta\eta I_0^2 \left\{ \sigma_3 \cdot \frac{N_{n+1/2,j,i-1/2}^{(k)} + N_{n+1/2,j,i+1/2}^{(k)}}{2} \right\}$$

$$\left. \frac{1}{2} \{ I_{n,j,i}^2 + I_{n+1,j,i}^{(k)2} \} - L_{df} \Delta\eta \tilde{c} \right) I_{n,i}$$

These exemplary equations may still contain an interdependence between the intensity and population densities. Therefore, k=1:K iterations can be performed to obtain a numerical solution of the intensity function $I(\eta_n, \rho, \tau)$ at a given depth $\eta_n$. To simplify notation, only the indices n, j, and i are retained in the further description below.

At any depth $\eta_n$ the iterating scheme provided by Eqs. (29) and (30) may converge very fast using a second-order Taylor series expansion of the matrix exponential in Eq. (29). By selecting a sufficiently small $\Delta\tau$, sufficient convergence can be achieved with a number of iterations k, possibly equal to 2 or 3. If the pulse is short in the temporal domain, the grid size may be increased significantly to ensure that eigenvalues of the matrix in the exponent are less than one, which can allow the use of such a Taylor expansion.

An alternate exemplary procedure that may be used is to sub-sample the grid on demand, e.g., only at the high intensity areas, which may be relatively small compared to the entire parametric domain. For example, at every time step $\tau_{i-1/2} \to \tau_{i+1/2}$ in Eq. (29), the magnitude of the matrix elements in the exponent can be evaluated. If necessary, M−1 additional time sub-samples can be introduced such as, e.g., $\tau_{i-1/2} \equiv \tau^0 \to \tau^1 \to \ldots \tau^{M-1} \to \tau_{i+1/2} \equiv \tau^M$, where M can be selected such that the elements of the resulting refined matrices corresponding to the sub-samples are small enough to ensure the validity of the Taylor series approximation of the matrix exponentials. To calculate the refined matrices for each $\tau^m$, the integration step used to derive Eq. (29) herein can be repeated, using an integration domain of $[\tau^m, \tau^{m+1}]$. To perform this integration, the average intensity values can also be estimated at $\hat{\tau}^m = \tau^m + \frac{1}{2}\Delta\tau'$ samples, where $\Delta\tau' = \tau^{m+1} - \tau^m \equiv \Delta\tau/M$ can represent the resulting sub-sampling time procedure. Because any such sample $\hat{\tau}^m$ can be approximately equal to $\tau_{i-1/2} + (m+\frac{1}{2})\Delta\tau'$, $I_{n,j}(\hat{\tau}^m) \equiv I(\eta_n, \rho_j, \hat{\tau}^m)$ can be estimated using a linear interpolation of $I_{n,j}(\tau_{i-1/2})$ and $I_{n,j}(\tau_{i+1/2})$ which can be expressed as:

$$I_{n,j}(\hat{\tau}^m) = I_{n,j}(\tau_{i-1/2} + (m+1/2)\Delta\tau') \qquad (31)$$

$$= \lambda_m I_{n,j}(\tau_{i-1/2}) + \mu_m I_{n,j}(\tau_{i+1/2}),$$

where $\lambda_m + \mu_m = 1$, and $\lambda_m = (1-(m+\frac{1}{2})/M)$. The powers of the intensity values $I_{n,j}^\alpha$, $\alpha=1\ldots 3$, for the midpoint time grid samples $\tau_{i-1/2}, \tau_{i+1/2}$ in Eq. (31) can be interpolated using the expression $$I_{n,j}^\alpha(\tau_{i-1/2}) \approx (I^\alpha)_{n,j,\bar{i}} \equiv \frac{1}{2}(I_{n,j,i-1}^\alpha + I_{n,j,i}^\alpha). \qquad (32)$$

The numerical integration of the system of rate equations provided herein may be performed using additional sub-sampling times. For a notational simplicity, the following parameter substitutions can be used in Eq. (24):

$$D_0 = \Delta\tau T_0 \hat{D}_0, \; D_\alpha = \Delta\tau T_0 \hat{D}_\alpha I_0^\alpha / \alpha\hbar\omega_0, \text{ for } \alpha > 0. \qquad (33)$$

Using Eq. (33), Eq. (24) can be expressed as:

$$N(\eta, \rho, \tau + \Delta\tau) = \qquad (34)$$

$$N(\eta, \rho, \tau) \times \exp\left(\frac{1}{\Delta\tau}\int_\tau^{\tau+\Delta\tau} D_0 + \sum_{\alpha=1\ldots N_\Delta} D_\alpha I^\alpha(\eta, \rho, \tau')d\tau'\right)$$

Figure 9:
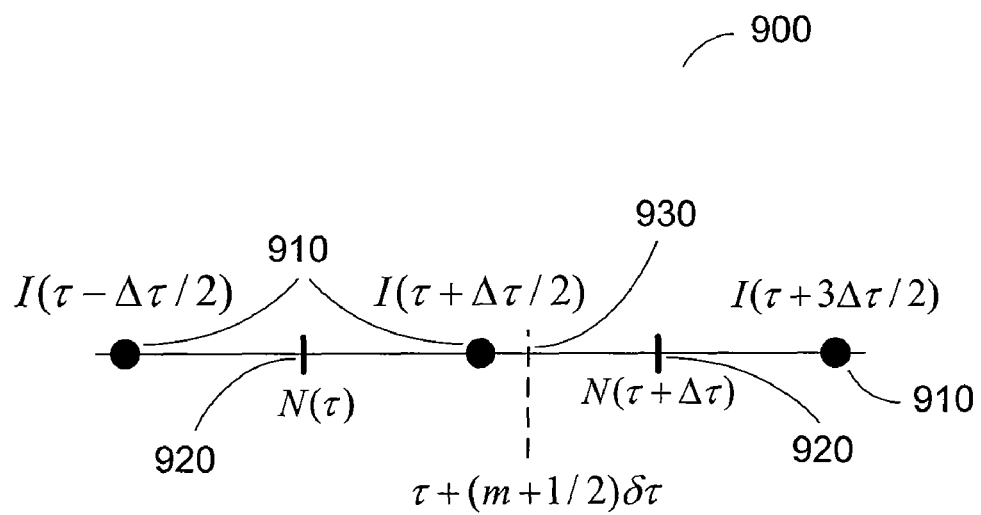
FIG. 9 is an exemplary diagram of temporal partitions on a temporal grid which may be used for sub-sampling calculations in accordance with certain exemplary embodiments of the present invention.

An integration domain can be subdivided into M sub-ranges $[\tau^m, \tau^{m+1}]$ with $\tau^m = \tau + m\delta\tau$, and a derivation similar to that described in Eqs. (23)-(28) above may be applied. FIG. 9 illustrates temporal partitions on a temporal grid 900 that may be used for a sub-sampling calculation. For example, dots 910 show temporal values where the intensity values may be calculated, solid lines 920 show temporal values where the density values may be calculated, and a dashed line 930 shows an exemplary sub-sampling time on the temporal grid 900.

An exemplary derivation of the sub-sampling determination described herein can be provided using only the squared intensity term in Eq. (34) (e.g., $\alpha=2$). The other exponential terms can be evaluated in the similar manner. The squared intensity term C2 may be written as Z:

$$C2(\text{for } \alpha = 2) = \exp\left(\frac{1}{\Delta\tau}\int_\tau^{\tau+\Delta\tau} D_2 I^2(\eta, \rho, \tau)d\tau'\right) \qquad (35)$$

$$= \exp\left(\frac{1}{\Delta\tau}\sum_{m=0}^{M-1}\int_{\tau^m}^{\tau^{m+1}} D_2 I^2(\eta, \rho, \tau)d\tau'\right)$$

$$= \prod_m \exp\left(\frac{1}{\Delta\tau} D_2 \int_{\tau^m}^{\tau^{m+1}} I^2(\eta, \rho, \tau)d\tau'\right) \qquad (36)$$

$$\approx \prod_m \exp\left(\frac{1}{\Delta\tau} D_2 \frac{\Delta\tau}{M}\frac{1}{2}\{I^2(\eta-\Delta\eta/2, \rho, \qquad (37)\right.$$

$$\tau^m + \delta\tau/2) + I^2(\eta+\Delta\eta/2, \rho, \tau^m+\delta\tau/2)\}\bigg)$$

$$\approx \prod_m \exp\left[\frac{1}{M}D_2\left(\lambda_m\frac{1}{2}\{I^2(\eta-\Delta\eta/2, \rho, \tau) + \qquad (38)\right.\right.$$

$$I^2(\eta+\Delta\eta/2, \rho, \tau)\} + \mu_m\frac{1}{2}\{I^2(\eta-\Delta\eta/2,$$

$$\rho, \tau+\Delta\tau) + I^2(\eta+\Delta\eta/2, \rho, \tau+\Delta\tau)\}\bigg]$$

$$\approx \prod_m \exp\left[\frac{1}{M}D_2\left(\lambda_m\frac{1}{2}\{(I)^2(\eta-\Delta\eta/2, \rho, \qquad (39)\right.\right.$$

$$(\tau)) + (I)^2(\eta+\Delta\eta/2, \rho, (\tau))\} + \mu_m\frac{1}{2}\{(I)^2$$

$$(\eta-\Delta\eta/2, \rho, (\tau+\Delta\tau)) + (I)^2(\eta+\Delta\eta/2,$$

$$\rho, (\tau+\Delta\tau))\}\bigg]$$

In Eq (37) the intensity terms $I^2(*,*,\tau^m+\delta\tau/2)$ (where the asterisks '*' represent the variables $\eta$ and $\rho$) may be replaced by expressions for their corresponding linear interpolation values $\lambda_m I^2(*,*,\tau) + \mu_m I^2(*,*,\tau+\Delta\tau)$, where $\lambda_m = (1-(m+\frac{1}{2})/M)$ and $\lambda_m + \mu_m = 1$, to obtain the expression shown in Eq. (38). The expression in Eq. (39) can be obtained by replacing the terms $I^2(*,*,\tau)$ and $I^2(*,*,\tau+\Delta\tau)$ with their average approximations $(I)^2(*,*,(\tau))$ and $(I)^2(*,*,(\tau+\Delta\tau))$ evaluated at $\tau=(i+\frac{1}{2})\Delta\tau$ [e.g., $I(*,*,\tau+(i+\frac{1}{2})\Delta\tau)$]. These average approximations can be written as:

$$(I)^2(*,*,(\tau)) \approx \frac{1}{2}\{I^2(*,*,\tau-\Delta\tau/2) + I^2(*,*,\tau+\Delta\tau/2)\}, \qquad (40)$$

$$(I)^2(*,*,(\tau+\Delta\tau)) \approx \frac{1}{2}\{I^2(*,*,\tau+\Delta\tau/2) + I^2(*,*,\tau+3\Delta\tau/2)\}. \qquad (41)$$

The other terms in Eq. (34) may be evaluated in a similar manner until the sub-sampling procedure is complete.

Using Eqs. (31) and (32), for each affected time sample, a refined version of Eq. (29) may be written as $$N_{n+1/2,j,i+1/2}^{(k)} \approx \qquad (42)$$

$$\prod_{m=0}^{M-1}\exp\left\{\frac{\Delta\tau T_0}{M}\left[\hat{D}_0 + \sum_{\alpha=1}^{N_A}\frac{\hat{D}_\alpha I_0^\alpha}{\alpha\hbar\omega_0}\times\left(\lambda_m\frac{1}{2}\{(I^\alpha)_{n,j,\bar{i}} + (I^\alpha)_{n+1,j,\bar{i}}^{(k)}\} + \right.\right.\right.$$

$$\left.\left.\left.\mu_m\frac{1}{2}\{(I^\alpha)_{n,j,\bar{i}+1} + (I^\alpha)_{n+1,j,\bar{i}+1}^{(k)}\}\right)\right]\right\}N_{n+1/2,j,i-1/2}^{(k)},$$

where M can be selected to ensure that the elements of the matrix in the exponent of Eq. (29) are each smaller than a certain threshold value. Eq. (42) is a general version of Eq. (39) above, which was derived only for the squared intensity term C2 (e.g., $\alpha=2$). The threshold value $\epsilon$ may be selected such that $0 < \epsilon < 1$, whereby the condition on M can then be written as:

$$M \equiv M(n, j, i) = \qquad (43)$$

-continued $$\min_{s_1,s_2}\left\{M',\frac{\Delta\tau T_0}{M'}\times\left|\begin{array}{l}\hat{D}_0[s_1,s_2]+\\ \frac{I_0}{\hbar\omega_0}\frac{1}{2}\{I_{n,j,i}+I^{(k)}_{n+1,j,i}\}\hat{D}_1[s_1,s_2]+\\ \frac{I_0^2}{2\hbar\omega_0}\frac{1}{2}\{(I^2)_{n,j,i}+(I^2)^{(k)}_{n+1,j,i}\}\hat{D}_2[s_1,s_2]+\\ \frac{I_0^3}{3\hbar\omega_0}\frac{1}{2}\{(I^3)_{n,j,i}+(I^3)^{(k)}_{n+1,j,i}\}\hat{D}_3[s_1,s_2]\end{array}\right|<\varepsilon\right\}.$$

The analysis of nonlinear materials may often be guided by measurements of their optical transmission. In conventional calculations, the radial domain may often be assumed to be constant. In exemplary embodiments of the present invention, both radial and temporal profiles of the solution may be used to analyze and/or compare transmission plots of a peak transmittance $T_\delta$ and a conventional integrated transmittance $T_E$. The peak transmittance and the integrated transmittance may be provided by the expressions $$T_\delta = \frac{\delta E_{out}(\rho^*,\tau^*)}{\delta E_{in}(\rho^*,\tau^*)}, \text{ s.t. } (\rho^*,\tau^*) = \underset{\rho,\tau}{\operatorname{argmax}}\delta E_{out}(\rho,\tau), \quad (44)$$

$$T_E = \frac{E_{out}}{E_{in}} = \frac{T_F\int_0^{+\infty}d\rho'2\pi\rho'\int_{-\infty}^{+\infty}d\tau' I(\eta_{\max},\rho',\tau')}{2\pi\int_0^{+\infty}d\rho'\rho'\int_{-\infty}^{+\infty}d\tau' I_0 e^{-(\tau')^2}e^{-(\rho')^2}}, \quad (45)$$

respectively, where $\delta E_{in,out}(\rho,\tau) \approx T_F \pi\sqrt{\pi}\delta\rho^2\delta\tau I(\eta_{min/max},\rho,\tau)$ and $T_F$ can represent a cumulative Fresnel transmittance at the interfaces.

The integrated value $T_E$ may be conventionally accepted as a useful parameter for quantifying nonlinear materials because it can be measured in a laboratory using readily available thermal detectors, which can average a pulse intensity over both space and time. The peak intensity can cause damage to opto-electronic detectors and sensors. Therefore, it may be useful to obtain a numerical verification of the validity of the laboratory measurements using thermal detectors. Because a pulse distortion can occur in both the temporal and radial domains, the computational and exemplary modeling procedures described herein may also be used to search both radial and temporal domains of a pulse to find a maximum value of the intensity which may be used to determine $T_\delta$.

Electronic Level Contributions to Absorption

Specific contributions from each electronic level to the total absorption may be estimated, if at all, using conventional procedures based on the dynamics of the population densities of electronic levels. However, relative contributions to the absorption may not be closely correlated with corresponding relative population densities. An exemplary system in which such a correlation is not observed, for example, can be AF455 at high input intensities. An estimation of electronic level contributions to the total absorption which is based solely on the population densities of the levels may therefore be inaccurate.

In exemplary embodiments of the present invention, specific contributions from each electronic level to the total absorption may be provided. For example, both population density values and intensity absorption due to each electronic level may be obtained for any propagation distance, radius, and time step. This can permit an accurate calculation of the relative contributions to the total absorption. To determine these values, a total intensity reduction $\Lambda_\zeta$ may be defined for a specific grid index $\zeta=\{n+\frac{1}{2},j,i-\frac{1}{2}\}$ as a product of individual intensity reductions $\Lambda_{s;\zeta}$, each due to energy levels s with nontrivial absorption cross-sections. This total intensity reduction may be written as:

$$\Lambda_\zeta = \prod_{s\in S_\sigma}\Lambda_{s;\zeta}; \quad (46)$$

$$S_\sigma = \{s \mid \sigma_1[s] + \sigma_2[s] + \sigma_3[s] > 0\}. \quad (47)$$

The individual reductions $\Lambda_{s;\zeta}$ can be obtained using Eq. (30) as corresponding exponential terms responsible for intensity decrease at a final iteration, k=K, and may be written as:

$$\Lambda_{s;\zeta} \equiv \Lambda_{s;n+1/2,j,i-1/2} = \quad (48)$$

$$\exp\left(-L_{df}N\Delta\eta\sum_{\beta=1}^{N_B}I_0^{\beta-1}\times\left\{\sigma_\beta[s]\cdot\frac{N^{(K)}_{s;n+1/2,j,i-1/2}+N^{(K)}_{s;n+1/2,j,i+1/2}}{2}\right\}\right.$$

$$\left.\frac{1}{2}\{I^{\beta-1}_{n,j,i}+I^{(K)\beta-1}_{n+1,j,i}\}\right).$$

To determine relative absorption contributions, intensity decay values may be provided which can have a form:

$$q_\zeta = 1 - \Lambda_\zeta, \quad (49)$$

$$p_{s;\zeta} = 1 - \Lambda_{s;\zeta}. \quad (50)$$

The total intensity decay values $q_\zeta$ can be used to analyze which part of a pulse predominantly decreases at a certain depth. Further, the intensity decay associated with a level s, $p_{s;\zeta}$, can determine a relative contribution $\hat{p}_{s;\zeta}$ through application of the following relationship:

$$\hat{p}_{s;\zeta} = p_{s;\zeta}\Big/\sum_{s'\in S_\sigma}p_{s';\zeta}. \quad (51)$$

A nonlinear relationship between the relative contributions $\hat{p}_{s;\zeta}$ and the population densities and intensities can indicate that approximating contributions from specific electronic levels to the total absorption based on available values of the population densities may not be accurate. The accuracy of this conventional approximation can be assessed by generating a plot of total intensity decays $q_{\{\zeta\}}$, and then superimposing plots of absolute contributions $q_{s;\{\zeta\}}$ derived from relative contributions $\hat{p}_{s;\{\zeta\}}$. The absolute contributions of the electronic levels to the total absorption can be obtained by scaling them to the total intensity decays, e.g., using the following relationship:

$$q_{s;\{\zeta\}} = \hat{p}_{s;\{\zeta\}} \cdot q_{\{\zeta\}}. \quad (52)$$

Results of the exemplary computational procedures for determining absorption behavior described herein may be compared to transmittance data measured in various nonlinear materials under a variety of lasing conditions. Certain nonlinear materials can be selected for comparison to provide a range of such generic materials described herein. For example, a $C_{60}$-toluene solution as described, e.g., in the McLean et al. publication, may be representative of a typical single photon absorbers, and it can exhibit reverse saturable absorption. An AFX chromophore AF455 described, for example, in the Rogers et al. publication, may represent a typical two-photon absorber. PPAI dye can represent a 3PA material as described, e.g., in the Wang et al. publication.

A comparison of theory with experiments can provide for specifying a time-(in)dependent shape of an incident pulse, $(f(\rho)),f(\rho,\tau)$. The analytical and numerical techniques described herein can assume that $(f(\rho)),f(\rho,\tau)$ can be represented by a Gaussian function, which may be consistent with experimentally-observed laser pulse shapes. Using the assumption of a Gaussian pulse shape, the incident laser intensity or electric field can be expressed as:

$$I(\eta=0,\rho,\tau) = I_0 \exp(-\tau^2)\exp(-\rho^2); I(\eta=0,\rho) = I_0 \exp(-\rho^2),$$

$$\text{or } E(\eta=0,\rho,\tau) = E_0 \exp(-\tau^2/2)\exp(-\rho^2/2); E(\eta=0,\rho) = E_0 \exp(-\rho^2/2) \quad (53)$$

Individual energy level contributions to the total absorption may be analyzed by averaging the relative and absolute contributions expressed in Eqs. (51) and (52) within a portion of the pulse's time duration. For example, the averaged relative contribution of an s-th level at $(\eta_n,\rho_j)$ within a time range $[\tau_0,\tau_1]$ can be written as $$\langle \hat{p}_s \rangle_{[\tau_0,\tau_1]} = \sum_{i,\tau_i \in [\tau_0,\tau_1]} \hat{p}_{s;[n,j,i]}. \quad (54)$$

EXAMPLE

$C_{60}$-Toluene Solution

The nonlinear material $C_{60}$ can be described as a reverse saturable absorber—a material having an ESA cross section that may be much higher than that of the ground state. The absorption energy diagram can be expressed as a combination of transition diagrams, e.g., $B_0 \cup B_2 \cup B_3$. This absorption energy diagram can be used to uniquely define the vectors and matrices of the coefficients for the rate and propagation expressions provided in Eqs. (15) and (16). For example, these vectors and matrices that describe the absorption behavior of $C_{60}$ can be written in the following form:

$$\sigma_1 = [\sigma_{01}, \sigma_{12}, 0, \sigma_{34}, 0]; \sigma_2 = \sigma_3 = 0; \quad (55)$$

$$\hat{D}_0 = \begin{pmatrix} 0 & k_{10} & 0 & k_{30} & 0 \\ 0 & -(k_{13}+k_{10}) & k_{21} & 0 & 0 \\ 0 & 0 & -k_{21} & 0 & 0 \\ 0 & k_{13} & 0 & -k_{30} & k_{43} \\ 0 & 0 & 0 & 0 & -k_{43} \end{pmatrix};$$

$$\hat{D}_1 = \begin{pmatrix} -\sigma_{01} & 0 & 0 & 0 & 0 \\ \sigma_{01} & -\sigma_{12} & 0 & 0 & 0 \\ 0 & \sigma_{12} & 0 & 0 & 0 \\ 0 & 0 & 0 & -\sigma_{34} & 0 \\ 0 & 0 & 0 & \sigma_{34} & 0 \end{pmatrix};$$

$$\hat{D}_2 = \hat{D}_3 = (0)_{5\times 5}.$$

Figure 2A:
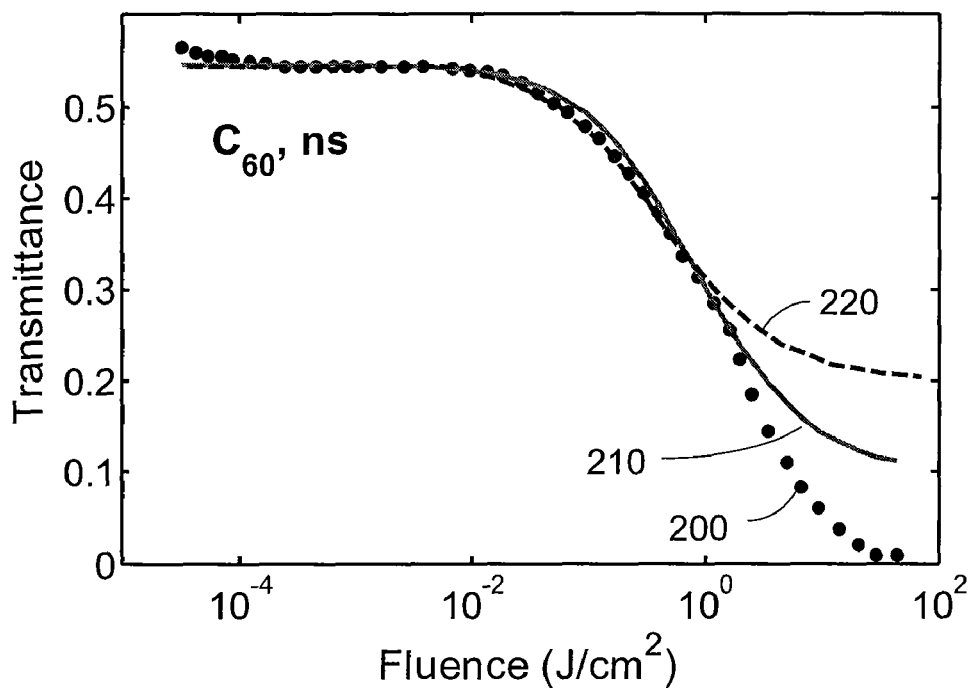
FIG. 2a is an exemplary graph of an energy transmittance $T_E$ as a function of input energy for $C_{60}$.

Exemplary coefficients and experimental parameters that may be used to describe several multiphoton-absorbing materials are provided in Table 1. A theoretical absorption behavior of $C_{60}$ can be determined using an iteration technique to solve Eqs. (30) and (42) with K=2. The results of this exemplary procedure are presented in FIG. 2a, which is an exemplary graph of energy transmittance $T_E$, shown in Eq. (45), as a function of input energy in $C_{60}$. Experimentally measured data 200 in FIG. 2a are indicated by • (dot) symbols, the thin solid line 210 represents results obtained using the computational technique described herein, and the thick solid line 220 represents an original solution provided in the McLean et al. publication. The measured transmittance data 200 presented in FIG. 2a is likely well-represented by the computational results 210 within an input fluence range from about $3.6\times 10^{-5}$ J/cm² to about 5 J/cm².

TABLE 1

Parameters for exemplary multiphoton absorbing materials.

| Material/experimental parameters | $C_{60}$-toluene solution[a] | AF455 chromophore[b] | PPAI dye[c] |
|---|---|---|---|
| $\sigma_{3P4}$ (cm³/W²) | | | $3.2 \times 10^{-21}$ |
| $\sigma_{TP4}$ (cm⁴/GW) | | $0.5 \times 10^{-20d}$ | |
| $\sigma_{01}$ (cm²) | $3.1 \times 10^{-18}$ | | |
| $\sigma_{12}$ (cm²) | $1.6 \times 10^{-17}$ | $1.68 \times 10^{-17}$ | |
| $\sigma_{34}$ (cm²) | $1.4 \times 10^{-17e}$ | $17.1 \times 10^{-17}$ | |
| $k_{10}^{-1}$ (ns) | 32.5 | 2.72 | |
| $k_{21}^{-1}$ (ps) | 1.0 | 1.66[f] | |
| $k_{13}^{-1}$ (ns) | 1.35 | 45.3 | |
| $k_{30}^{-1}$ (µs) | 40.0 | 0.368 | |
| $k_{43}^{-1}$ (ps) | 1.0 | 10.0[g] | |
| $Z_{max}$ (mm) | 1.0 | 1.0 | 10.0 |
| $L_{df}$ | 0.09 | 2.24 | 0.81 |
| $N_T$ (nm⁻³) | $1.559 \times 10^{-3h}$ | $0.012^i$ | $0.596 \times 10^{-3k}$ |
| k | | | |
| Energy levels diagram | $B_0 \cup B_1 \cup B_2$ | $B_1 \cup B_2 \cup B_3$ | $B_4$ |
| $R_0$ (µm) | $33.37^m$ | 13.01 | 53.03 |
| $T_0$ (ns) | 4.8 | 1.92 | $2.1 \times 10^{-2}$ |
| $\lambda_0$ (nm) | 532 | 800 | 1064 |

[a]Most parameters are provided in I. C. Khoo et al., "Nonlinear-absorbing fiber array for large-dynamic-range optical limiting application against intense short laser pulses," J. Opt. Soc. Am. B 21, 1234-1240 (2004); experimental parameters are provided in the McLean publication.
[b]Material and measurement parameters are provided in the experimental section of Sutherland et al.
[c]Parameters are provided in the Wang publication.
[d]Parameter is provided in the He publication and in the Kannan publication.
[e]Parameter is provided in the Khoo publication.
[f]Parameter is provided in the Rogers publication.
[g]Parameter is provided in the Kleinschmidt publication.
[h]This value corresponds to a 2.59 mM solution of $C_{60}$ in toluene
[i]This value corresponds to 0.02M
[k]This value corresponds to 0.99 mM of the dye in DMSO
[m]All laser parameters are obtained from corresponding original parameters using Eq. (53)

An analytical solution of Eqs. (15) and (16) such as that described, e.g., in the McLean publication may be less accurate in describing the evolution of the population densities at high fluence inputs than the numerical technique described herein. For example, the results of the numerical procedure 210 in FIG. 2a, performed in accordance with certain exemplary embodiments of the present invention, appear to more closely correlate with the experimental values 200 than does the analytical solution 220 for fluence values above about 1.4 J/cm². Neither solution, however, appears to match well with the measured data 200 above 5.0 J/cm².

Values of the contributions of individual electronic states to the total absorption of nanosecond pulses in $C_{60}$ can be provided in Table 2 below. These values were calculated using techniques described herein in accordance with exemplary embodiments of the present invention. The nonlinear transmittance of $C_{60}$ in the ns regime that is suggested by the data in Table 2 may be attributed primarily to a variation in the lowest triplet-triplet state absorption from about 66% to 99.8%, where this value may depending on the input energy value. The contribution values provided for $C_{60}$ in Table 2 (and for AF455 in Table 3 below) can be averaged within the portions of the pulse duration specified in Tables 2 and 3 using Eq. (54).

Figure 3A:
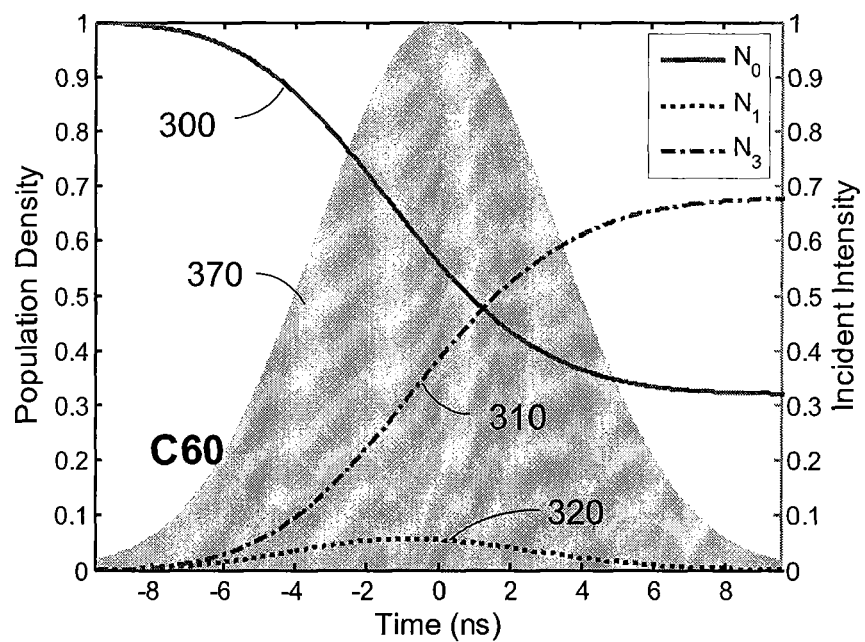
FIG. 3a is an exemplary graph of an evolution of electronic level population densities and total absorption in $C_{60}$ for an incident fluence value of 0.51 J/cm$^2$.
Figure 3B:
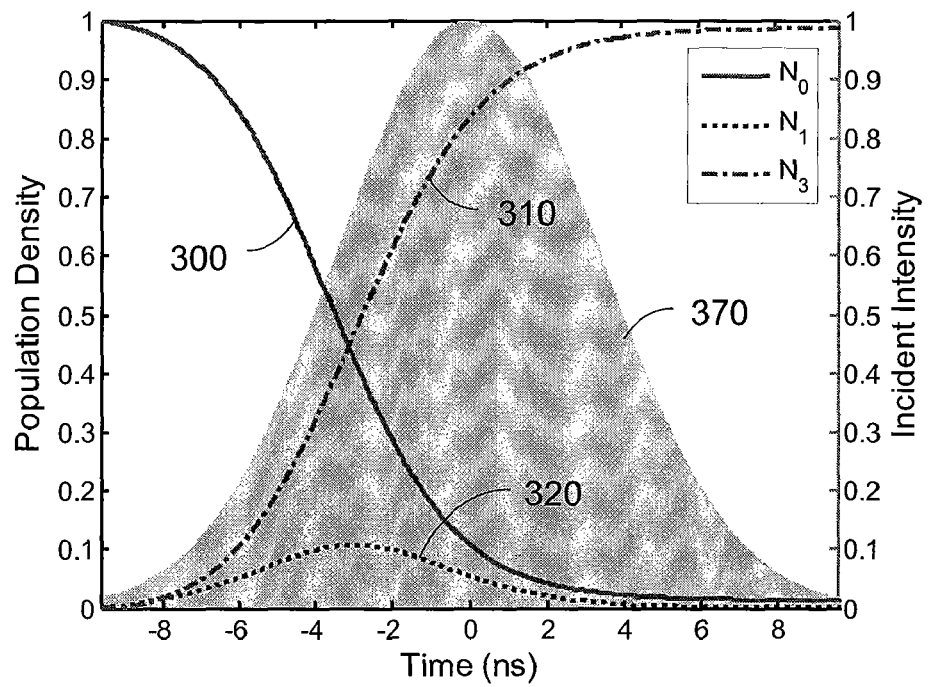
FIG. 3b is an exemplary graph of the evolution of electronic level population densities and total absorption in $C_{60}$ for an incident fluence value of 2.05 J/cm$^2$.
Figure 3C:
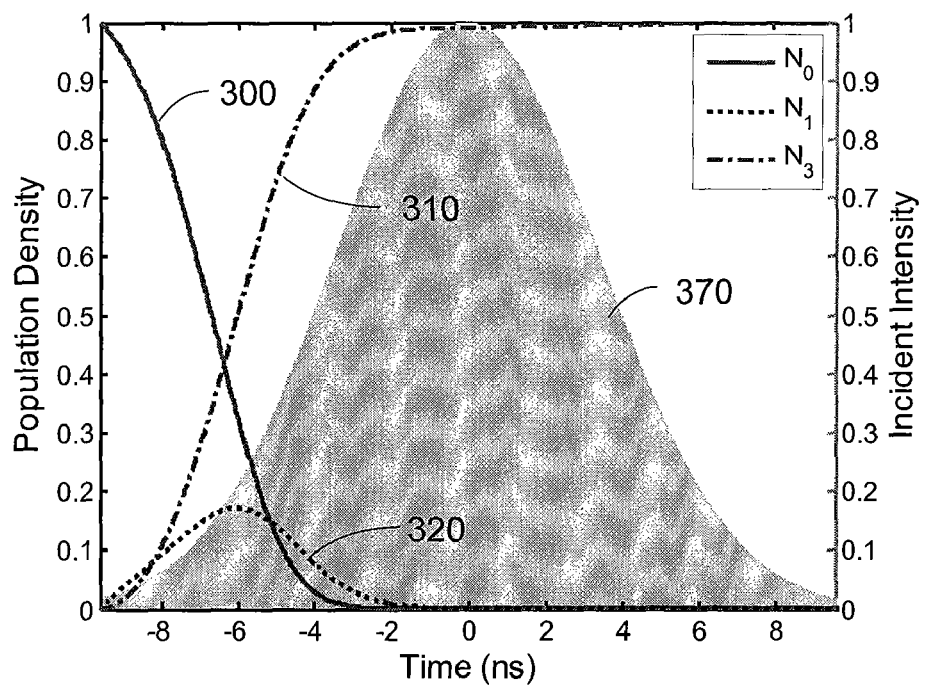
FIG. 3c is an exemplary graph of the evolution of electronic level population densities and total absorption in $C_{60}$ for an incident fluence value of 14.1 J/cm$^2$.
Figure 3D:
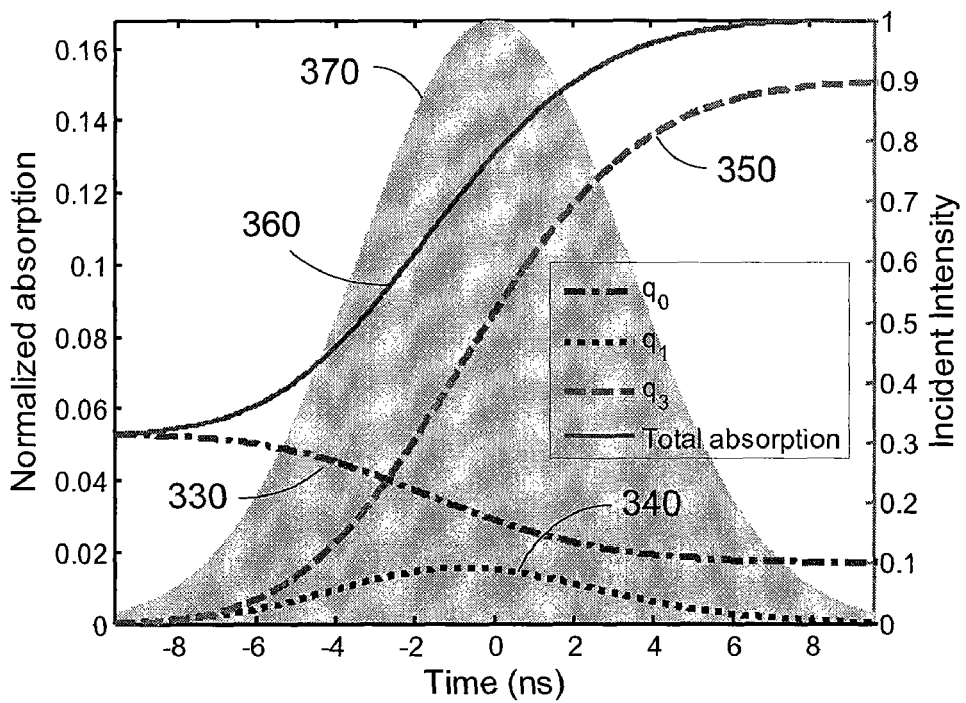
Figure 3E:
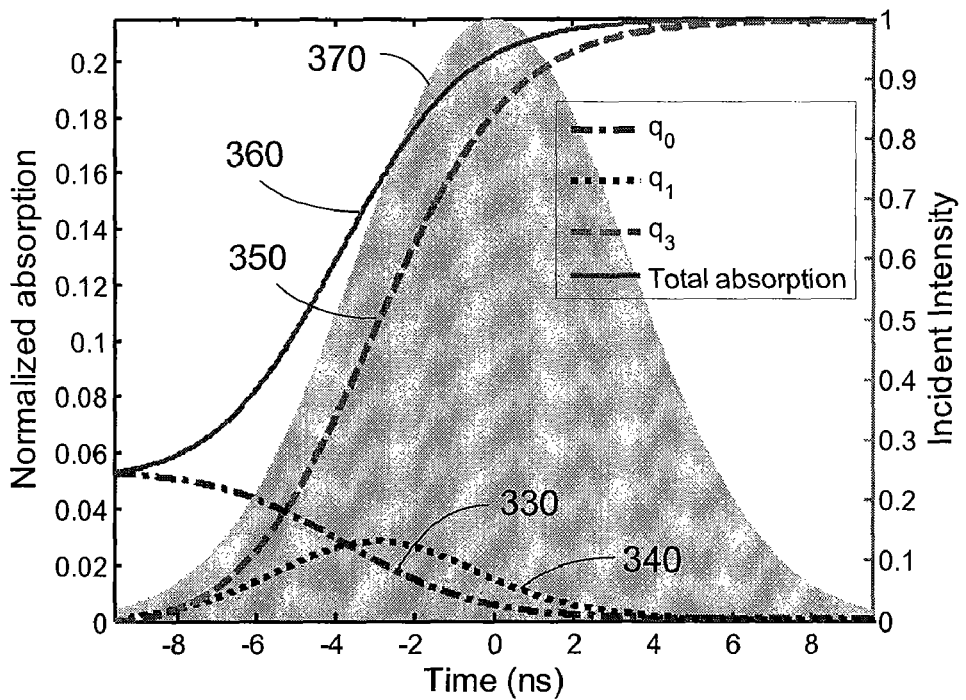
FIG. 3e is an exemplary graph of the absolute contributions to absorption from different active electronic levels corresponding to the conditions provided in FIG. 3b.
Figure 3F:
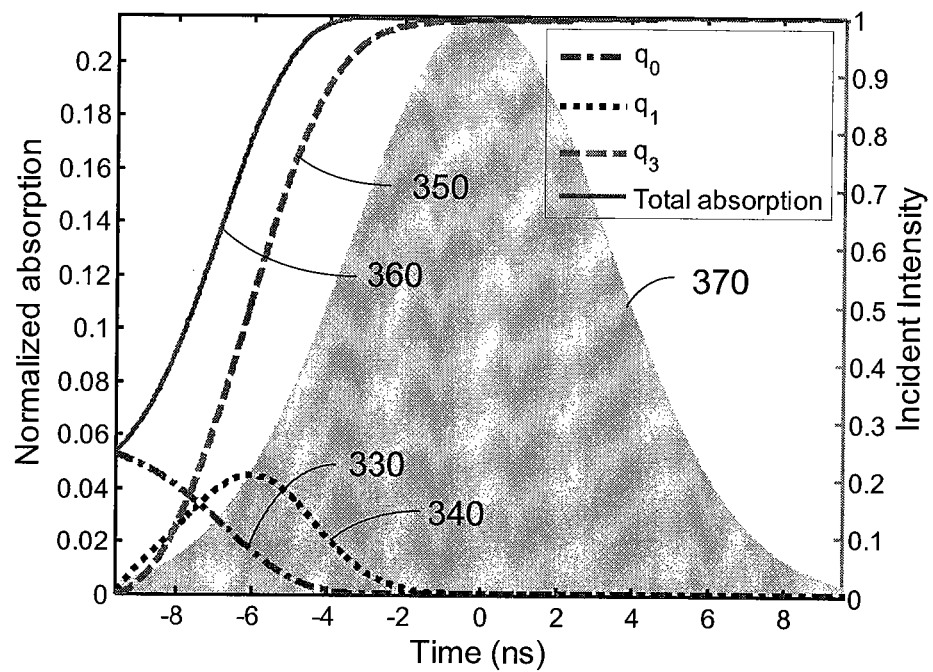
FIG. 3f is an exemplary graph of the absolute contributions to absorption from different active electronic levels corresponding to the conditions provided in FIG. 3c.

For example, FIGS. 3a-c show exemplary graphs of determined exemplary evolutions of population densities in electronic levels $N_0$ 300, $N_1$ 310 and $N_3$ 320 in $C_{60}$. FIGS. 3a-3c correspond to input fluence values, $\Phi_{in}$, of 0.51. 2.05 and 14.1 J/cm², respectively. The incident pulse intensity 370 is also shown as a function of time in these figures. FIGS. 3d-3f show three exemplary graphs of determined exemplary individual electronic level contributions $q_0$ 330, $q_1$ 340 and $q_3$ 350 to the absorption in $C_{60}$, together with the total absorption 360. The exemplary conditions used to generate FIGS. 3d-3f can correspond to the conditions in FIGS. 3a-3c, respectively. The values can be determined at the entrance of the slab (e.g., $\eta=0$) at the pulse center $\rho=0$.

In addition to the absorption by the triplet-triplet state $N_3$, the ground level can contribute approximately 23% to the total absorption at low input pulse intensities. This contribution may be lost at higher intensities because of a fast bleaching of the ground level. This may account for the observed agreement between calculations and experiments for input fluence values less than about 1.4 J/cm², reasonable agreement below about 5.0 J/cm², and a poor agreement of both methods with experimental values above about 5.0 J/cm². Material degradation at high input intensities may also be present, and can lead to a divergence of numerical solutions, based on integration of the rate-propagation equations, from the measured data.

TABLE 2

Individual contributions of electronic states of $C_{60}$ to the total absorption of nanosecond pulses

| Levels | $\Phi_{in} = 0.51$[a] | | | $\Phi_{in} = 2.05$ | | | $\Phi_{in} = 14.1$ | | |
|---|---|---|---|---|---|---|---|---|---|
| $\langle\hat{p}_0\rangle$[b] | 79.2 | 23.1 | 10.4 | 50.3 | 4.1 | 0.4 | 15.9 | 0.0 | 0.0 |
| $\langle\hat{p}_1\rangle$ | 6.7 | 10.3 | 1.7 | 15.2 | 8.0 | 0.3 | 19.0 | 0.6 | 0.0 |
| $\langle\hat{p}_3\rangle$ | 14.0 | 66.2 | 87.4 | 41.0 | 87.7 | 99.2 | 64.9 | 99.3 | 99.9 |
| $\langle q\rangle$[c] | 0.06 | 0.13 | 0.17 | 0.08 | 0.19 | 0.21 | 0.14 | 0.22 | 0.22 |

[a]For each specified input fluence value $\Phi_{in}$ (provided in J/cm²), three values are provided (in the left, middle, and right sub-columns) which correspond to the averaged relative contributions within the beginning, middle, and ending portions of pulse, e.g., $\langle*\rangle_{[-1,-1/3]}, \langle*\rangle_{[-1/3,1/3]}, \langle*\rangle_{[1/3,1]}$ as provided in Eq. (54).
[b]Averaged relative contribution to the absorption for an energy level 0, provided in Eq. (54), expressed as a percentage of the total absorption.
[c]Averaged intensity decay values obtained by integrating Eq. (49) using a technique similar to that used to integrate Eq. (54).

EXAMPLE

AF455

Figure 2B:
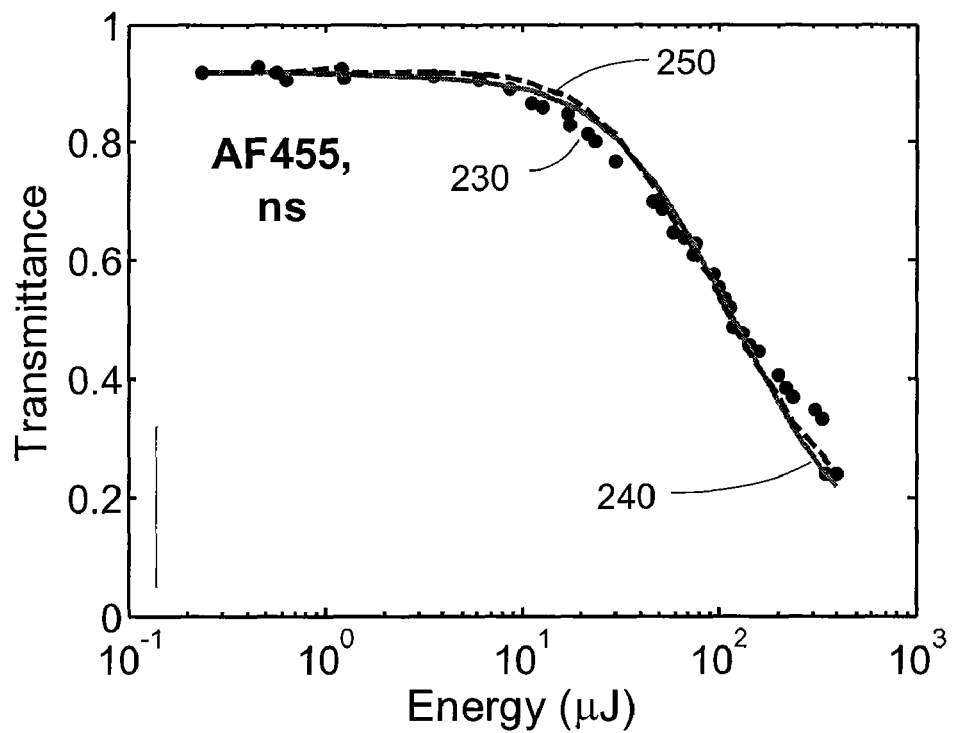
FIG. 2b is an exemplary graph of the energy transmittance $T_E$ as a function of input energy for AF455.

A theoretical exemplary basis for nonlinear transmittance in the ns regime of D-π-A chromophore AF455—a material which exhibits two-photon assisted ESA—together with experimental transmittance results is provided in the Sutherland et al. publication. The energy levels diagram for this material can be represented as a TPA by combining single photon absorption transition diagrams 110-130 shown in FIG. 1, e.g., $B_1 \cup B_2 \cup B_3$, and using the following parameters:

$$\sigma_1 = [0, \sigma_S, \sigma_T, 0, 0], \quad (56)$$

$$\sigma_2 = [\sigma_{TPA}, 0, 0, 0, 0],$$

$$\sigma_3 = 0$$

$$\hat{D}_1 = \begin{pmatrix} 0 & 0 & 0 & 0 & 0 \\ 0 & -\sigma_S & 0 & 0 & 0 \\ 0 & 0 & -\sigma_T & 0 & 0 \\ 0 & 0 & \sigma_T & 0 & 0 \\ 0 & \sigma_S & 0 & 0 & 0 \end{pmatrix},$$

$$\hat{D}_2 = \begin{pmatrix} -\sigma_{TPA} & 0 & 0 & 0 & 0 \\ \sigma_{TPA} & 0 & 0 & 0 & 0 \\ 0 & 0 & 0 & 0 & 0 \\ 0 & 0 & 0 & 0 & 0 \\ 0 & 0 & 0 & 0 & 0 \end{pmatrix},$$

$$\hat{D}_3 = (0)_{5\times 5},$$

where the matrix $\hat{D}_0$ in Eq. (55) associated with $C_{60}$ may also be used for this material. Calculated transmittance values 240 in AF455 are shown in FIG. 2b, together with experimental values 230 provided in the Sutherland publication (summarized in Table 1). The determined values 240, which were obtained using the exemplary embodiments of the present invention described herein, show agreement with the measured data 230 and with an analytical solution 250 that is also provided in the Sutherland et al. publication.

Figure 4A:
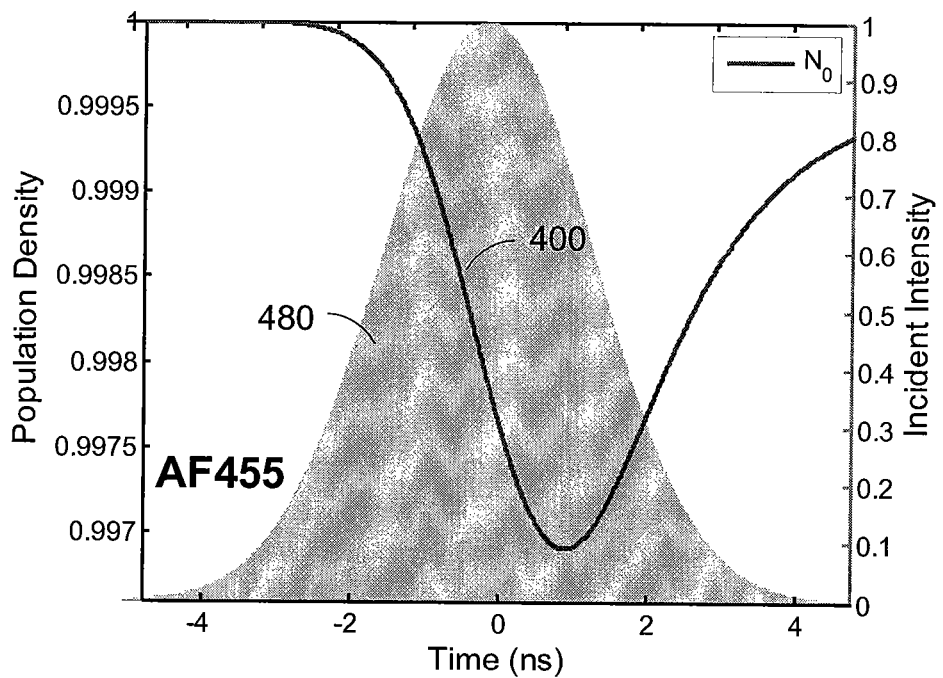
FIG. 4a is an exemplary graph of an evolution of electronic level population densities and total absorption in AF455 for an incident energy value of 17 µJ.
Figure 4B:
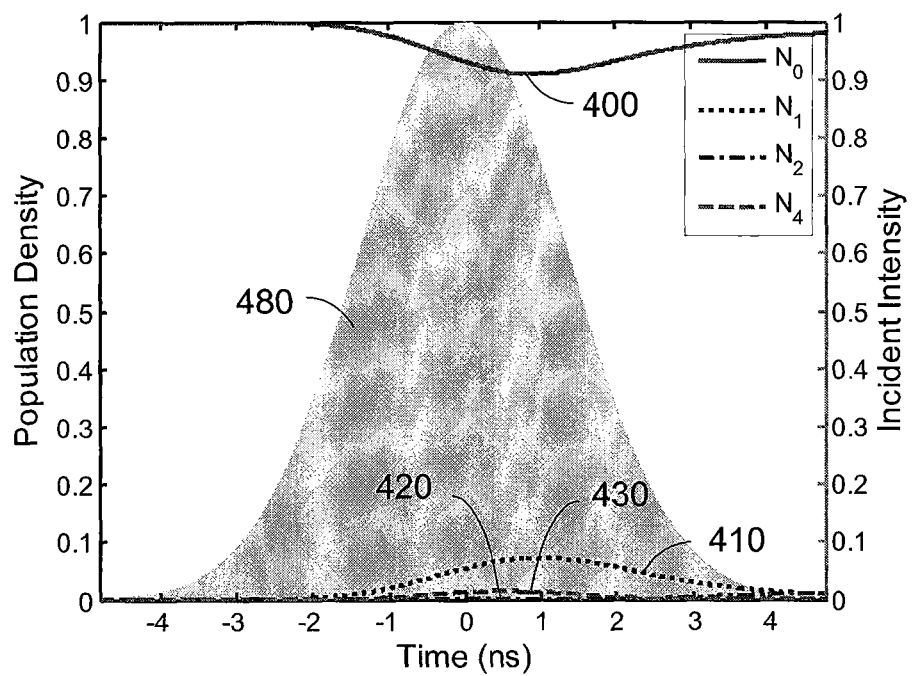
FIG. 4b is an exemplary graph of the evolution of the electronic level population densities and the total absorption in AF455 for the incident energy value of 93 µJ.
Figure 4C:
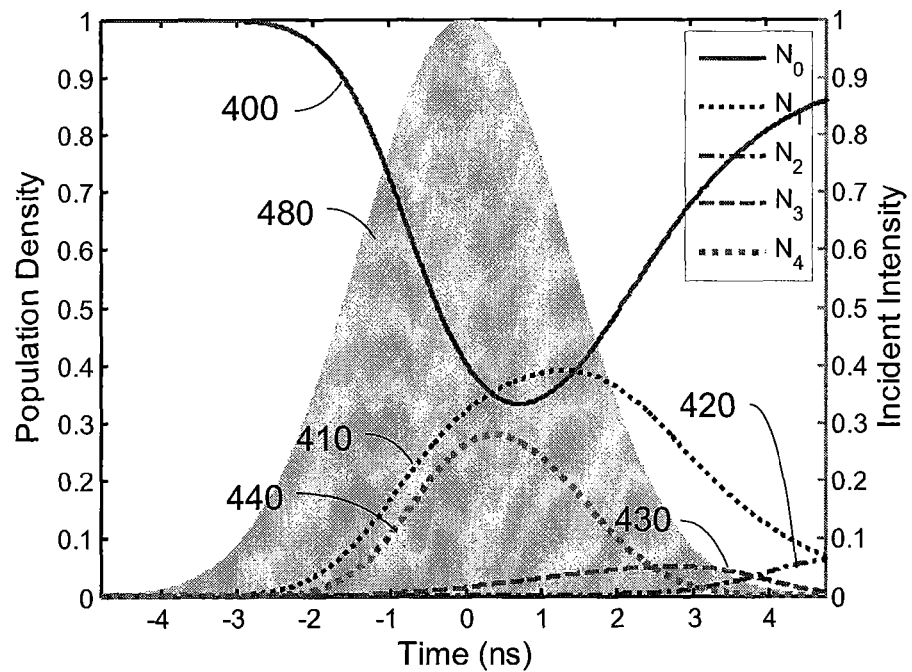
FIG. 4c is an exemplary graph of the evolution of the electronic level population densities and the total absorption in AF455 for the incident energy value of 0.33 mJ.
Figure 4D:
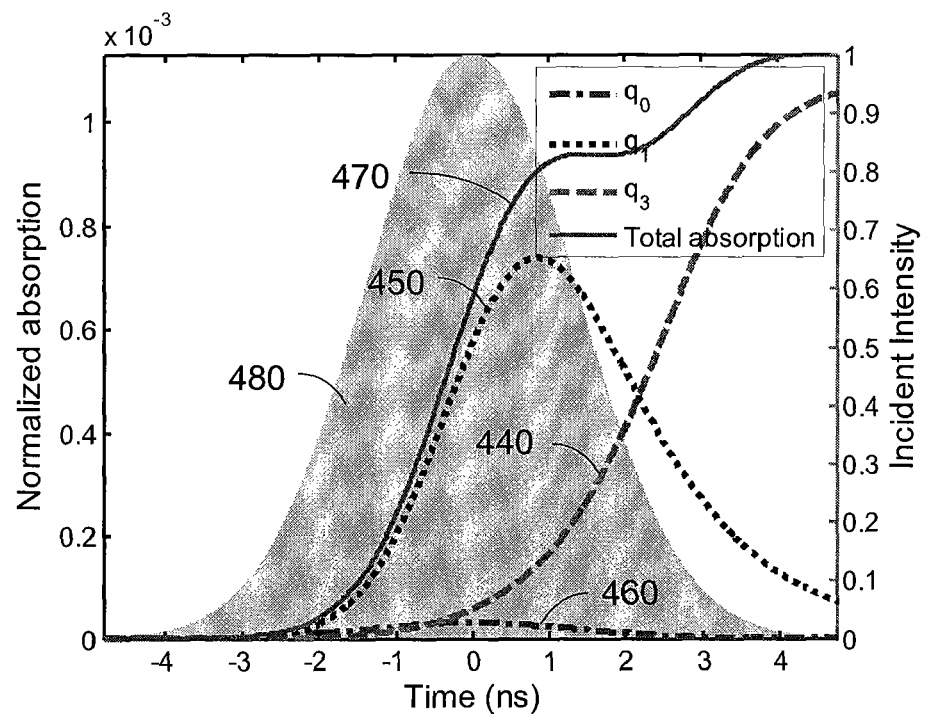
Figure 4E:
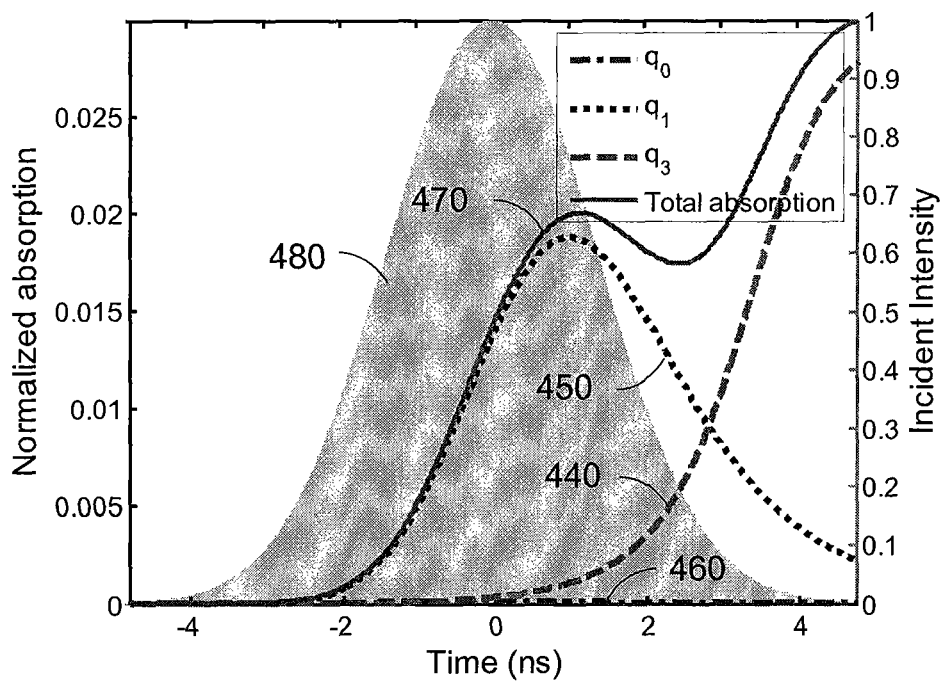
FIG. 4e is an exemplary graph of the absolute contributions to the absorption from different active electronic levels corresponding to the conditions provided in FIG. 4b.
Figure 4F:
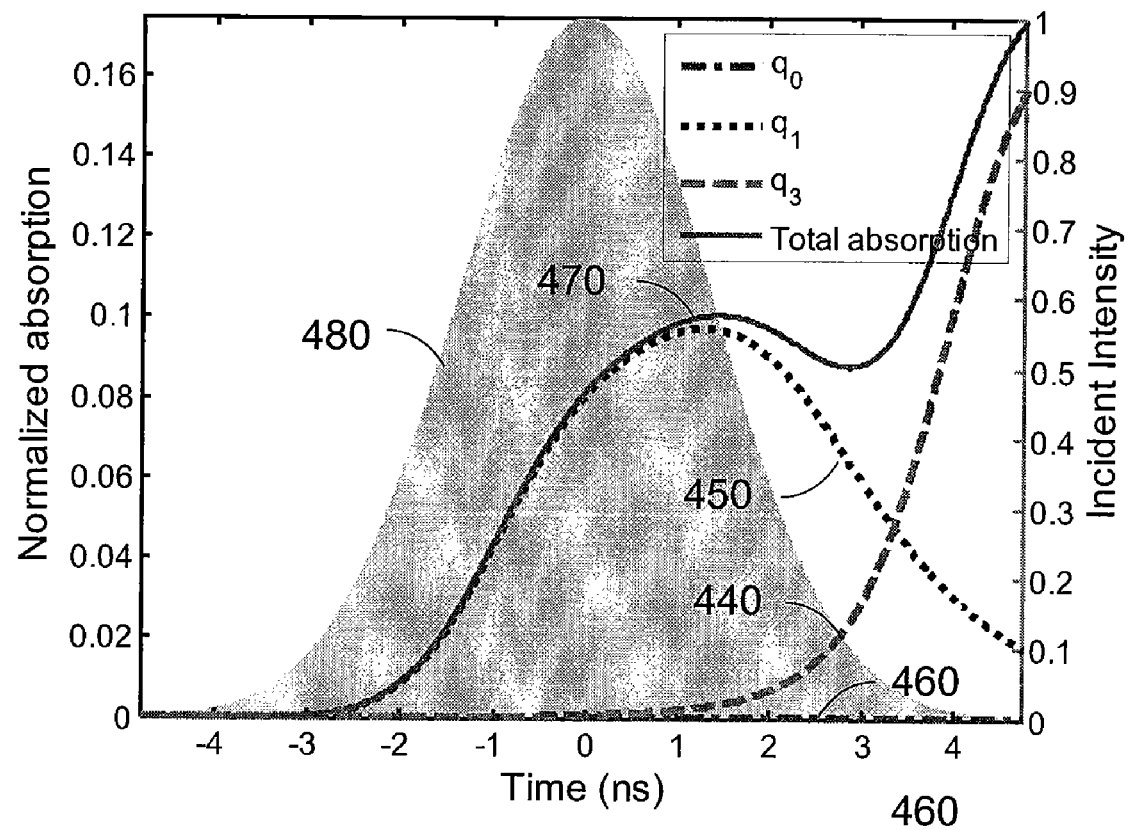
FIG. 4f is an exemplary graph of the absolute contributions to the absorption from different active electronic levels corresponding to the conditions provided in FIG. 4c.

FIGS. 4a-4f show exemplary graphs of absorption in AF455 of a ns scale pulse. FIGS. 4a-4c show exemplary determined evolutions of population densities in electronic levels $N_0$ 400, $N_1$ 410, $N_2$ 420 and $N_3$ 430 in AF455. FIGS. 4a-4c illustrate input energy values, $E_{in}$, of 17 μJ, 93 μJ, and 0.33 mJ, respectively. The incident pulse intensity 480 is also shown as a function of time in these figures. FIGS. 4d-4f show exemplary graphs of determined individual electronic level contributions $q_0$ 440, $q_1$ 450 and $q_3$ 460 to the absorption in AF455, together with the total absorption 470. The conditions used to generate FIGS. 4d-4f correspond to the conditions of FIGS. 4a-4c, respectively. The exemplary values are determined at the entrance of the slab (e.g., $\eta=0$) at the pulse center $\pi=0$.

Figure 8A:
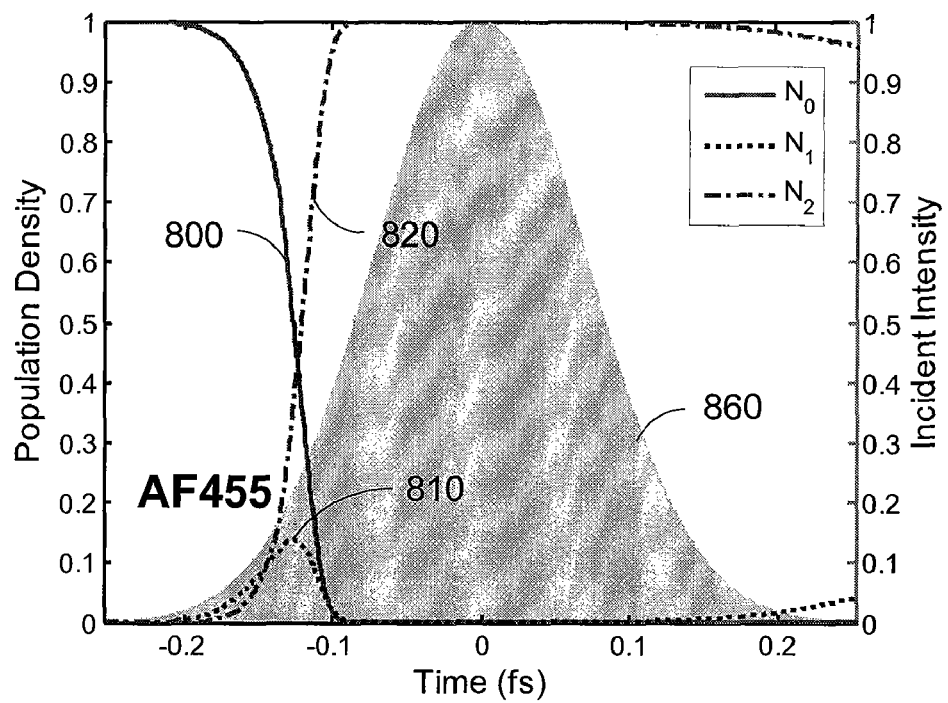
FIG. 8a is an exemplary graph of an evolution of the electronic level population densities at the surface of an AF455 0.412 mm slab for the pulse duration of 144.0 fs.

The population density graphs shown in FIGS. 4a-4b suggest a very small depletion of the ground level. This observation supports the validity of a steady-state approximation used by Sutherland et al. for the population densities in a ns pulse regime, and can account for the agreement between the numerical solution obtained using the techniques described herein and their analytical solution. A steady-state assumption may not be appropriate for higher input energies, because there may be a considerable increase of the population densities $N_1$ 410 and $N_3$ 430 as shown in FIG. 4c for a pulse duration in the ns regime. For a pulse duration in the fs regime, the ground state 80 may be depleted rapidly, as shown in FIG. 8a. Therefore, the exemplary embodiments of the present invention described herein may be more accurate for higher input intensities as they can encompass the dynamics of population densities, and do not require the use of a steady state approximation.

An analysis of absolute contributions from different electronic levels as shown, e.g., in the exemplary graphs in FIGS. 4d-4f, can provide certain information relating to absorption behavior within an AF455 sample for ns pulses. For example, most absorption can be seen to occur during the latter half of the propagating pulse, and can result in advancing the leading edge of a pulse as it propagations through a sample. For relatively small input energies, the ground level can be a main contributor to the total absorption, where approximately 61% of the average contribution to absorption can occur during the latter portion of the pulse. Details of this exemplary effect are provided, e.g., in Table 2 which provides the individual contributions averaged over the leading, central, and trailing parts of the propagating pulse at $\eta=0$ for the three indicated input energy values.

Table 3 herein provides exemplary data for contributions of individual states to the absorption of nanosecond pulses in AF455. Contribution of the ground state in TPA materials such as AF455 for high-energy pulses may falls abruptly as shown, for example, in columns 2 and 3 of Table 3. The main contributors to absorption can be ESA of the lowest singlet-singlet and the lowest triplet-triplet states with corresponding individual contributions of approximately 53.1% and approximately 74.7% for the central and latter portions of a pulse, respectively. (A contribution of 77.2% in the $\langle \hat{p}_0 \rangle$ level due to TPA in the early portion of a pulse may be less important because the associated absolute intensity decay value $\langle q \rangle$ can be 10 times less than corresponding values in other portions of the pulse).

TABLE 3

Individual contributions to the total absorption of nanosecond pulses by the electronic states of AF455.

| Levels | $E_{in} = 17.0$ μJ | | | $E_{in} = 93.0$ μJ | | | $E_{in} = 330.0$ μJ | | |
|---|---|---|---|---|---|---|---|---|---|
| $\langle \hat{p}_0 \rangle$ | 94.7 | 61.2 | 13.5 | 77.2 | 23.7 | 2.9 | 49.2 | 8.8 | 0.9 |
| $\langle \hat{p}_1 \rangle$ | 4.5 | 25.6 | 19.5 | 20.0 | 53.1 | 22.3 | 45.6 | 68.5 | 23.0 |
| $\langle \hat{p}_3 \rangle$ | 6.9 | 13.2 | 66.9 | 2.8 | 23.2 | 74.7 | 5.2 | 22.3 | 76.0 |
| $\langle q \rangle$ | 8.8e−5 | 8.8e−4 | 6.4e−4 | 5.8e−4 | 0.01 | 0.01 | 3.0e−3 | 0.08 | 0.12 |

EXAMPLE

PPAI

With the advent of lasers capable of providing shorter pulses and higher intensities, materials that exhibit three or more photon absorption processes can be studied. These materials may be of interest in areas such as laser micro- or nano-machining because of their ability to reduce the feature size of structures in substrate materials. In contrast to the nonlinear materials described herein, there may have been relatively little prior investigation of these materials including, e.g., a 3PA dye PPAI described in the Wang publication. Experimental investigations of this material indicate a high three-photon absorption cross-section in the near infrared region, so that all the parametric vectors and matrices may be zero or negligibly small, except for the following two:

$$\sigma_3 = [\sigma_{3PA}, 0], \hat{D}_3 = \begin{pmatrix} -\sigma_{3PA} & 0 \\ \sigma_{3PA} & 0 \end{pmatrix}. \quad (57)$$

Figure 2C:
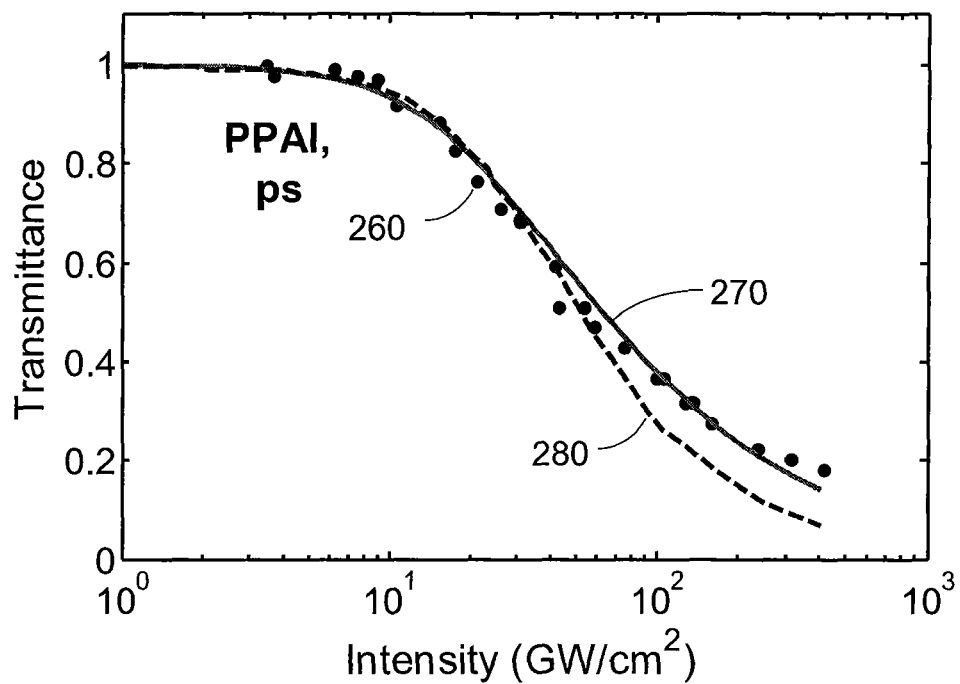
FIG. 2c is an exemplary graph of the energy transmittance $T_E$ as a function of input energy for PPAI.

The energy level absorption diagram for PPAI may include only a single building block $B_4$ 140 shown in FIG. 1, where the appropriate parameters are provided in Table 1. FIG. 2c shows a numerical solution 270 of the absorption behavior of PPAI, obtained using techniques in accordance with exemplary embodiments of the present invention. The solution 270 shows agreement with experimental transmittance measurements 260 provided in the Wang publication. Moreover, the present solution 270 appears to provide a better representation of the experimental data 260 in the high input intensity region than does the analytic solution 280 provided in the Wang publication.

Figure 5A:
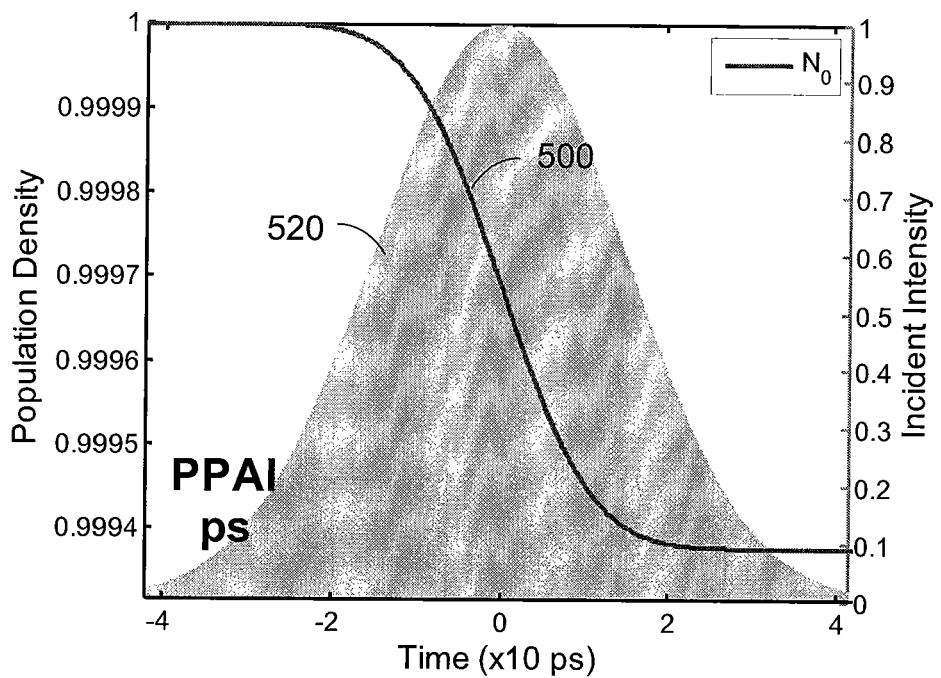
FIG. 5a is an exemplary graph of the electronic level population densities in PPAI for the incident intensity value of 16.9 GW/cm$^2$.
Figure 5B:
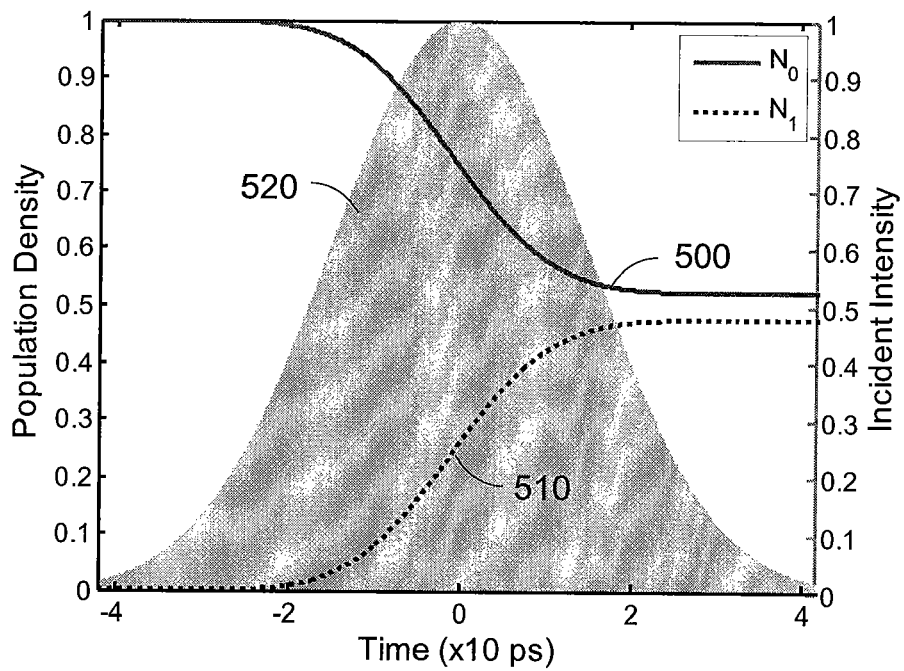
FIG. 5b is an exemplary graph of the electronic level population densities in PPAI for the incident intensity value of 204.5 GW/cm$^2$.

FIGS. 5a and 5b show two exemplary graphs of absorption in PPAI of a ps scale pulse having an incident intensity value, $I_{in}$, of 16.9 GW/cm² and 204.5 GW/cm², respectively. The evolution of the electronic level population densities levels $N_0$ 500 and $N_1$ 510, are shown at the entrance of the slab, $\eta=0$, and at $\rho=0$. The incident pulse intensity 520 is also shown in these graphs.

The analytical model described in the Wang publication for absorption ion PPAI includes the assumption that there is a constant population density of the ground level. This assumption may be reasonable for a low intensity pulse, which may be suggested in the graph of FIG. 5a. However, this assumption may not be reasonable for a high intensity pulse, as suggested by the time-resolved population density solution 500, 510 depicted in FIG. 5b. This solution shows that the population of the $N_0$ state 500 may decrease to less than half the initial value in the latter portion of the pulse. Dynamics of the population density of the $N_1$ state 510 shown in FIG. 5b also suggests that excited state absorption may significantly affect the transmittance at high input intensities.

Radially-Dependent Solutions

The exemplary numerical procedures described herein can include a radial dependence of various parameters, which can provide significant insight into absorption behavior of materials. Many conventional determinations can neglect a radial dependence, and may only approximate absorption behavior, e.g., by a single averaged value of the various parameters that may be a function, e.g., only of time.

Figure 6A:
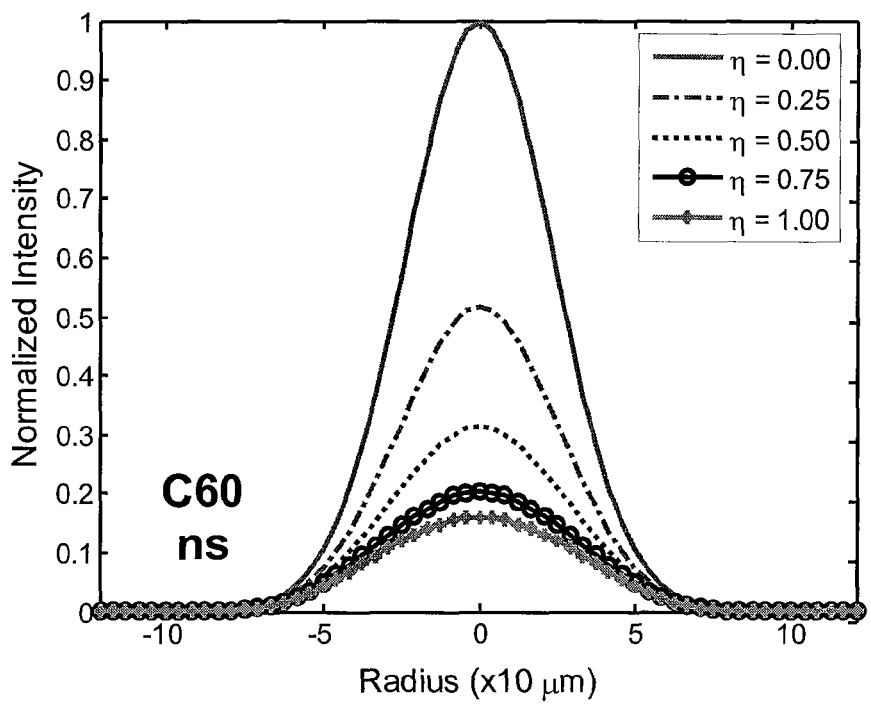
FIG. 6a is an exemplary graph of a numerical solution for an evolution of a pulse intensity in $C_{60}$ as a function of a radius at $\tau$=0 and at depths $\eta$={0.00, 0.25, 0.50, 0.75, 1.00} for an incident fluence value of 2.05 J/cm$^2$.
Figure 6B:
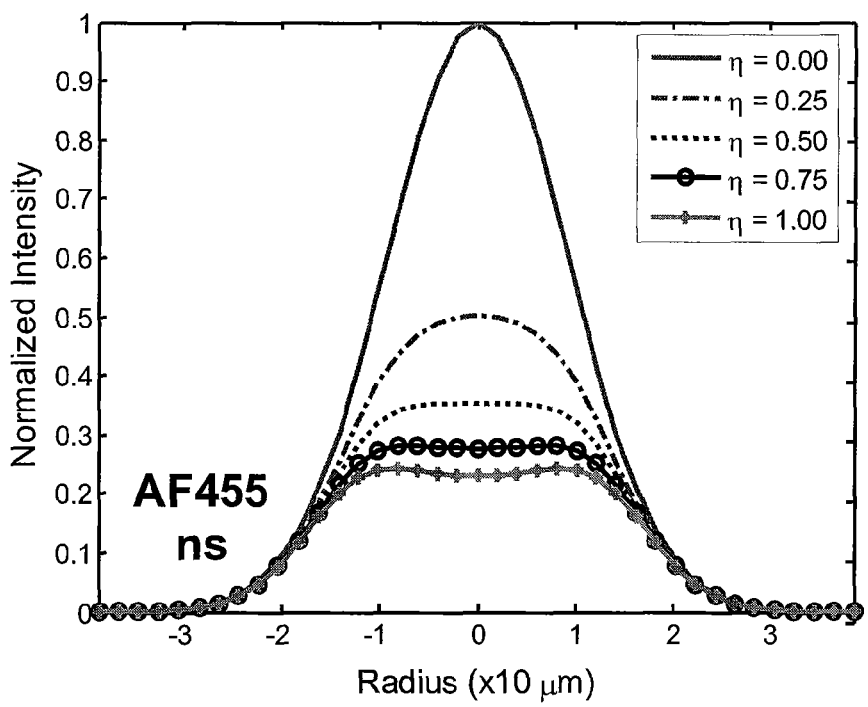
FIG. 6b is an exemplary graph of the numerical solution for the evolution of the pulse intensity in AF455 as a function of a radial distance at $\tau$=0 and at depths $\eta$={0.00, 0.25, 0.50, 0.75, 1.00} for the incident energy value of 131 µJ.
Figure 6C:
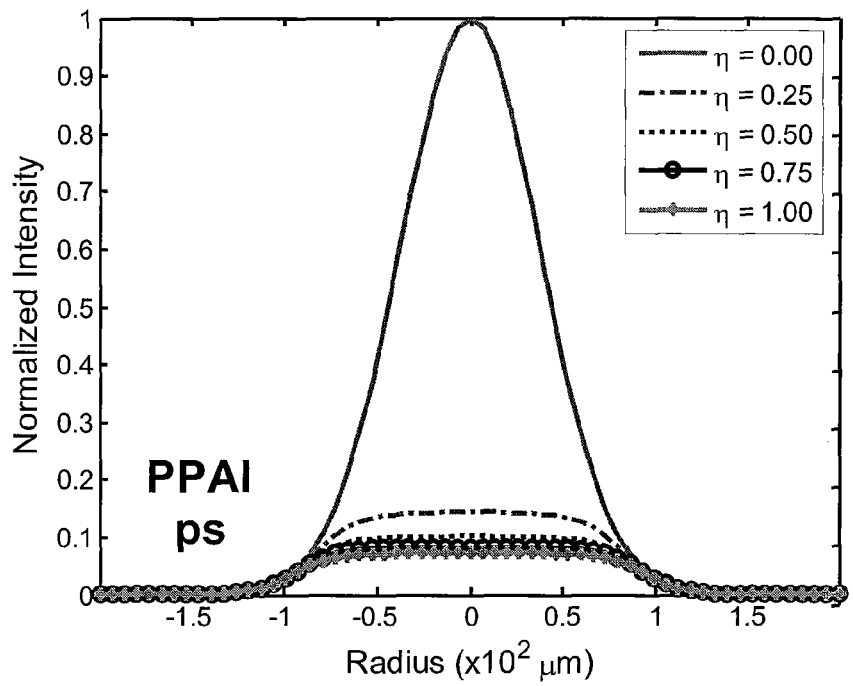
FIG. 6c is an exemplary graph of the numerical solution for the evolution of the pulse intensity in PPAI as a function of the radial distance at $\tau$=0 and at depths $\eta$={0.00, 0.25, 0.50, 0.75, 1.00} for the incident fluence value of 204.5 GW/cm$^2$.
Figure 6D:
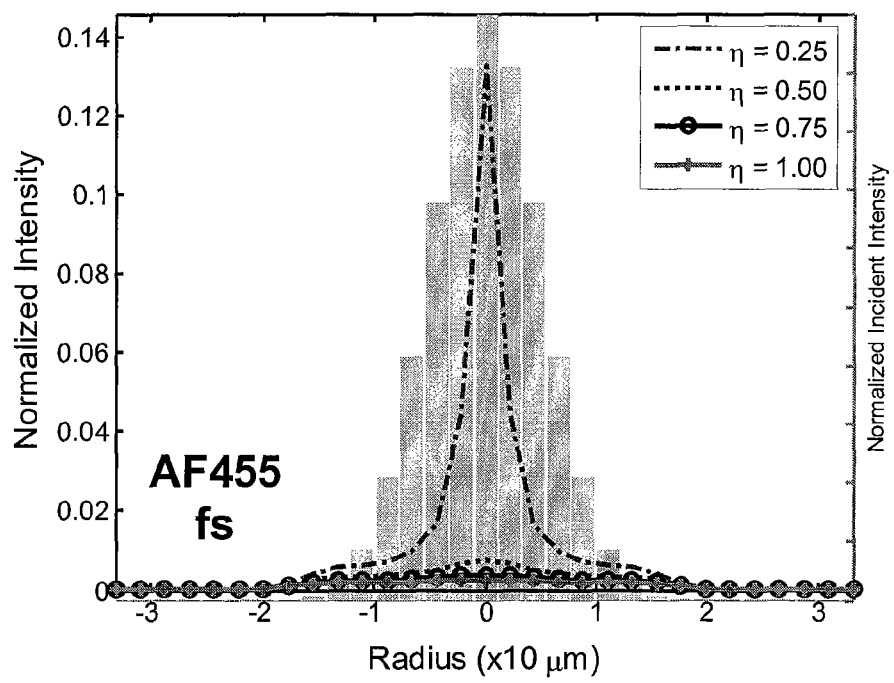
FIG. 6d is an exemplary graph of the numerical solution for evolution of the pulse intensity in AF455 as a function of the radial distance at $\tau$=0 and at depths $\eta$={0.00, 0.25, 0.50, 0.75, 1.00} for the incident energy value of 6.6 µJ and where $R_0$=7.07 µm and $T_0$=204.0 fs.

FIGS. 6a-d show exemplary graphs of numerical solutions of evolution of a pulse intensity as a function of radius at $\tau=0$ and at different depths $\eta=\{0.00, 0.25, 0.50, 0.75, 1.00\}$ for different MPA samples. For example, FIG. 6a shows an exemplary radial dependence of absorption behavior of a ns scale pulse in $C_{60}$ with an input fluence $\Phi_{in}=2.05$ J/cm². FIG. 6b shows an exemplary radial dependence of absorption behavior of a ns scale pulse in AF455 with an input energy $E_{in}=131$ μJ. FIG. 6c shows an exemplary radial dependence of absorption behavior of a ps scale pulse in PPAI for an incident energy intensity value $I_{in}=204.5$ GW/cm². FIG. 6d shows an exemplary radial dependence of absorption behavior of a fs scale pulse in AF455 with an input energy $E_{in}=6.6$ μJ, $R_0=7.07$ μm, and $T_0=204.0$ fs;

For MPA materials, e.g., AF455 and PPAI, not accounting for radial dependence of parameters in mathematical models when calculating absorption behavior may be a reasonable simplification. For example, the exemplary graph of pulse intensity in PPAI, shown in FIG. 6c, may be approximately flat soon after a pulse enters a sample (e.g., $\eta>0.25$). An initially Gaussian-shaped pulse in AF455 may gradually relax towards a plateau shape after propagation through the second half of the sample (e.g., $\eta>0.5$), as shown in FIGS. 6b and 6d. However, the Gaussian shape of an incident pulse propagating through the $C_{60}$ sample, shown in FIG. 6a, may likely not relax significantly in a radial direction until it reaches the end of the material. Therefore, assuming radial invariance of absorption behavior may not be an accurate assumption in certain materials such as $C_{60}$. Because the determinations that include a radial dependence may be time consuming, it may be desirable to determine if radial variations may play a significant role in absorption under certain conditions. If radial variations are not important, then simpler and less time consuming determinations can be performed using a procedure that assumes radial invariance which may still provide sufficiently accurate results.

There may be additional reasons to include radial dependence of parameters in absorption calculation techniques. The exemplary techniques described herein include determinations of near field properties of the laser beam pulse. However, certain detectors may conventionally be placed at a far field where radial distortions may cause problems. Such distortions may not be adequately described by conventional theories which neglect a radial dependence of the laser beam pulse. Based on the results shown, e.g., in FIGS. 2a-2c, a radial dependence of the beam pulse may not be significant for the experiments described herein. However, radial distortions may become more prominent in newer materials, and therefore it may be necessary to retain the radial dependence. Therefore, the radial dependence of the laser beam can be included in the exemplary determinations described herein. This can allow for the determination of radial distortions at a far field using a Huygens-Fresnel principle as described, e.g., in P. W. Milonni et al., *Lasers*, John Wiley, New York, 1988.

The radial distortion may also affect any self-focusing/defocusing that can arise if a material has a large nonlinear index of a refraction or if the input intensity is sufficiently large to induce such an effect. The results shown, e.g., in FIGS. 2a-2c, indicate that self-(de)focusing may have little significance in the experiments described here. However, if more powerful lasers are used, it may be important to include the radial dependence of the beam characteristics to obtain accurate predictions of absorption behavior.

Further exemplary embodiments of the present invention may be used to describe absorption of a plurality of coincident pulses (e.g., a "pulse train"). For example, an intensity or electric field of an incident pulse train can be described by the following equation:

$$I(0, r, t) = \sum_{n=0}^{N} I_n f(r, t - nt_r), \quad (58)$$

Or $$E(0, r, t) = \sum_{n=0}^{N} E_n f(r, t - nt_r),$$

where $I_n$ or $E_n$ is an initial peak intensity or peak electric field of an nth pulse, $t_r$ is a pulse separation, N is a number of pulses in the pulse train, and $f(r,t-nt_r)$ describes a shape of the incident pulse.

A pulse having a Gaussian shaped may be expressed by the function $$I(0,r,t)=I_0 \exp(-t^2/T_0^2) \exp(-r^2/R_0^2),$$

$$\text{or } E(0,r,t)=E_0 \exp(-t^2/2T_0^2)\exp(-r^2/2R_0^2) \quad (59)$$

where $I_0$ or $E_0$ is a peak intensity or peak electric field, $R_0$ is a 1/e pulse radius, and $T_0$ is a 1/e temporal pulse half-width. The input intensity corresponding to N pulses may be expressed as $$I(0, r, t) = \sum_{n=0}^{N} I_n \exp[-(t-nt_r)^2/T_0^2]\exp[-r^2/R_0^2], \quad (60)$$

or $$E(0, r, t) = \sum_{n=0}^{N} E_n \exp[-(t-nt_r)^2/2T_0^2]\exp[-r^2/2R_0^2].$$

This equation may be used instead of the expression provided, e.g., in Eq. (53) herein to determine the absorption effects resulting from a series of incident pulses.

Ultrashort Pulses

Unlike conventional numerical or analytical procedures, the exemplary procedures according to the present invention described herein can permit investigation of a variety of nonlinear absorption phenomena, including situations that may not have been measured experimentally such as, e.g., absorption of short-pulsed lasers. For example, certain exemplary embodiments of the present invention may be used to analyze interactions of ultrashort pulses with nonlinear materials such as, e.g., interactions of fs range pulses with AF455, a system that may not yet have been studied experimentally.

Figure 7:
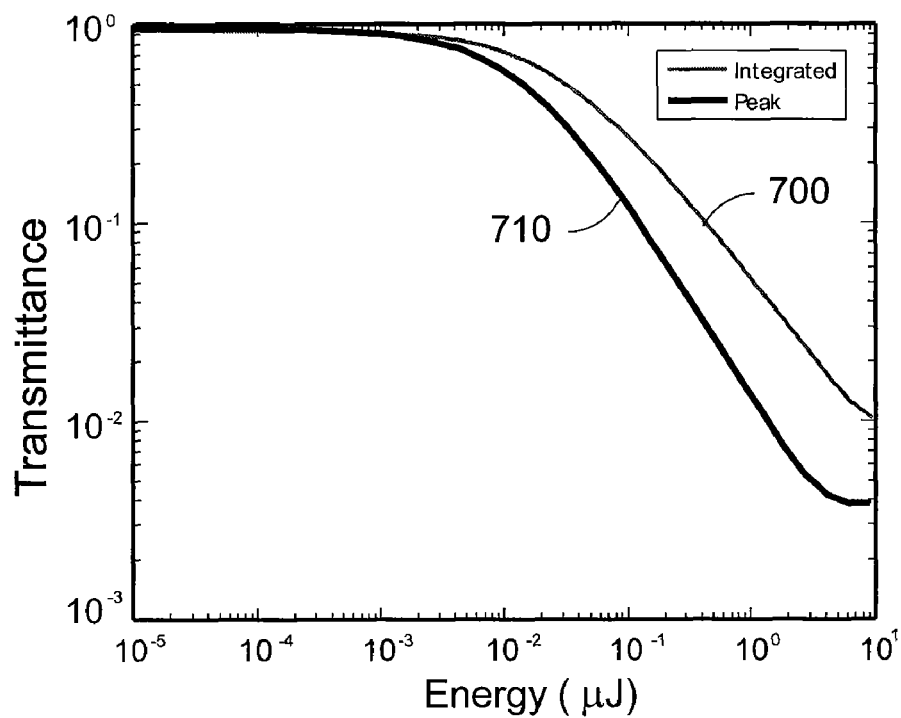
FIG. 7 is an exemplary graph of transmittance as a function of input energy for AF455 in a 0.41 mm slab for femtosecond pulses; (solid line) using integrated values (as in Eq. (22)), (dashed line) using certain peak values.

An ultrashort pulse may be characterized, e.g., by a Gaussian intensity distribution and parameters $R_0=7.07$ μm, $T_0=204.1$ fs, and $\lambda_0=800$ nm. \ Using these parameters and the data for AF455 provided in Table 1 herein, a transmittance of approximately 0.002 was obtained at the exit of an AF455 slab ($z_{max}=1.5L_{df}\approx0.412$ mm) for an input energy of approximately 100 μJ. FIG. 7 shows a graph of determined integrated transmittance 700 and peak transmittance 710 over a range of input energy values. The transmittance value of 0.002 for a fs scale pulse can be almost two orders of magnitude smaller than that obtained by using ns pulses. By increasing the slab thickness, an even lower transmittance may be achieved hypothetically, although possibly not with a sensitivity as strong as that of diffraction with respect to a longer sample thickness. Thus, AF455 may represent a desirable candidate for a high intensity nonlinear absorbing material.

Energy Level Population Dynamics

Still further exemplary embodiments of the present invention may be used to examine population dynamics and the contribution of individual energy levels to the total absorption. For example, FIG. 8a illustrates the evolution of electron population densities in levels $N_0$ 800, $N_1$ 810, and $N_2$ 820 at a sample entrance for an incident energy of 6.6 μJ. The ground level of a material exposed to such a high energy pulse can be quickly depleted and may not repopulate because of slow decay rates $k_{1,0}$ and $k_{3,0}$. The averaged values of ground level excitation contributions to the total absorption are calculated as approximately 95% within the first portion of pulse, approximately 48% in the second portion of the pulse, less than 0.01% in the final portion. The depopulation of the ground level can increase the electron density of the singlet-excited state $N_1$ followed by fast excitation to $N_3$, so that in the second half of the pulse the contribution of this state to the total absorption can be approximately 51%.

Figure 8B:
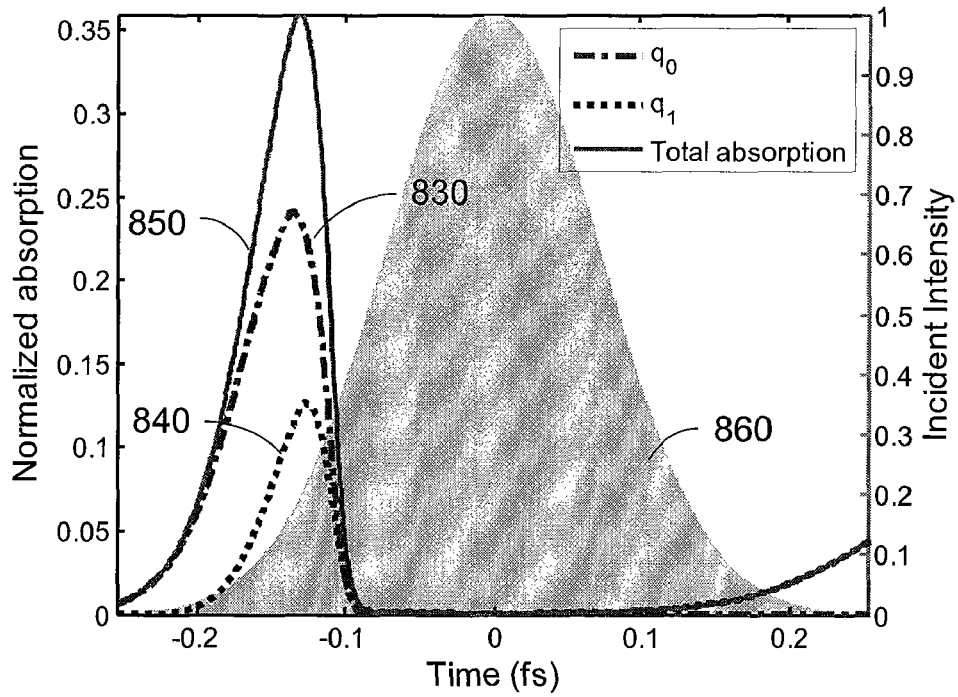

FIG. 8b shows a graph of the contributions of $q_0$ 830 and $q_1$ 840 to the total absorption 850 in AF455. The relative magnitudes of $q_0$ 830 and $q_1$ 840 in FIG. 8b may suggest that TPA can be more important than ESA for this material. For example, the averaged total absorption q 850 which may be expressed, as e.g., in Eq. (49), in a first portion of a pulse may be approximately 0.22, and in a second portion of the pulse it may be approximately 0.08. Thus, AF455 may be primarily a TPA material for pulses in the fs regime, whereas it may exhibit primarily TPA-assisted ESA behavior for pulses in the ns regime as shown, for example, in Table 3. Because an intersystem crossing time $1/k_{1,3}$ may be on the order of nanoseconds, the lowest triplet-triplet state $N_3$ may not contribute significantly to the total absorption. For example, the individual contribution the lowest triplet-triplet state $N_3$ can be less than $10^{-4}$% and is thus not shown in FIG. 8b. The numerical determinations of the absorption behavior of AF455 indicate, e.g., that the maximum values of $N_3$ and $N_4$ can be approximately $10^{-6}$.

The peak transmittance, shown in Eq. (44), can be below the integrated transmittance for all input energy values, as shown in FIG. 7. Therefore, the peak intensity of the transmitted pulse may not cause any damage to a detector placed behind an AF455-based limiter.

For example, direct measurements of the nonlinear Kerr coefficient have not been obtained for chromophores such as AF455. At high incident intensities, the Kerr nonlinearity may give rise to self-phase modulation, which in the presence of diffraction may lead to self-(de)focusing. In the presence of the dispersion, this nonlinearity may lead to a temporal pulse reshaping. If these phenomena are significant for a particular nonlinear material under certain conditions, then their effects can be accounted for, e.g., using techniques described in the Potasek publications and the Kovsh publication.

Stimulated Emission

Further exemplary embodiments of the present invention may be used, e.g., to describe stimulated emission effects from a two-photon absorption (TPA) state with nonlinear excited-state absorption (ESA). The emission may be to a conduction band or it may be a free electron excitation. An exemplary material that can exhibit stimulated emission effects and which may be described using exemplary embodiments of the present invention is a Green Fluorescent Protein (GFP) as described, e.g., in S. Kirkpatrick et. al., "Nonlinear Saturation and Determination of the Two-Photon Absorption Cross Section of Green Fluorescent Protein", J. Phys. Chem. B 2001, 2867 (2001).

Figure 10:
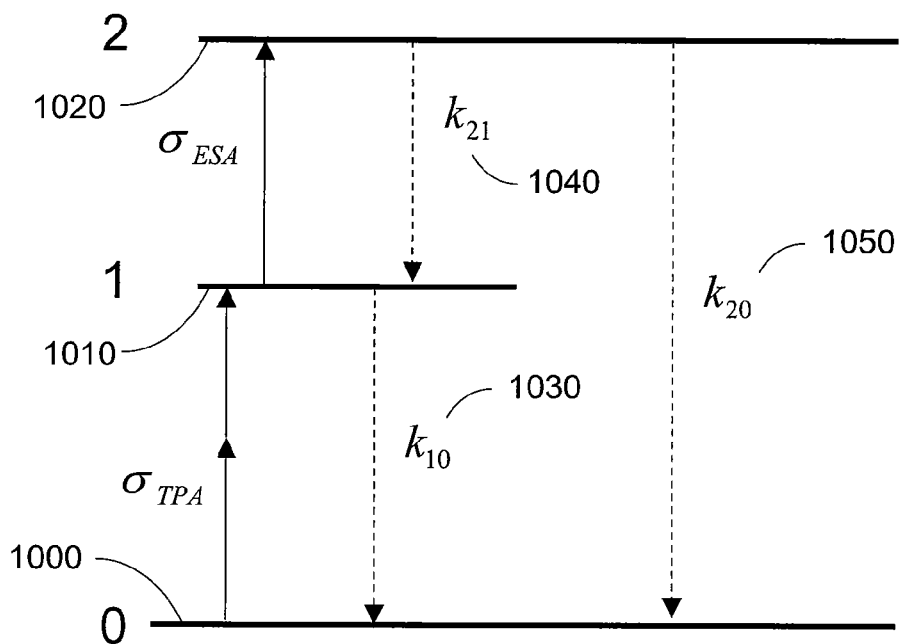
FIG. 10 is an exemplary diagram of an electronic configuration of an exemplary material which includes a ground state manifold, a first excited state manifold, and a second excited state manifold.

For example, an exemplary electronic configuration of a material is shown in FIG. 10 which includes certain exemplary states: e.g., a ground state manifold 1000, a first excited state manifold 1010, which may be reached through a TPA event and can be referred to as a TPA-state, and a second excited state 1020, which can be reached via a one photon absorption event from the first excited state manifold 1010. The second excited state 1020 can be referred to as an ESA-state, and it may be a conduction band or a free electron excitation. A stimulated emission can occur between the first excited state 1010 and the ground state 1000. A spontaneous emission can occurs between the second excited state 1020 and the first excited state 1010, or between the second excited state 1020 and the ground state 1000.

Parameters $k_{10}$ 1030 and $k_{21}$ 1040 shown in FIG. 10 can represent decay rates of the TPA-state 1010 and the ESA-state 1020, respectively, and the parameter $k_{20}$ 1050 can represent a decay rate from second excited state 1020 to the ground state 1000.

The corresponding matrices that may be used in the rate equation provided in Eq. (15) can be written as:

$$\hat{D}_0 = \begin{bmatrix} 0 & k_{10} & k_{20} \\ 0 & -k_{10} & k_{21} \\ 0 & 0 & -(k_{20}+k_{21}) \end{bmatrix}; \tag{61}$$

$$\hat{D}_1 = \begin{bmatrix} 0 & 0 & 0 \\ 0 & -\sigma_{ESA} & 0 \\ 0 & \sigma_{ESA} & 0 \end{bmatrix};$$

$$\hat{D}_2 = \begin{pmatrix} -g^{10}\sigma_{TPA} & \sigma_{TPA} & 0 \\ g^{10}\sigma_{TPA} & -\sigma_{TPA} & 0 \\ 0 & 0 & 0 \end{pmatrix}.$$

The parameter $g^{10}=g^1/g^0$ may also be used, where $g^1$ and $g^0$ can represent an electron degeneracy of electronic levels 1 and 0, respectively. In the present example, all other matrices: $\hat{D}_{N_A}(\sigma_{[N_A]PA})=0$; $\sigma_1=(0,\sigma_{ESA},0)$, $\sigma_2=(g^{10}\sigma_{TPA},\sigma_{TPA},0)$; and all other vectors $\sigma_{N_B}(\sigma_{[N_B]PA})=0$.

A phenomenological propagation equation for the intensity I, similar to Eq. (16), can be expressed as:

$$\frac{d\tilde{I}}{dz} = -\sigma_{TPA}\tilde{I}^2(\tilde{N}_1 - g^{10}\tilde{N}_0) - \sigma_{ESA}\tilde{I}\tilde{N}_1. \tag{62}$$

Using a change of variables as in Eq. (18), leads to a following form of the propagation equation:

$$\frac{dI}{d\eta} = -\sigma_{TPA}I^2(N_1 - g^{10}N_0) - \sigma_{ESA}IN_1. \tag{63}$$

Diffraction Effects

The exemplary embodiments of the present invention described herein may not necessarily account for effects of diffraction during multi-photon absorption in nonlinear materials. Diffraction effects can be accounted for by modifying the rate and propagation expressions provided in Eqs. (15) and (16). These propagation expressions are expressed in terms of intensity. However, it may be preferable for certain interactions to express the propagation equations in terms of a corresponding electric field. Both real and imaginary portions of the electric field can be calculated as described, e.g., in the Potasek publications.

It can be convenient to express the electric field in terms of a normalized function:

$$\tilde{E}(z,r,t)=\tilde{Q}(z,r,t)Q_0', \quad Q_0'^2 \equiv \epsilon_0 Q_0'^2. \tag{64}$$

Using the transformations provided in Eq. (17), the electric field can be written in dimensionless parameters:

$$E(\eta,\rho,\tau)=Q(\eta,\rho,\tau)Q_o'. \tag{65}$$

To include effects of diffraction in the model, the intensity can be expressed in terms of a classical complex electric field, $E_c$, provided in Eq. (2), using the expression:

$$\tilde{I}=\epsilon_0 nc_0 \langle E_c^2 \rangle. \tag{66}$$

The exemplary system of equations can be made dimensionless using the transformations provided herein to obtain Eq. (17), together with the following relationship:

$$\langle E_c, E_c \rangle = 2Q_0'^2 \langle Q, Q \rangle = \frac{2}{\varepsilon_0} Q_o^2 \langle Q, Q \rangle, \tag{67}$$

which can lead to the following expression for the field intensity:

$$\tilde{I}(\eta,\rho,\tau) = 2nc_0Q_0^2 \langle Q(\eta,\rho,\tau), Q(\eta,\rho,\tau) \rangle = 2nc_0Q_0^2 \overline{Q}(\eta,\rho,\tau), \quad (68)$$

with $$\overline{Q} \equiv \langle Q, Q \rangle. \quad (69)$$

Using the transformations described above, the rate equation corresponding to Eq. (15) can be expressed as:

$$\frac{dN(\eta, \rho, \tau)}{d\tau} = T_0 \left[ \hat{D}_0 + \sum_{\alpha=1}^{N_A} \frac{\hat{D}_\alpha}{\alpha \hbar \omega_0} (2nc_0 Q_0^2)^\alpha \overline{Q}^\alpha(\eta, \rho, \tau) \right] N(\eta, \rho, \tau). \quad (70)$$

Eq. (70) can be expressed in a more compact form using the following substitutions:

$$D_0 \equiv T_0 \hat{D}_0, \quad (71)$$

$$D_\alpha \equiv T_0 \frac{\hat{D}_\alpha}{\alpha \hbar \omega_0} (2nc_0 Q_0^2)^\alpha. \quad (72)$$

which can lead to the following equation:

$$\frac{dN(\eta, \rho, \tau)}{d\tau} = \left[ D_0 + \sum_{\alpha=1}^{N_A} D_\alpha \overline{Q}^\alpha(\eta, \rho, \tau) \right] N(\eta, \rho, \tau), \quad (72)$$

A rate operator $\Upsilon$ may be introduced as $$\Upsilon(\eta, \tau) \equiv \Upsilon_0 + \sum_{\alpha=1}^{N_A} \Upsilon_\alpha^{\overline{Q}}(\eta, \tau), \quad (73)$$

with $\Upsilon_0 \equiv D_0$ and $\Upsilon_\alpha^{\overline{Q}}(\eta,\tau) \equiv D_\alpha \overline{Q}^\alpha(\eta,\rho,\tau)$, which can lead to the following form of the rate equation:

$$\frac{dN(\eta, \rho, \tau)}{d\tau} = \Upsilon(\eta, \tau) \cdot N(\eta, \rho, \tau), \quad (74)$$

Using the transformation provided in Eq. (68), a dimensionless propagation equation corresponding to Eq. (16) which does not contain a term to account for diffraction effects can be written as:

$$\frac{dQ(\eta, \rho, \tau)}{d\eta} = \quad (75)$$

$$\left\{ -L_{df} N \left[ \sum_{\beta=1}^{N_B} (\tilde{\sigma}_\beta \cdot N(\eta, \rho, \tau))(2nc_0 Q_0^2)^{\beta-1} \overline{Q}^{\beta-1}(\eta, \rho, \tau) \right] - \tilde{c} L_{df} \right\} Q(\eta, \rho, \tau),$$

or, equivalently, as:

$$\frac{dQ(\eta, \rho, \tau)}{d\eta} = \left\{ -\sum_{\beta=1}^{N_B} (\sigma_\beta \cdot N(\eta, \rho, \tau)) \overline{Q}^{\beta-1}(\eta, \rho, \tau) - c \right\} Q(\eta, \rho, \tau), \quad (76)$$

by using the substitutions $\sigma_\beta \equiv L_{df} N (2nc_0 Q_0^2)^{\beta-1} \tilde{\sigma}_\beta$ and $c \equiv \tilde{c} L_{df}$.

Eq. (76) may be rewritten in an operator form by introducing absorption operators $\Phi_\beta^Q$, $\Phi_\beta^N$ and $\Phi_L$ to account for absorption due to the intensity, electronic density, and the linear absorptions, respectively, where $\Phi_\beta^N(\eta,\tau) \equiv \sigma_\beta \cdot N(\eta,\rho,\tau)$, $\Phi_\beta^Q(\eta,\tau) \equiv \overline{Q}^{\beta-1}(\eta,\rho,\tau)$, and $\Phi_L \equiv c$. The resulting equations may be expressed as:

$$\Phi(\eta, \tau) \equiv -\sum_{\beta=1}^{N_B} (\sigma_\beta \cdot N(\eta, \rho, \tau)) \overline{Q}^{\beta-1}(\eta, \rho, \tau) - c \quad (77)$$

$$= -\sum_{\beta=1}^{N_B} \Phi_\beta^N(\eta, \tau) \Phi_\beta^Q(\eta, \tau) - \Phi_L,$$

and $$\frac{dQ(\eta, \rho, \tau)}{d\eta} = \Phi(\eta, \tau) \cdot Q(\eta, \rho, \tau). \quad (78)$$

An absorption operator that accounts for diffraction effects (e.g., a diffraction operator) can be written as:

$$\Psi_{df}(\rho, \tau) \equiv \frac{i}{4}\left(1 - ib\frac{\partial}{\partial \tau}\right)\nabla_\rho^2, \quad (79)$$

with $$b \equiv \frac{1}{\omega_0 T_0}. \quad (80)$$

A Fourier transform of this operator can have the following form:

$$\Psi_{df}(\rho, \omega) \equiv \frac{i}{4}(1 - b\omega)\nabla_\rho^2, \quad (81)$$

$$\tilde{F}\left(\frac{\partial^n}{\partial \omega^n}\right) \equiv (-i\omega)^n.$$

By adding together the nonlinear and linear absorption terms, the propagation equation can be expressed in terms of the electric field as:

$$\frac{dQ(\eta, \rho, \tau)}{d\eta} = \{\Phi(\eta, \tau) + \Psi(\rho, \tau)\} \cdot Q(\eta, \rho, \tau), \quad (82)$$

This propagation equation includes complex values of $Q(\eta,\rho,\tau)$, whereas the rate equation provided in Eq. (74) can be expressed in terms of real vectors $N(\eta,\rho,\tau)$ and real values of $\overline{Q}(\eta,\rho,\tau)$.

A numerical scheme to solve the rate equation in Eq. (74) is described herein. An iteration formula that may be used to solve this equation numerically can be written as:

$$N_{n+1/2,j,i+1/2} \approx \exp\left(\delta D_0 + \sum_{\alpha=1}^{N_A} \delta D_\alpha \frac{1}{2}\{\overline{Q}^\alpha_{n,j,i} + \overline{Q}^\alpha_{n+1,j,i}\}\right) N_{n+1/2,j,i-1/2}, \quad (83)$$

where $\delta D_\alpha \equiv \Delta\tau D_\alpha$, $\alpha \in [0 \ldots N_A]$. This equation can be expressed in operator form as:

$$\overline{N}^{n+1/2}_{i+1/2} \approx e^{\Delta\tau \Upsilon^Q[n]} \overline{N}^{n+1/2}_{i-1/2}, \quad (84)$$

or $$\overline{N}^{n+1/2}_{i+1/2} \approx \exp\left(\Delta\tau\left\{\Upsilon_0 + \sum_{\alpha=1}^{N_A} \Upsilon^Q_\alpha[n]\right\}\right) \overline{N}^{n+1/2}_{i-1/2},$$

with $\overline{N}^{n+1/2}_{i+1/2} \equiv [N_{n+1/2,0,i-1/2}, \ldots, N_{n+1/2,j,i-1/2}, \ldots, N_{n+1/2,N,i-1/2}]$ and $N_{n+1/2,j,i-1/2} \equiv N(\eta_{n+1/2}, \rho_j, \tau_{i-1/2})$, where expressions for $\eta_{n+1/2}, \rho_j,$ and $\tau_{i-1/2}$ are provided in Eq. (21). The parameter $$\Upsilon^Q_\alpha[n] \equiv D_\alpha \frac{1}{2}\{\overline{Q}^\alpha_{n,j,i} + \overline{Q}^\alpha_{n+1,j,i}\}$$

may be considered as a discretization of $\Upsilon^Q_\alpha(\eta,\tau)$ and can be used in the expression for the rate operator provided in Eq. (73), with $\overline{Q}_{n,j,i} \equiv \overline{Q}(\eta_n, \rho_j, \tau_i)$, where expressions for $\eta_n$ and $\tau_i$ are provided in Eq. (22).

A general solution for the propagation equation provided in Eq. (82) can be expressed as:

$$Q(\eta + \Delta\eta) = \exp\left\{\int_\eta^{\eta+\Delta\eta}(\Phi(\eta',\tau) + \Psi(\rho,\tau))d\eta'\right\} \cdot Q(\eta) \quad (85)$$

$$= \exp\left\{\int_\eta^{\eta+\Delta\eta}\Phi(\eta',\tau)d\eta' + \Psi(\rho,\tau)\Delta\eta\right\} \cdot Q(\eta).$$

A symmetric split-step (Fourier) technique may be used to solve this propagation equation. For example, a value at a subsequent depth sample can be determined from the value at a current depth sample by first applying a diffraction operator along $\Delta\eta$ while neglecting a rate operator, and then applying the rate operator to the resulting Q value while neglecting the diffraction operator. Mathematically, this can be equivalent to a commuting of the rate and the diffraction operators, which can be expressed as:

$$Q(\eta + \Delta\eta) \approx \exp\left(\int_\eta^{\eta+\Delta\eta}\Phi(\eta',\tau)d\eta'\right) e^{\Delta\eta\Psi(\rho,\tau)} \cdot Q(\eta). \quad (86)$$

Such operators may not generally commute, and an error introduced by this approximation can be on the order of $\Delta\eta$. To decrease the computational error, a symmetric version of the split-step procedure can be used, which may be described by the following equation:

$$Q(\eta + \Delta\eta) \approx e^{\frac{\Delta\eta}{2}\Psi(\rho,\tau)} \exp\left(\int_\eta^{\eta+\Delta\eta}\Phi(\eta',\tau)dn'\right) e^{\frac{\Delta\eta}{2}\Psi(\rho,\tau)} \cdot Q(\eta). \quad (87)$$

An expression for the rate-related operator can be derived, e.g., using the following approximation:

$$\exp\left(\int_\eta^{\eta+\Delta\eta}\Phi(\eta',\tau)d\eta'\right) = \exp\left(\int_\eta^{\eta+\Delta\eta}d\eta'\left\{-\sum_{\beta=1}^{N_B}\Phi^N_\beta(\eta',\tau)\Phi^Q_\beta(\eta',\tau) - \Phi_L\right\}\right) \quad (88)$$

$$= \exp(-\Phi_L\Delta\eta)\prod_{\beta=1}^{N_B}\exp\left(\int_\eta^{\eta+\Delta\eta}\Phi^N_\beta(\eta',\tau)\Phi^Q_\beta(\eta',\tau)d\eta'\right)$$

$$\approx \exp(-\Phi_L\Delta\eta)\prod_{\beta=1}^{N_B}\exp\left(\Delta\eta\left\{\frac{\Phi^N_\beta(\eta+\Delta\eta/2,\tau-\Delta\tau/2) + \Phi^N_\beta(\eta+\Delta\eta/2,\tau-\Delta\tau/2)}{2}\right\} \times \left\{\frac{\Phi^Q_\beta(\eta+\Delta\eta,\tau) + \Phi^Q_\beta(\eta,\tau)}{2}\right\}\right).$$

Substituting the approximation for the rate operator provided in Eq. (88) into Eq. (87) can provide a form of the propagation equation which may be expressed as:

$$Q(\eta + \Delta\eta) \approx e^{\frac{\Delta\eta}{2}\Psi(\rho,\tau)}\exp(-\Delta\eta\Phi_L) \times \quad (89)$$

$$\prod_{\beta=1}^{N_B}\exp\left(\Delta\eta\left\{\frac{\Phi^N_\beta(\eta+\Delta\eta/2,\tau-\Delta\tau/2) + \Phi^N_\beta(\eta+\Delta\eta/2,\tau-\Delta\tau/2)}{2}\right\} \times\right.$$

-continued $$\left\{\frac{\Phi_\beta^Q(\eta+\Delta\eta,\tau)+\Phi_\beta^Q(\eta,\tau)}{2}\right\}e^{\frac{\Delta\eta}{2}\Psi(\rho,\tau)}\cdot Q(\eta).$$

A solution for the diffraction equation can be obtained by using a Crank-Nicholson scheme. For example, an approximation to the diffraction operator provided in Eq. (79) can be expressed as:

$$\Psi_{df}(\rho,\tau)\approx\Psi(\rho)=\frac{i}{4}\nabla_\rho^2. \quad (90)$$

Applying a differential operator $\exp(\Psi(\rho)\Delta\eta/2)\circ Q(\eta)$ can be equivalent to solving the following differential equation:

$$\frac{\partial Q(\eta,\rho)}{\partial\eta}=\frac{1}{2}\Psi(\rho)\cdot Q(\eta,\rho), \quad (91)$$

Substituting the expression for the diffraction operator provided in Eq. (90) can yield the following equation to be solved:

$$\frac{\partial Q(\eta,\rho)}{\partial\eta}=a_m\nabla_\rho^2 Q(\eta,\rho), \quad (92)$$

where $a_m \equiv \frac{1}{2}\times i/4$ and a time variable can be omitted when applying the diffraction operator. A forward difference approximation for the $\eta$ derivative can be written as $$\frac{\partial Q}{\partial\eta}=\frac{Q_j^{n+1}-Q_j^n}{\Delta\eta}. \quad (93)$$

A Crank-Nicholson scheme can be used to approximate the Laplacian operator, e.g.:

$$\nabla_\rho^2 Q(\eta,\rho)\approx\frac{1}{2}\{\nabla_\rho^2 Q(\eta+\Delta\eta,\rho)+\nabla_\rho^2 Q(\eta,\rho)\}; \quad (94)$$

$$\nabla_\rho^2 Q(\eta_n,\rho)=\left(\frac{1}{\rho}\frac{\partial}{\partial\rho}+\frac{\partial^2}{\partial\rho^2}\right)Q(\eta_n,\rho) \quad (95)$$

$$\approx\left[\frac{1}{\rho_j}\frac{Q_{j+1}^n-Q_{j-1}^n}{2\Delta\rho}+\frac{Q_{j+1}^n-2Q_j^n+Q_{j-1}^n}{\Delta\rho^2}\right].$$

Applying these operators can lead to the following iteration scheme:

$$\frac{Q_j^{n+1}-Q_j^n}{\Delta\eta}\approx\frac{a_m}{4\rho_j\Delta\rho}[Q_{j+1}^{n+1}-Q_{j-1}^{n+1}+Q_{j+1}^n-Q_{j-1}^n]+ \quad (96)$$

$$\frac{a_m}{2\Delta\rho^2}[Q_{j+1}^{n+1}-2Q_j^{n+1}+Q_{j-1}^{n+1}+Q_{j+1}^n-2Q_j^n+Q_{j-1}^n].$$

After grouping the terms containing identical (or substantially similar) Q samples, the diffraction equation can be expressed in a discrete form as:

$$u_{j-1}^j Q_{j-1}^{n+1}+u_j^j Q_j^{n+1}+u_{j+1}^j Q_{j+1}^{n+1}=v_{j-1}^j Q_{j-1}^n+v_j^j Q_j^n+v_{j+1}^j Q_{j+1}^n, \quad (97)$$

with:

$$u_{j-1}^j=\frac{a_m\Delta\eta}{2\Delta\rho}\left(\frac{1}{2\rho_j}-\frac{1}{\Delta\rho}\right); u_j^j=1+\frac{a_m\Delta\eta}{\Delta\rho^2}; \quad (98)$$

$$u_{j+1}^j=-\frac{a_m\Delta\eta}{2\Delta\rho}\left(\frac{1}{2\rho_j}+\frac{1}{\delta\rho}\right); v_{j-1}^j=-\frac{a_m\Delta\eta}{2\Delta\rho}\left(\frac{1}{2\rho_j}-\frac{1}{\Delta\rho}\right);$$

$$v_j^j=1-\frac{a_m\Delta\eta}{\Delta\rho^2}; \text{ and } v_{j+1}^j=\frac{a_m\Delta\eta}{2\Delta\rho}\left(\frac{1}{2\rho_j}-\frac{1}{\Delta\rho}\right).$$

Equations (97) and (98) may be applicable only for "internal" indices $0<\rho_j<\rho_{N_r}$, e.g., $0<\rho_1\leq\rho_j\leq\rho_{N_r-1}<\rho_{N_r}$, and boundary cases may need to be evaluated separately.

A solution to the differential equation that includes diffraction effects can be obtained at a boundary where $\rho=0$. For example, a derivative $\partial Q/\partial\rho$ can be zero at $\rho=0$ in a system having cylindrical symmetry such as, e.g., a circular pulse footprint. A limit of the expression $Q'(\rho)/\rho$ can be obtained when $\rho\to 0$ by using a Maclaurin expansion, e.g.:

$$Q'(\rho)=Q'(0)+Q''(0)\rho+o(\rho^2); \quad (99)$$

$$\frac{Q'(\rho)}{\rho}=Q''(0)+o(\rho^1)\to Q''(0), \quad (100)$$

Using Eqs. (99) and (100), the diffraction equation at $\rho=0$ can be written as $$\frac{\partial Q}{\partial\eta}=2a_m\frac{\partial^2 Q}{\partial\rho^2}. \quad (101)$$

A Crank-Nicholson technique can be applied to estimate the second derivative term for $\rho\to 0$, e.g.:

$$\frac{\partial^2 Q}{\partial\rho^2}(\eta_n,0,\tau)\approx\frac{1}{2}\left\{\frac{\partial^2 Q}{\partial\rho^2}(\eta+\Delta\eta,0,\tau)+\frac{\partial^2 Q}{\partial\rho^2}Q(\eta,0,\tau)\right\}. \quad (102)$$

A second-order approximation to the second derivative can be written as:

$$\frac{\partial^2 Q}{\partial\rho^2}(\eta_{n+1},0,\tau)\approx\frac{1}{\Delta\rho^2}\{Q_{j+1}^{n+1}-2Q_j^{n+1}+Q_{j-1}^{n+1}\}. \quad (103)$$

Using Eqs. (102) and (103), the diffraction equation at the center of a pulse can be written in an approximate form as:

$$\frac{Q_j^{n+1}-Q_j^n}{\Delta\eta}\approx\frac{2a_m}{2\Delta\rho^2}[Q_{j+1}^{n+1}-2Q_j^{n+1}+Q_{j-1}^{n+1}+Q_{j+1}^n-2Q_j^n+Q_{j-1}^n]. \quad (104)$$

The derivative of Q can be zero with respect to radial distance at $\rho=0$, because the center of the pulse can be an extreme value. For example, parameter values can be approximated at $j=-1$ as $Q_{-1}^{n+1}=Q_1^{n+1}$ and $Q_{-1}^n=Q_1^n$. Therefore the diffraction equation may be rewritten as follows:

$$\frac{Q_0^{n+1} - Q_0^n}{\Delta \eta} \approx \frac{a_m}{\Delta \rho^2} [2Q_1^{n+1} - 2Q_0^{n+1} + 2Q_1^n - 2Q_0^n]. \quad (105)$$

Eq. (105) can be used to obtain the following general equation which is applicable at a center of a pulse (e.g., at $\rho=0$):

$$u_0^0 Q_0^{n+1} + u_1^0 Q_1^{n+1} = v_0^0 Q_0^n + v_1^0 Q_1^n, \quad (106)$$

where $$u_0^0 = 1 + \frac{2a_m \Delta \eta}{\Delta \rho^2}; \; u_1^0 = -\frac{2a_m \Delta \eta}{\Delta \rho^2}; \; v_0^0 = 1 - \frac{2a_m \Delta \eta}{\Delta \rho^2}; \; \text{and} \; v_1^0 = \frac{2a_m \Delta \eta}{\Delta \rho^2}. \quad (107)$$

A solution to the diffraction equation at an outer boundary of a pulse, e.g., at $\rho=\rho_{N_r}$, can be obtained using a technique similar to that used to find a solution at the center of the pulse described herein. For example, a value at a non-existing sample point $\rho=\rho_{N_r+1}$ can be reconstructed by evaluating a linearly interpolation at values of $\rho$ near the boundary, e.g.:

$$\frac{Q_{N_r+1}^n - Q_{N_r}^n}{\Delta \rho} = \frac{Q_{N_r}^n - Q_{N_r-1}^n}{\Delta \rho}. \quad (108)$$

This linear interpolation can lead to a relationship, such as:

$$Q_{N_r+1}^n = 2Q_{N_r}^n - Q_{N_r-1}^n. \quad (109)$$

Eq. (109) can be substituted into the general diffraction equation, Eq. (97) to provide a diffraction equation having a form $$(\tilde{u}_{N_r-1}^{N_r} \tilde{u}_{N_r+1}^{N_r}) Q_{N_r-1}^{n+1} + (\tilde{u}_{N_r}^{N_r} + 2\tilde{u}_{N_r+1}^{N_r}) Q_{N_r}^{n+1} = (\tilde{v}_{N_r}^{N_r} - 1^{N_r} - \tilde{v}_{N_r}^{N_r} + 1^{N_r}) Q_{N_r-1}^n + (\tilde{v}_{N_r}^{N_r} + 2\tilde{v}_{N_r+1}^{N_r}) Q_{N_r}^n. \quad (110)$$

Eq. (110) can be expressed in a simpler form as:

$$u_{N_r-1}^{N_r} Q_{N_r-1}^{n+1} + u_{N_r}^{N_r} Q_{N_r}^{n+1} = v_{N_r-1}^{N_r} Q_{N_r-1}^n + v_{N_r}^{N_r} Q_{N_r}^n, \quad (111)$$

where $$u_{N_r-1}^{N_r} = \frac{a_m \Delta \eta}{2\Delta \rho \rho_{N_r}}; \; u_{N_r}^{N_r} = 1 - \frac{a_m \Delta \eta}{2\Delta \rho \rho_{N_r}}; \quad (112)$$

$$v_{N_r-1}^{N_r} = -\frac{a_m \Delta \eta}{2\Delta \rho \rho_{N_r}}; \; \text{and} \; v_{N_r}^{N_r} = 1 + \frac{a_m \Delta \eta}{2\Delta \rho \rho_{N_r}}.$$

Eqs. (97), (106) and (111) can be combined to provide a propagation procedure that includes diffraction effects, which can be calculated as a solution of the following linear system of equations with a tri-diagonal matrix:

$$UQ^{n+1} = VQ^n, \quad (113)$$

where $$Q^* = [Q_o^*, \ldots, Q_{j-1}^*, Q_j^*, \ldots, Q_{N_r}^*]' \quad (114)$$

and $$U = \begin{bmatrix} u_0^0 & u_1^0 & & & & & \\ u_0^1 & u_1^1 & u_2^1 & & & & \\ & u_1^2 & u_2^2 & u_3^2 & & & \\ & & & \cdots & & & \\ & & & u_{j-1}^j & u_j^j & u_{j+1}^j & \\ & & & & \cdots & & \\ & & & & & u_{N_r-1}^{N_r} & u_{N_r}^{N_r} \end{bmatrix}. \quad (115)$$

The matrix V can be expressed in a form analogous to that of the matrix U in Eq. (115). A conventional technique applicable to tri-diagonal matrix systems can be used to solve Eq. (113) such as, e.g., an LU decomposition using forward- and back-substitution for a tri-diagonal system.

A solution to a linear equation such as that in Eq. (113) can be stable, and a zero pivoting may not be required for a matrix which has a diagonal dominance at its rows. For example, a diagonal dominance condition can be expressed for a tri-diagonal matrix by the relationship as follows:

$$|u_j^j| > |u_{j-1}^j| + |u_{j+1}^j|. \quad (116)$$

In the exemplary embodiments of the present invention described herein, using the approximation $\rho_j = j\Delta\rho$, the condition provided in Eq. (116) may generally hold for the central and internal sample points, e.g.:

$$|u_{j-1}^j| + |u_{j+1}^j| = \frac{a_m \Delta \eta}{2\Delta \rho} \left( \left| \frac{1}{2j\Delta\rho} - \frac{1}{\Delta\rho} \right| + \left| \frac{1}{2j\Delta\rho} + \frac{1}{\Delta\rho} \right| \right) = \frac{a_m \Delta \eta}{\Delta \rho^2} < 1 + \frac{a_m \Delta \eta}{\Delta \rho^2} = |u_j^j|. \quad (117)$$

However, Eq. (117) can likely use a constraint on incremental delta values used because of a condition at a boundary sample point, e.g.:

$$\left| 1 - \frac{a_m \Delta \eta}{2\Delta \rho \rho_{N_r}} \right| > \frac{a_m \Delta \eta}{2\Delta \rho \rho_{N_r}}, \quad (118)$$

which may be true if, e.g.:

$$\left. \frac{a_m \Delta \eta}{2\Delta \rho \rho_{N_r}} \right|_{\rho_{N_r}=1} = \frac{a_m \Delta \eta}{2\Delta \rho} < 1, \quad (119)$$

which can provide a constraint, e.g.:

$$\frac{\Delta \eta}{\Delta \rho} < \frac{2}{a_m}. \quad (120)$$

An exemplary solution to the propagation equation provided in Eq. (89) can likely use a specification of an operator $\Phi_\beta^Q(\eta + \Delta \eta, \tau)$, which may depend on an unknown $\eta + \Delta \eta$ sample point. For example, an iteration procedure can be applied, wherein this sample point at a current iteration is drawn from results of previous iterations. A determination of a subsequent sample point value for Q can be written as:

$$Q^{n+1} \leftarrow \left( \begin{array}{c} \bar{\bar{N}}_{i+1/2}^{n+1/2(k)} \xleftarrow{\Upsilon} \bar{\bar{N}}_{i-1/2}^{n+1/2(k)} \\ Q^{n+1(k+1)} \equiv Q_{rd}^{n+1(k+1)} \xleftarrow{\Psi/2} Q_r^{n+1(k+1)} \xleftarrow{\Phi} Q_{mid}^n \end{array} \right)_{k=1 \ldots K}^{\xleftarrow{\Psi/2}} \quad (121)$$

$$Q^n (\equiv Q^{n+1(1)}).$$

According to Eqs. (83)-(84), an iteration step for the rate equation can have a form:

$$\bar{\bar{N}}_{n+1/2,i+1/2}^{(k)} \approx \exp\left(\Delta\tau \Upsilon^{\bar{Q}^{(k)}}[n]\right) \bar{\bar{N}}_{n+1/2,i-1/2}^{(k)}, \quad (122)$$

where $$\Upsilon^{\bar{Q}^{(k)}}[n] = \Upsilon_0 + \sum_{\alpha=1}^{N_A} \Upsilon_{\bar{\alpha}}^{(k)}[n], \quad (123)$$

and $$\Upsilon_{\bar{\alpha}}^{\bar{Q}^{(k)}}[n] = D_\alpha \frac{1}{2} \{\bar{Q}_{n,j,i}^\alpha + \bar{Q}_{n+1,j,i}^{(k)\alpha}\}. \quad (124)$$

The propagation equation can be evaluated by performing three determinations for each iteration: a determination of the diffraction at k=0 using Eq. (125), and two further determinations of a rate using Eq. (126) and a diffraction effect using Eq. (127). Eqs. (125)-(127) can be written as $$Q_{mid}^n = U^{-1} V Q^n, \quad (125)$$

$$Q_r^{n+1(k+1)} = \exp(-\Delta\eta\Phi_L) \prod_{\beta=1}^{N_B} \exp\left(\Delta\eta\Phi_\beta^{N^{(k)}}[n+1/2, i-1/2]\Phi_\beta^{Q^{(k)}}[n]\right) Q_{mid}^n, \quad (126)$$

and $$Q^{n+1(k+1)} \equiv Q_{rd}^{n+1(k+1)} = U^{-1} V Q_r^{n+1(k+1)}, \quad (127)$$

where the following discrete forms of propagation operators $\Phi_\beta^N(\eta,\tau)$ and $\Phi_\beta^Q(\eta,\tau)$ may be used in Eq. (126):

$$\Phi_\beta^{N^{(k)}}[n+1/2, i-1/2] \equiv \sigma_\beta \cdot \left\{ \frac{N_{n+1/2,j,i-1/2}^{(k)} + N_{n+1/2,j,i+1/2}^{(k)}}{2} \right\}, \quad (128)$$

$$\Phi_\beta^{Q^{(k)}}[n] \equiv \frac{\bar{Q}_{n,j,i}^{\beta-1} + \bar{Q}_{n+1,j,i}^{(k)\beta-1}}{2}, \quad (129)$$

and $$\Phi_L \equiv c. \quad (130)$$

A computational procedure for determining the propagation of an electromagnetic pulse in a nonlinear absorbing material which accounts for diffraction effects can be described using the following equations. Based on Eqs. (71), (83), (84), or (122)-(124), a rate equation can be used which can have the following form:

$$\bar{\bar{N}}_{n+1/2,i+1/2}^{(k)} \approx \exp\left(\Delta\tau \left\{\Upsilon_0 + \sum_{\alpha=1}^{N_A} \Upsilon_{\bar{\alpha}}^{\bar{Q}^{(k)}}[n]\right\}\right) \bar{\bar{N}}_{n+1/2,i-1/2}^{(k)} \quad (131)$$

$$= \exp\left(\iota_0 + \sum_{\alpha=1}^{N_A} \iota_\alpha \frac{\{\bar{Q}_{n,j,i}^\alpha + \bar{Q}_{n+1,j,i}^{(k)\alpha}\}}{2}\right) \bar{\bar{N}}_{n+1/2,i-1/2}^{(k)},$$

with $$\iota_0 \equiv \Delta\tau T_0 \tilde{D}_0, \text{ and } \iota_\alpha \equiv \Delta\tau T_0 \frac{\tilde{D}_\alpha}{\alpha \hbar \omega_0} (2nc_0 Q_0^2)^\alpha. \quad (132)$$

Using the results provided in Eqs. (125)-(130) above together with comments provided herein following Eq. (76), a mathematical expression to describe propagation of a pulse can be written in the following form:

$$Q^{n+1(1)} \equiv Q^n, ; Q_{mid}^n = U^{-1} V Q^n; \quad (133)$$

$$Q_r^{n+1(k+1)} = \quad (134)$$

$$\exp\left(-\sum_{\beta=1}^{N_B} \varphi_\beta \cdot \left\{\frac{N_{n+1/2,j,i-1/2}^{(k)} + N_{n+1/2,j,i+1/2}^{(k)}}{2}\right\} \left\{\frac{\bar{Q}_{n,j,i}^{\beta-1} + \bar{Q}_{n+1,j,i}^{(k)\beta-1}}{2}\right\} - \phi_L\right) Q_{mid}^n;$$

$$Q^{n+1(k+1)} \equiv Q_{rd}^{n+1(k+1)} = U^{-1} V Q_r^{n+1(k+1)}; \quad (135)$$

with $$\varphi_\beta \equiv \Delta\eta L_{df} N (2nc_0 Q_0^2)^{\beta-1} \tilde{\sigma}_\beta; \phi_L \equiv \Delta\eta \tilde{c} L_{df}; \text{ and} \quad (136)$$

By introducing a parameter $$\xi = \frac{a_m \Delta\eta}{\Delta\rho^2}$$

and by applying Eq. (98), the nonzero elements of internal rows of matrices U and V, i.e. $u_j^i$ and $v_j^i$ such that $i \in \{1, \ldots, N_r\}$ and $j \in \{i-1, \ldots, i+1\}$, may be written as:

$$u_{j-1}^j = \frac{\xi}{2}\left(\frac{1}{2j} - 1\right); \quad (137)$$

$$u_j^j = 1 + \xi; \quad (138)$$

$$u_{j+1}^j = -\frac{\xi}{2}\left(\frac{1}{2j} + 1\right); \quad (139)$$

$$v_{j-1}^j = -u_{j-1}^j; \quad (140)$$

$$v_j^j = 1 - \xi = 2 - u_j^j; \quad (141)$$

and $$v_{j+1}^j = \frac{\xi}{2}\left(\frac{1}{2j} + 1\right) = -u_{j+1}^j. \quad (142)$$

By applying Eq. (107), the nonzero elements of the first rows of matrices U and V, i.e. $u_j^i$ and $v_j^i$ such that i=0 and $j \in \{0,1\}$, may be written as:

$$u_0^0 = 1 + 2\xi; \quad (143)$$

$$u_1^0 = -2\xi; \quad (144)$$

$$v_0^0 = 1 - 2\xi = 2 - u_0^0; \quad (145)$$

and $$v_1^0 = 2\xi = -u_1^0. \quad (146)$$

By applying Eq. (112), the nonzero elements of the last rows of matrices U and V, i.e. $u_j^i$ and $v_j^i$ such that $i = N_r$ and $j \in \{N_r-1, N_r\}$, may be written as:

$$u_{N_r-1}^{N_r} = \frac{\xi}{2N_r}; \quad (147)$$

$$u_{N_r}^{N_r} = 1 - \frac{\xi}{2N_r}; \quad (148)$$

$$v_{N_r-1}^{N_r} = -\frac{\xi}{2N_r} = -u_{N_r-1}^{N_r}; \quad (149)$$

and $$v_{N_r}^{N_r} = 1 + \frac{\xi}{2N_r} = 2 - u_{N_r}^{N_r}. \quad (150)$$

Guided Waves

Conventional optical measurements may use unguided transmission of light. An optical beam may broaden in diameter over propagation distances greater than a diffraction length because of diffraction. Light may be directed over transmission distances greater than the diffraction length without incurring diffractive effects by using guided wave optics. Guided wave structures can operate by confining light within the structure using total internal reflection. This can be achieved by providing a first dielectric medium having a particular refractive index embedded within a second dielectric medium having a lower refractive index. Certain exemplary embodiments of the present invention may be used to describe optical effects of cylindrically symmetric shaped wave guides. The first dielectric medium, which may be provided in a shape of a core or inner cylinder, may be a gas, liquid, fluid, gel or solid, and it may include a multi-photon absorber. The second dielectric medium, which may be provided as a cladding or outer cylinder surrounding the core, may have a lower index of refraction than the core material.

Certain exemplary embodiments of the present invention may be used to describe a fundamental mode of such wave guides. For example, if a wave guide has a length such that a polarization of the light may not be maintained, then a polarization-preserving wave guide can be used. An effective core area can be obtained from a modal distribution $F(x,y)$ for the fundamental mode of the wave guide as described, e.g., in the Agrawal publication, e.g., $\tilde{A}_{eff} = (\int_{-\infty}^{\infty}\int_{-\infty}^{\infty} |F(x,y)|^2 dxdy)^2 / \int_{-\infty}^{\infty}\int_{-\infty}^{\infty} |F(x,y)|^4 dxdy$. Here, an intensity can be described by a function varying along $\eta$ and $\tau$ only, and may be expressed as $\tilde{I}(\eta,\tau) = 2nc_0 Q_0^2 \tilde{Q}(\eta,\tau)/\tilde{A}_{eff}$.

Energy Levels and Transitions

In certain exemplary embodiments of the present invention, a more general formulation of the exemplary computational "building blocks" shown in FIG. 1 can be used to provide information and/or data relating to interactions between electromagnetic waves and generic photoactive materials. For example, an "energy level" can refer to one or a group of energy states which can contribute, e.g., to macroscopic physical phenomena such as those described herein using mathematical models. Energy levels may apply to atoms, molecules, and/or solids. Such energy levels can include, but are not limited to, electronic, vibrational, rotational, and continuum levels of an atom, molecule, and/or solid, a conduction band, and a valence band of semiconductors and metals.

The computational "building blocks" can refer to a transition (e.g., a promotion or a relaxation) of an entity including, but not limited to, an electron or an exciton, between different energy levels. As described herein, a "generic material" can refer to a material whose energy level diagrams can be represented as union of a set of computational building blocks. A "block diagram expression" can refer to a notation for computational building blocks which may include an expression for an absorption block, e.g., ${}^m B_{s_1 s_2}^{\alpha}$, and for a relaxation block, e.g., $${}^{m_1 m_2} R_{s_1 s_2}^{type}.$$

An "energy diagram string" $\chi_{material}$ can refer to a string of one or more diagram expressions of computational building blocks which may represent the energy level diagram of a given material. An exemplary energy diagram string can be represented mathematically as $$\chi_{material} \in \left({}^m B_{s_1 s_2}^{\alpha} \vee {}^{m_1 m_2} R_{s_1 s_2}^{type}\right)^+. \quad (151)$$

where $(a \vee b)^+$ can represent a regular expression which may specify a set of textual strings having an arbitrary number of a's and b's in interchanged fashion, e.g., a, b, ab, ba, aba, abb, bbb etc.

A "q-set" ${}^m M$ can refer to a set of energy levels characterized by a common value m which may be defined by some function of a certain quantum number (e.g., a principal quantum number, a spin quantum number, an angular momentum number, etc).

The five exemplary absorption diagrams $B_0$-$B_4$ 100-140 shown in FIG. 1 can represent a reduced subset of the set of all possible computational building blocks. A detailed description for a more general set of building blocks can be provided, for example, by describing associated schematic energy diagrams, descriptive notations, and a technique for building a coupled system of rate-propagation equations based on an energy diagram string, $\chi_{material}$, which can be expressed in terms of individual building blocks as shown in Eq. (151) above.

Two types of computational building blocks can be used to describe generic materials, e.g., absorption blocks and relaxation blocks. The absorption blocks can be associated with transitions from a lower energy level to a higher one, whereas the relaxation blocks can be associated with transitions from a higher energy level to a lower one. Such building blocks can be used to describe energy level diagrams associated with a variety of photoactivated materials. They can also be used to uniquely define terms in a corresponding coupled system of rate-propagation equations which can describe interactions between, e.g., electromagnetic pulses and absorbing materials.

An energy level diagram can be used to develop a set of computational building blocks. Energy levels can be associated with, e.g., electronic states, vibrational and/or rotational electronic substates in atoms, molecules and solids, and/or bands and discrete levels in semiconductors and metals. An energy level diagram can also define possible electron and/or exciton transitions between such energy levels by describing types of transitions (e.g., radiative and/or non-radiative) and corresponding absorption cross-sections or decay time values.

An energy level diagram may be constructed using quantum calculations, e.g., calculations based on Schrödinger equations, experimental measurements, and/or hypothetical formulations, e.g., constructing a proposed diagram or adding elements to an existing diagram.

A Schrödinger equation can include all possible energy levels and/or states that a material system can be in at a particular moment in time and a particular place in space, and can describe the evolution of such material system. For example, a particle of mass M (e.g., an electron) having a potential energy $V_P(\vec{r},t)$ can be described by a wavefunction $\Psi_{SE}(\vec{r},t)$ that satisfies the following Schrödinger equation:

$$-\frac{\hbar^2}{2M}\nabla^2\Psi_{SE}(\vec{r},t) + V_P(\vec{r},t)\Psi_{SE}(\vec{r},t) = i\hbar\frac{\partial\Psi_{SE}(\vec{r},t)}{\partial t}. \quad (152)$$

Systems containing many particles, e.g., atoms, molecules, liquids or solids, can be described using more complex but similar equations as described, e.g., in B. E. A. Saleh et al., *Fundamentals of Photonics*, John Wiley & Sons, Cambridge University Press, 1991. pp. 384-591; and in C. Kittel, *Introduction to Solid State Physics*, John Wiley, New York, 1967.

The probability of locating a particle within a volume $dv$ about the position $\vec{r}$ in a time interval between t and t+dt can be written as:

$$P(\vec{r},t)dvdt = |\Psi_{SE}(\vec{r},t)|^2 dvdt. \quad (153)$$

Allowable energy levels $E^n$ of the particle can be obtained by neglecting time-varying interactions, using the following form of a wavefunction, expressed as a product of spatial and temporal terms:

$$\Psi_{SE}(\vec{r},t) = \psi(\vec{r})\exp[i(E^n/\hbar)t], \quad (154)$$

The spatial term $\psi(\vec{r})$ can be described by the following time-independent Schrödinger equation:

$$-\frac{\hbar^2}{2M}\nabla^2\psi(\vec{r}) + V_P(\vec{r})\psi(\vec{r}) = E^n\psi(\vec{r}), \quad (155)$$

and the energy levels $E^n$ can be determined as eigenvalues of the operator equation $$\hat{H}\psi(\vec{r}) = E^n\psi(\vec{r}), \quad (156)$$

where the operator $\hat{H}$ can be obtained from Eq. (155) as $$\hat{H} = -\frac{\hbar^2}{2M}\nabla^2 + V_P(\vec{r}). \quad (157)$$

The size of the energy level diagram containing most or all possible energy levels may be infinite, so that a reasonable simplification can be used to limit the number of levels contained therein. For example, the size of an energy level diagram can be reduced by including only such energy levels which may be important in describing the evolution of a particular system (or which may contribute the most to a particular physical phenomenon of interest), and/or those which may be revealed or explained by experimental measurements. Conventional energy level diagrams may be constructed in this way, and can provide an appropriate agreement between mathematical models based on such diagrams and experimental observations.

Certain materials can exhibit measured characteristics and/or behavior (e.g., optical transmittance) which may not fully agree with the existing model that can be limited to a particular set of energy levels. For example, additional energy levels may need to be added to an existing model as new experimental techniques and/or conditions are provided such as, e.g., a new laser frequency, a higher laser intensity obtained using a reduced temporal pulse width, etc. Such further hypothetical energy level diagrams can be provided based on, e.g., experience, judgment and/or comparisons with energy diagrams of similar materials. An exemplary mathematical model based on a new energy level diagram can be tested against the experimental measurements. An example of this exemplary approach is, e.g., $C_{60}$, which was originally described using an energy diagram having only low-lying singlet states to explain experimental absorption data. However, later experiments did not agree with this exemplary simple model, and an additional set of triplet states was added to the energy level diagram. Determinations based on this additional energy level diagram exhibited a better agreement with the experimental measurements.

The energy levels can be obtained as eigenvalues of the Schrödinger time-independent operator equation provided in Eq. (156). There can be an infinite number of discrete energy levels (e.g., electronic levels of an isolated atom) associated with a material based on a solution to this equation. The materials that include many atoms (e.g., molecules or crystals) can have additional energy levels associated with a certain electronic energy level. To simplify construction of an energy level diagram, a set of energy levels provided by the Schrödinger equation can be restricted to those levels required to generate reasonable agreement between calculations and experimental measurements.

Figures 11A, 11B, 11C:
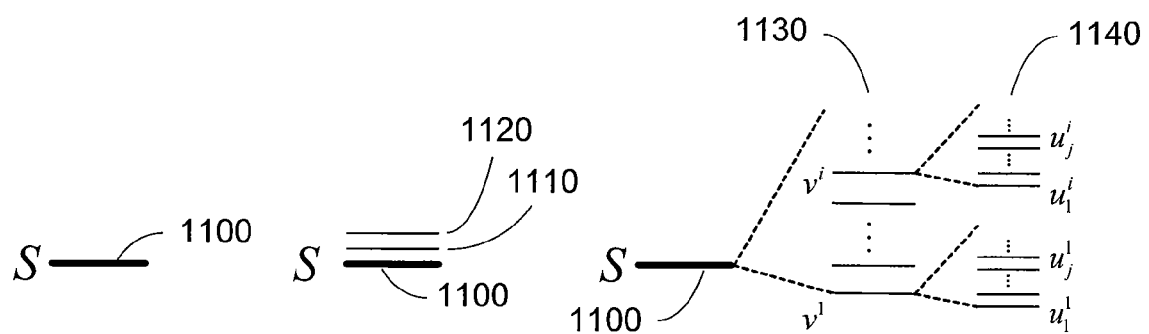
FIG. 11a is an exemplary diagram of a single energy state manifold.
FIG. 11b is an exemplary diagram of the exemplary single energy state manifold and vibrational energy levels associated with the manifold.
FIG. 11c is an exemplary diagram of the exemplary single energy state manifold, together with the vibrational energy levels and rotational energy levels associated with the manifold.

For example, FIGS. 11a-11c show exemplary energy levels which can be used in energy level diagrams. A certain vibrational and/or rotational energy levels associated with it which may be degenerate with respect to an energy level 1100 as shown in FIG. 11a. The electronic energy level 1100 can have vibrational levels 1110, 1120 associated therewith, and rotational levels may degenerate with respect to these vibrational levels, as shown in FIG. 11b. Exemplary details of the vibrational energy levels $v^i$ 1130 and rotational energy levels $u_j^i$ 1140 are shown in FIG. 11c. There may be a small difference between the vibrational and rotational energy levels 1130, 1140 as compared to an energy difference between various electronic levels 1100. The vibrational and rotational energy levels can be referred to as "sub-levels" or as a "manifold of states" associated with a particular electronic energy level or "state."

In certain exemplary embodiments of the present invention, a small, finite set of energy levels may be used to describe certain energy level diagrams. The term "energy level" can represent either an energy level $E^n$ obtained as an eigenvalue of the operator equation provided in Eq. (156), or a degenerate energy level such as the exemplary level 1100 shown in FIG. 11a. An energy level can be included in an energy level diagram, in accordance with certain exemplary embodiments of the present invention, if such energy level provides a significant contribution to a macroscopically observable physical phenomenon such as, e.g., an experimental measurement or a known absorption mechanism.

Figure 12A:
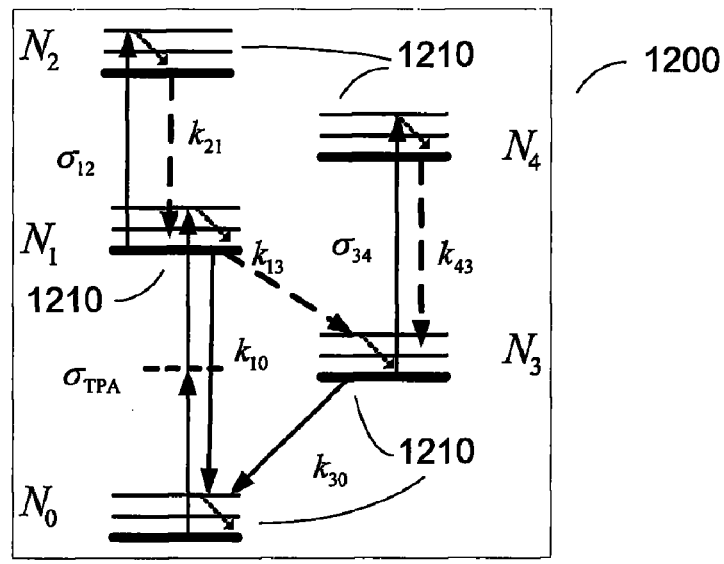
FIG. 12a is an exemplary energy level diagram associated with an exemplary nonlinear absorbing material which includes several manifolds of states, together with substates associated with the manifolds.
Figure 12B:
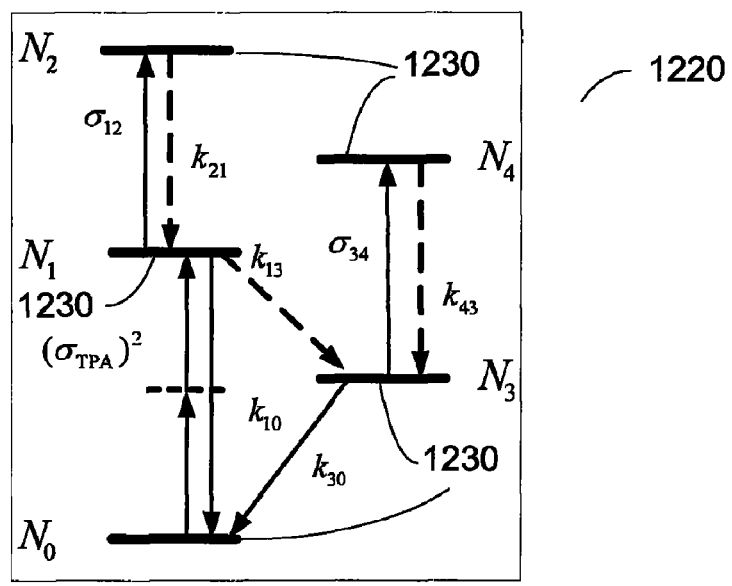
FIG. 12b is the exemplary energy level diagram shown in FIG. 12a, where each manifold may be represented by a corresponding degenerate energy level.

In many systems that include an absorbing material interacting with a laser operating in the UV to near IR spectral regions, the vibrational and/or rotational energy sublevels within a manifold of states may exhibit very short life times compared to a temporal pulse width of the laser. In such exemplary systems, electrons from higher energy substates can relax to a lowest possible substate within a manifold in a time that is much shorter than a duration of a pulse, so that the contributions of these higher energy substates to a macroscopic physical phenomena may be ignored. FIG. 12a shows an exemplary illustration of a detailed energy level diagram 1200 which includes several manifolds of states 1210. Because the substates within each manifold may have a relatively short life time, each manifold 1210 can be represented by a degenerate energy level 1230 in the corresponding energy diagram 1220 shown in FIG. 12b.

The following exemplary criteria may be used to select and/or build energy levels associated with particular materials to form an energy level diagram, which may be used in certain exemplary embodiments of the present invention:
1. levels that are reachable and/or accessible by entities energetically promoted by one or more incident photons;
2. levels that can provide a significant contribution to a macroscopic physical phenomenon, such as one indicated or suggested by experimental measurements;
3. levels which can be degenerate energy levels or combinations of degenerate levels; and
4. levels provided based on theoretical predictions.

According to the first exemplary criterion above, energy levels may be selected, which can be reached and/or accessed by entities (e.g., electrons or excitons) that may absorb incident photons. The second exemplary criterion can allow a selection, from the energy levels which may satisfy the first exemplary criterion, of a smaller number of energy levels which, when using a mathematical model, may be used to describe and/or account for macroscopic phenomena such as, e.g., measured physical absorption processes. The third exemplary criterion can allow combination of certain energy levels to form degenerate energy levels, e.g., by a combination of vibrational and/or rotational sublevels within a particular manifold of electronic states. The third exemplary criterion can also allow a combination of such degenerate levels into a further "joint" degenerate energy level. The fourth exemplary criterion can allow the building blocks to be used to expand conventional energy level diagrams or to build new energy level diagrams by introducing additional levels. This exemplary procedure can provide a more accurate description of absorption phenomena in a particular material without requiring a new algorithm or numerical method to solve a set of equations describing the expanded energy level diagram for the material. For example, when using the lasers having greater intensity and/or spectral ranges, additional terms may be added to an existing energy level diagram for a particular material to achieve consistency between the predictions and the experimental measurements.

The energy level can be classified by associating a quantum parameter with it which may stay the same during certain transitions, and can change in value during other transitions. For example, energy levels having a common value of a certain quantum parameter q can be grouped into a q-set which may be denoted by the symbol $^qM$. For example, $Q_P(N_i)$ can represent a value of a quantum parameter associated with energy level $N_i$. The q-sets corresponding to this value can be represented as:

$$^qM = \{N_i | Q_P(N_i) = q\}. \quad (158)$$

An electron spin multiplicity, which may be represented as $M_s$, is a quantum parameter which may give rise to different sets of energy levels. This exemplary parameter may be used to classify energy levels in conventional optics formulations. Such energy level classification may often be used in the optics literature. Exemplary procedures described herein for creating the energy diagrams can avoid the imposition of restrictions which may be based on energy level classification. For example, a spin multiplicity can depend on spin quantum numbers, and may be expressed as $$M_s(N_i) = 2\sum_{e \in N_i} \mathrm{spin}(e) + 1$$

for electrons e located in a common energy level $N_i$. In this exemplary classification, e.g., singlet states having a spin multiplicity $M_s = 1$ can be denoted by $^1M$, triplet states can be denoted by $^3M$, and in general:

$$^mM = \{N_i | M_s(N_i) = m\}. \quad (159)$$

An absorption block, which may be denoted by a symbol $^mB_{s_1 s_2}{}^\alpha$, can represent a mechanism that includes simultaneous absorption of α photons by an entity (e.g., an electron or an exciton) and dislocation of an entity (e.g., an electron or an exciton) from a particular energy level $N_{s_1}$ to another energy level $N_{s_2}$ within the same q-set $^mM$. Two types of photon absorption mechanisms can be distinguished. For example, a forward absorption, for which α>0, can refer to an absorption mechanism in which a photoactivated entity (e.g., an electron or an exciton) may be promoted from a lower energy level to a higher energy level. A reverse absorption can refer to an absorption mechanism in which an electron may relax from a higher energy level to a lower energy level by re-emitting one or more photons that may be coherent with the incident light. This exemplary mechanism, for which α<0, can include the phenomenon of stimulated emission.

Figure 13A:
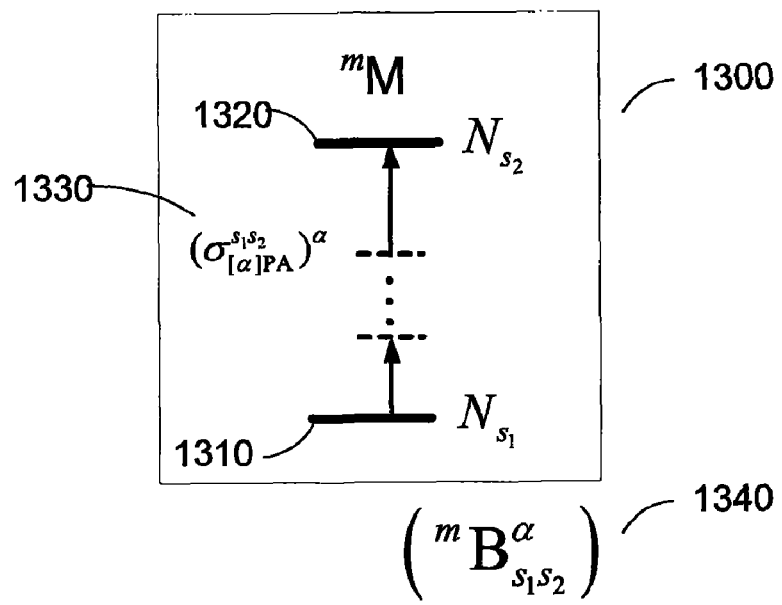
FIG. 13a is an exemplary diagram of a forward absorption block.

An exemplary schematic diagram of a forward absorption block 1300 that represents absorption of α photons is shown in FIG. 13a. This diagram shows energy levels 1310, 1320 involved in the absorption, and a molar cross section parameter $\sigma_{[\alpha]PA}{}^{s_1 s_2}$, 1330. A block diagram expression $^mB_{s_1 s_2}{}^\alpha$ 1340 which may represent the forward absorption block 1300 is also shown in FIG. 13a, and may include a q-set m associated with the states.

Figure 13B:
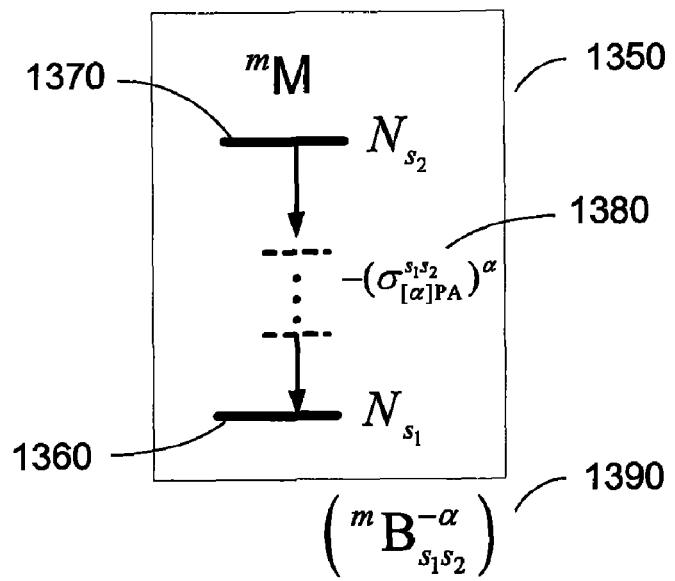
FIG. 13b is an exemplary diagram of a reverse absorption block.

An exemplary schematic diagram of a reverse absorption block 1300 that represents emission of α photons is shown in FIG. 13b. The emission can occur between two energy levels 1360, 1370, and a molar cross section parameter $-\sigma_{[\alpha]PA}{}^{s_1 s_2}$ 1380 can be associated with the reverse absorption. A block diagram expression 1390 is shown in FIG. 13b which may be used to represent the reverse absorption block. This expression 1390 is similar to the expression 1340 for a forward emission block shown in FIG. 13a, and a minus sign may be associated with the α term to indicate that the expression 1390 represents a reverse emission event.

For example, a general block diagram expression $^mB_{s_1 s_2}{}^\alpha$ 1340 shown in FIG. 13a can include indices $s_1, s_2$ which may represent certain energy levels that an electron is promoted "from" and "to" respectively (or relaxed "to" and "from" respectively if α<0). The parameter α can represent the number of photons that may be absorbed to promote, e.g., an electron from level $s_1$ to level $s_2$, where α can be negative if the expression is used to represent a reverse absorption block that includes a relaxation from level $s_2$ to level $s_1$. The parameter m can represent an index of a q-set which may include both the source level $s_1$ and the destination level $s_2$. The parameters m,α,$s_1$, and $s_2$ can be referred to as indices of the absorption block $^mB_{s_1 s_2}{}^\alpha$, whereas $\sigma_{[\alpha]PA}{}^{s_1 s_2}$ can represent a parameter of the absorption block. Optionally, the parameter $\alpha$ which may appear in a block diagram expression may be omitted if it is equal to one, e.g., $^m B_{s_1 s_2} \equiv {}^m B_{s_1 s_2}^{\ 1}$. Further, a parameter of an absorption block can be included in the corresponding block diagram expression if more clarity is desired, e.g., $^m B_{s_1 s_2}^{\ \alpha}[\sigma_{[\alpha]PA}^{s_1 s_2}]$.

The use of the computational building blocks can allow a grouping of all absorption blocks into a single group B. The elements in a group B can describe the various possible types of absorption events in generic materials. An exemplary group B may be written as:

$$B = \{{}^m B_{s_1 s_2}^{\ \alpha} | \alpha \in \{\ldots, -1, 1, 2, \ldots\}; s_1, s_2, m \in \{0, 1, 2, \ldots\}\}. \quad (160)$$

For example, the absorption blocks can be provided for a TPA chromophore AF455 using the techniques described herein. A conventional chromophore from an AFX group of TPA materials such as, e.g., AF455, may have two q-sets of electronic levels associated with it: singlet states and triplet states. An energy diagram 150 for AF455 is shown in FIG. 1 and labeled as (TPA+ESA). Electronic states 160 on the left side of the energy diagram 150 can be associated with a singlet q-set $^1 M = \{N_0, N_1, N_2\}$, and states 170 on the right side of the energy diagram 150 can be associated with a triplet q-set $^3 M = \{N_3, N_4\}$. An absorption portion of the energy diagram for AF455 can be represented as an energy level diagram string, using the computational building block notation described herein, as:

$$\chi_{AF455}|_B = {}^1 B_{01}^{\ 2} \cup {}^1 B_{12} \cup {}^3 B_{34}, \quad (161)$$

where, for example, $^1 B_{01}^{\ 2}$ can represent a simultaneous absorption of two photons and promotion of one electron from a ground level to a lowest excited level in the singlet q-set $^1 M$ 160; $\sigma_{[\alpha]PA}^{s_1 s_2}$ in the singlet q-set $^1 M$ 160 can correspond to $\sigma_{TPA}$; $^3 B_{34}$ can represent an absorption of one photon and promotion of one electron from the lowest excited state to the higher excited state in the triplet q-set $^3 M$ 170; $\sigma_{[\alpha]PA}^{s_1 s_2}$ in the triplet q-set $^3 M$ 170 can correspond to $\sigma_{34}$; and $\chi_{AF455}|_B$ can represent the energy level diagram string for AF455 using the computational building blocks that may be restricted to the set of absorption building blocks B.

A second type of the computational building block can be referred to as a relaxation block, and can be denoted by $$_{m_1 m_2} R_{s_1 s_2}^{\ type}.$$

A relaxation block can represent various types of electron, exciton and/or phonon relaxations which may occur between energy states associated with a single q-set or with different q-sets. In contrast to the reverse absorption described herein, whereas one or more photons that may be coherent with the incident light can be emitted such as in stimulated emission, the relaxation can lead to the emission of incoherent photons. For example, a relaxation block can represent an event in which an entity (e.g., an electron, exciton or phonon) may migrate from a higher energy level $N_{s_1} \in {}^{m_1} M$ to a lower energy level $N_{s_2} \in {}^{m_2} M$. This exemplary migration may be accompanied by the emission of the radiation, which can include a radiative transfer that can be represented by a wave sign '~' in the diagram expression. Alternatively, the transfer may be a non-radiative (e.g., heat) relaxation that can be represented by a bar '-' in the diagram expression. The relaxation block can include a parameter $k_{s_1 s_2}$ that may represent a relaxation decay rate.

Figure 14:
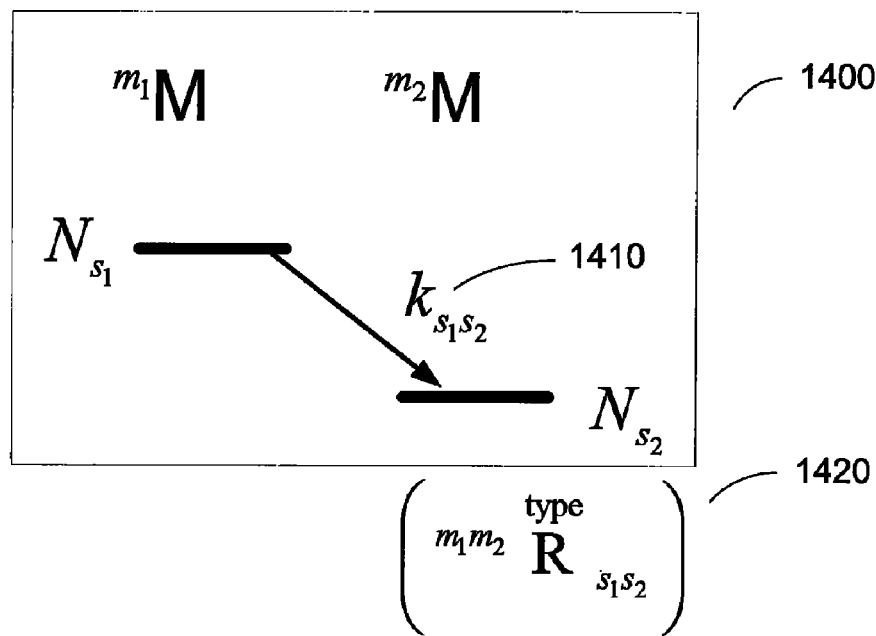
FIG. 14 is an exemplary diagram of a relaxation event and a corresponding relaxation block.

An exemplary relaxation event 1400 and a corresponding relaxation block 1410 are shown in FIG. 14. The indices in the relaxation block, $$_{m_1 m_2} R_{s_1 s_2}^{\ type},$$

include $s_1$ and $s_2$, which can represent the index of the energy level that an electron relaxes from and to, respectively. The "type" can identify a particular category of relaxation, which can include a radiative transfer ('~') or a non-radiative transfer ('-'). The type may be blank if the relaxation category is not known. Indices $m_1$ and $m_2$ can represent indices of the q-sets that include the source and destination electronic levels, respectively. Alternatively, e.g., a single index of a q-set may be provided if an electron relaxation occurs between electronic levels of a particular q-set, e.g., $$_m R_{s_1 s_2}^{\ type} \equiv {}_{mm} R_{s_1 s_2}^{\ type}.$$

Figure 15:
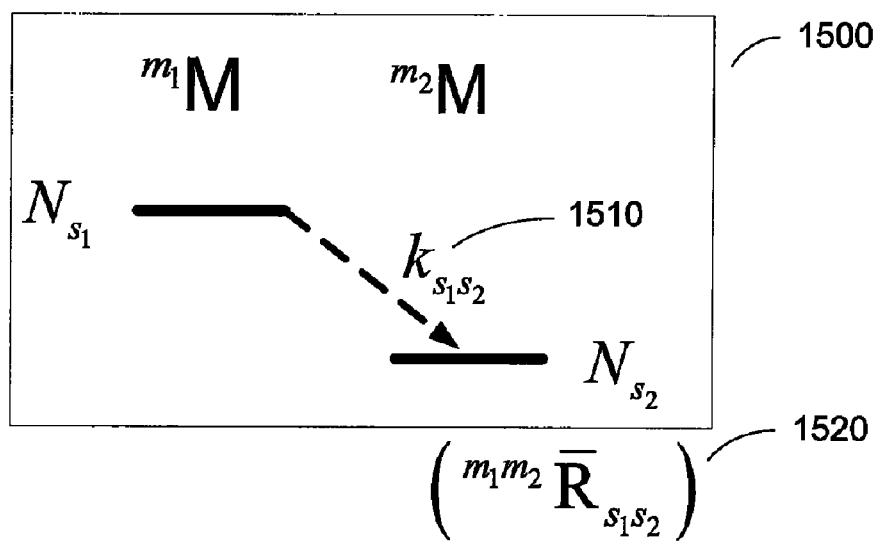
FIG. 15 is an exemplary diagram of a non-radiative migration of an electron and the corresponding relaxation block.

FIG. 15 shows an exemplary diagram 1500 of a non-radiative migration of the electron which can be associated with an intersystem crossing decay rate $k_{s_1 s_2}$ 1510. This exemplary relaxation diagram can be represented by the relaxation block $_{m_1 m_2} \overline{R}_{s_1 s_2}$ 1520.

Figure 16:
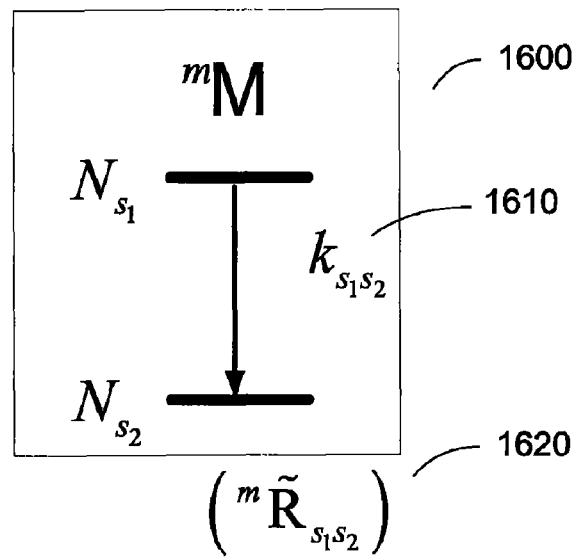
FIG. 16 is an exemplary diagram of a radiative migration of the electron and the corresponding relaxation block.

FIG. 16 shows an exemplary diagram 1600 of a radiative migration of the electron which can be associated with the intersystem crossing decay rate $k_{s_1 s_2}$ 1610. This exemplary relaxation diagram can be represented by the relaxation block $^m \tilde{R}_{s_1 s_2}$ 1620 which may correspond, e.g., to a fluorescence emission during migration of an electron along states having a common spin multiplicity m.

A group of most or all possible relaxation building blocks associated with a particular material can be grouped into a set R of relaxation blocks, which may be expressed as:

$$R = \left\{ {}_{m_1 m_2} R_{s_1 s_2}^{\ type} \middle| \text{type} \in \{'\sim', '-', '\,'\}; s_1, s_2, m_1, m_2 \in \{0, 1, 2, \ldots\} \right\}. \quad (162)$$

Figure 17:
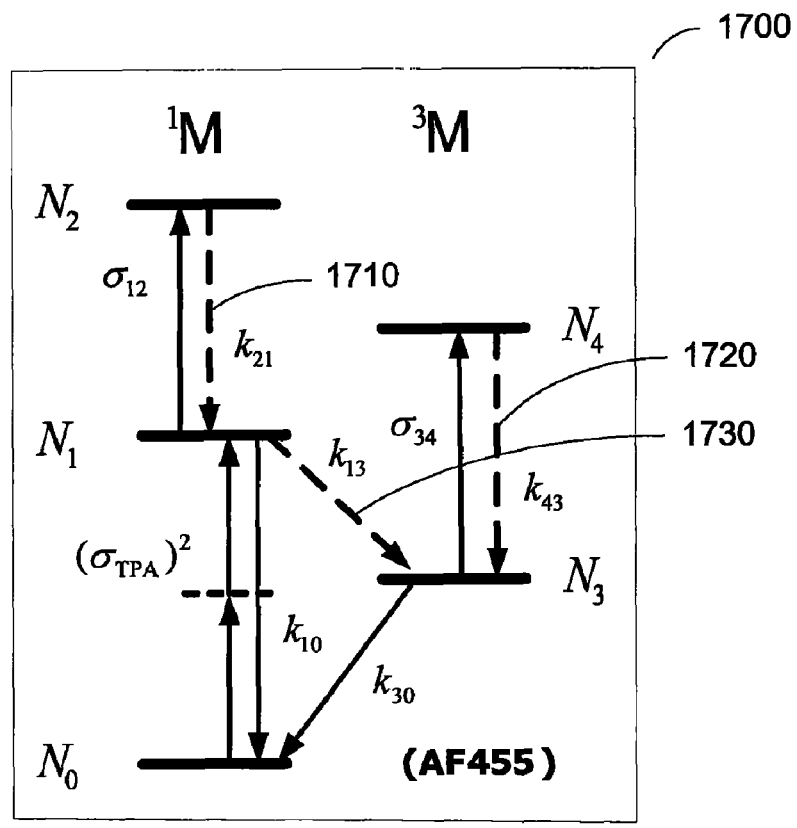
FIG. 17 is an exemplary energy diagram that is used to represent various exemplary energy level transitions associated with AF455.

An exemplary energy diagram 1700 that can represent various energy level transitions associated with AF455 is shown in FIG. 17. This diagram 1700 includes relaxation links 1710-1730. A relaxation portion of the energy diagram string that can be used to describe AF455 can be written as:

$$\chi_{AF455}|_R = {}^1 \tilde{R}_{10} \cup {}^1 R_{21} \cup {}^3 R_{43} \cup {}^{13} \overline{R}_{13} \cup {}^{31} \tilde{R}_{30}. \quad (163)$$

Eq. (163) can be combined with Eq. (161) to provide a complete diagram string $\chi_{AF455}$, which can be written as:

$$\chi_{AF455} = {}^1 B_{01}^{\ 2} \cup {}^1 B_{12} \cup {}^3 B_{34} \cup {}^1 \tilde{R}_{10} \cup {}^1 R_{21} \cup {}^3 R_{43} \cup {}^{13} \overline{R}_{13} \cup {}^{31} \tilde{R}_{30}. \quad (164)$$

Another exemplary material that can behave as a nonlinear absorber is, e.g., a CuTPPS chromophore contained within a gel host. For example, CuTPPS entrapped within an aluminosilicate host is described, e.g., in X. D. Sun et al., "Nonlinear Effects in Chromophore Doped Sol-Gel Photonic Materials", J. Sol-gel Sci. Technol., 9, 169-181, (1997). This exemplary nonlinear material can have six energy levels and three or more q-sets. Such material can absorb light at 584 nm and may exhibit up-converted photon emission at 434 nm provided by a relaxation links.

Figure 18:
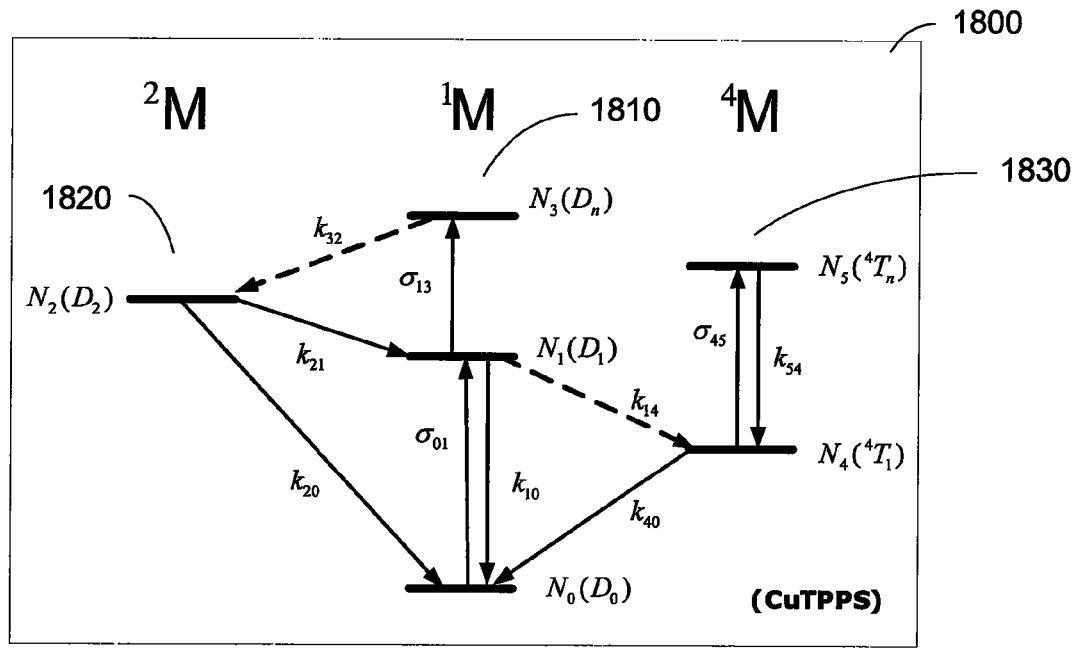
FIG. 18 is an exemplary energy diagram used to represent the various exemplary energy level transitions associated with CuTPPS.

An exemplary energy diagram 1800 that can represent various energy level transitions associated with CuTPPS is shown in FIG. 18. The energy levels of CuTPPS can be $N_0, N_1, N_2, N_3, N_4, N_5$. These energy levels may be grouped into three q-sets, as shown in FIG. 18: $^1M=\{N_0,N_1,N_3\}$ 1810, $^2M=\{N_2\}$ 1820, and $^4M=\{N_4,N_5\}$ 1830. Based on these q-sets, the energy diagram string for CuTPPS can be expressed as:

$$\chi_{CuTPPS} = {}^1B_{01} \cup {}^1B_{13} \cup {}^4B_{45} \cup {}^1\tilde{R}_{10} \cup {}^{12}\overline{R}_{32} \cup {}^{14}\overline{R}_{14} \cup {}^{21}\tilde{R}_{21} \cup {}^2\tilde{R}_{20} \cup {}^4\tilde{R}_{54} \cup {}^{41}\tilde{R}_{40}. \quad (165)$$

Figure 19:
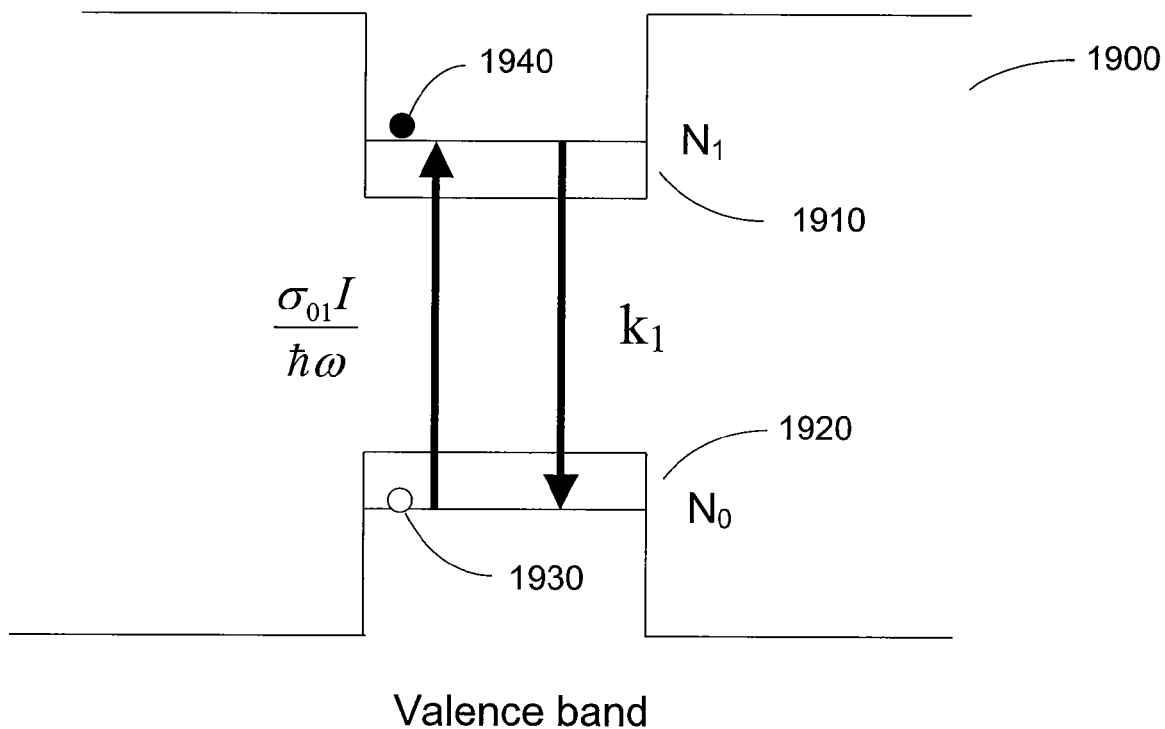
FIG. 19 is an exemplary schematic diagram of photoexcitation and relaxation of an electron creating an exciton in a semiconductor.

A further example of generation of an energy level string can be provided for a semiconductor quantum dot using the exemplary procedures described herein. For example, an exemplary diagram 1900 of photoexcitation of an exciton in a semiconductor is shown in FIG. 19 and described, e.g., in B. E. A. Saleh et al., *Fundamentals of Photonics*, John Wiley & Sons, Cambridge University Press, 1991, pp. 384-591. In this exemplary material system, an exciton recombination can provide both a stimulated and a spontaneous emission. A ratio of electron degeneracy between level 1 1910 and level 0 1920 can be a unity in this exemplary analysis. As shown in FIG. 19, an open circle 1930 can represent an electron "hole", and a solid black circle 1940 can represent an electron. The exciton can include the electron-hole pair 1930, 1940.

A coupled set of rate-propagation equations can be used to describe propagation of an electric field through a semiconductor quantum dot. This set of equations may be written as:

$$\begin{cases} \dfrac{dN_0}{d\tau} = -\dfrac{\sigma_{01} I}{\hbar \omega_0}(N_0 - N_1) + k_{10} N_1 \\ \dfrac{dN_1}{d\tau} = \dfrac{\sigma_{01} I}{\hbar \omega_0}(N_0 - N_1) - k_{10} N_1 \end{cases}, \quad (166)$$

and $$\frac{dI}{d\eta} = -\sigma_{01} I (N_1 - N_0), \quad (167)$$

Figure 20:
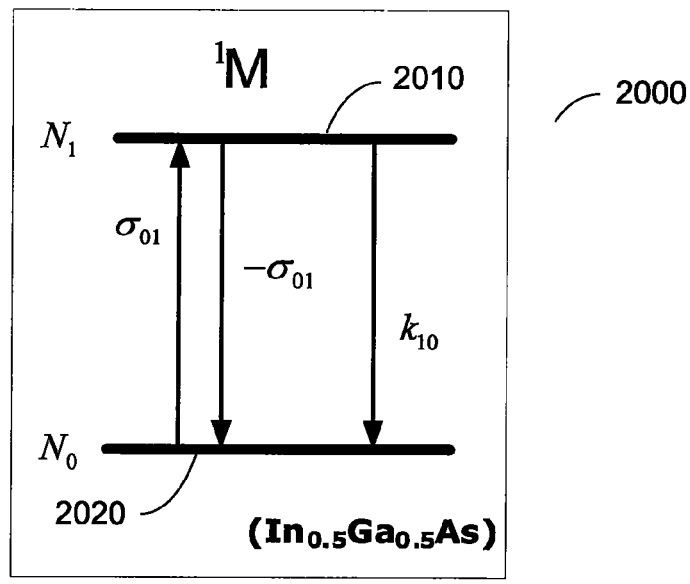
FIG. 20 is an exemplary energy diagram used to represent the various exemplary energy level transitions associated with a semiconductor quantum dot.

An energy level diagram 2000 which can be used to describe the quantum dot illustrated in FIG. 19, which may be based on Eqs. (166) and (167) is shown in FIG. 20. This energy level diagram that may be used to describe absorption and emission by a quantum dot can include three basic blocks and two energy levels 2010, 2020 associated with a single same q-set. The energy levels are $^1M=\{N_0,N_1\}$, and the energy level string $\chi_{InGaAs}$ can be written as:

$$\chi_{semiconductor} = {}^1B_{01} \cup {}^1B_{01}{}^{-1} \cup {}^1R_{10}, \quad (168)$$

where $^1B_{01}{}^{-1}$ can represent an exemplary absorption block that can be associated with inverse absorption.

Each computational building block in the set B∪R (which includes both absorption and relaxation blocks) can define a unique corresponding term in the coupled system of rate-propagation equations provided in Eqs. (15) and (16), which may be used to describe propagation of an electric field through a sample of a photoactive material. The computational building blocks described herein may be analogous or similar to computational molecules that can be used to formulate multidimensional finite difference numerical schemes.

A particular energy diagram string associated with a photoactivated material mat can include a component e in it, such that $\chi_{mat}$ can be written in a form $\chi_{mat} = \ldots \cup e \cup \ldots$ . The component e can represent one of the types of computational building blocks described herein, e.g., the absorption building block or the relaxation building block. Each type of the computational building block can provide certain terms in a matrix $\hat{D}_\alpha$ and a vector $\sigma_\beta$ which appear in the rate and propagation equations provided in Eqs. (15) and (16).

For example, e can represent an absorption building block, $e = {}^m B_{s_1 s_2}{}^\alpha$, which may be associated with an absorption parameter $\sigma_{[\alpha]PA}{}^{s_1 s_2}$. The value of this parameter can be included at corresponding places in the matrix $\hat{D}_\alpha$ and vector $\sigma_\beta$, which can lead to the following expressions:

$$\hat{D}_\alpha[s_1,s_2] = \hat{D}_\alpha[s_1,s_2] - sgn(\sigma_{[\alpha]PA}{}^{s_1 s_2}) \sigma_{[\alpha]PA}{}^{s_1 s_2}, \quad (169)$$

$$\hat{D}_\alpha[s_2,s_1] = \hat{D}_\alpha[s_2,s_1] + sgn(\sigma_{[\alpha]PA}{}^{s_1 s_2}) \sigma_{[\alpha]PA}{}^{s_1 s_2}, \quad (170)$$

and $$\sigma_\alpha[s_1] = \sigma_\alpha[s_1] + sgn(\sigma_{[\alpha]PA}{}^{s_1 s_2}) \sigma_{[\alpha]PA}{}^{s_1 s_2}. \quad (171)$$

Alternatively, e can represent a relaxation building block, $$e = {}^{m_1 m_2} \overset{t}{R}_{s_1 s_2},$$

which may be associated with a decay rate $k_{s_1 s_2}$. The value of this decay rate can be included in the matrix $\hat{D}_0$ to yield the following expressions:

$$\hat{D}_0[s_1,s_2] = \hat{D}_0[s_1,s_2] - k_{s_1 s_2}, \quad (172)$$

and $$\hat{D}_0[s_2,s_1] = \hat{D}_0[s_2,s_1] + k_{s_1 s_2}. \quad (173)$$

The matrices $\hat{D}_0$, $\hat{D}_\alpha$ and the vector $\sigma_\beta$ which appear in the rate and propagation equations provided in Eqs. (15) and (16) may be constructed for a particular material using the following procedure. For example, each matrix $\hat{D}_0$, $\hat{D}_\alpha$ and the vector $\sigma_\beta$ may be defined initially to have all elements equal to zero. The energy diagram string $\chi_{mat}$ for a given photoactive material can be obtained, e.g., using the exemplary procedures described herein. Each computational building block appearing in $\chi_{mat}$ can then be used to modify certain elements in the matrices $\hat{D}_0$, $\hat{D}_\alpha$ and the vector $\sigma_\beta$. For example, Eqs. (169)-(171) can be applied for each absorption block that appears in the energy diagram string, and Eqs. (172) and (173) can be applied for each relaxation block. This exemplary procedure can be repeated until all component e in the energy diagram string (e.g., all absorption and relaxation blocks) have been used to modify appropriate elements in the matrices $\hat{D}_0$, $\hat{D}_\alpha$ and the vector $\sigma_\beta$ using Eqs. (169)-(173). The resulting matrices and vector may be provided in Eqs. (15) and (16), and these exemplary equations may be solved using exemplary procedures described herein to determine the absorption behavior of the particular material.

Certain restrictions may be applied when identifying and/or providing computational building blocks associated with a particular photoactive absorbing material. For example, each energy level, excluding three special states $N_0$, $N_V$, and $N_e$, can be associated with a unique group of states, e.g., a q-set. For a particular material, all such q-sets $^mM$ may be identified by an expression which can be written as $M=\{^mM | m=m_1, \ldots, m_{M_M}\}$.

For example, $N_0$ can represent a ground state and it may belong to more then one q-set. This condition can be written as:

$$N_0 \in {}^m M, \forall m \in \{j_1, \ldots, j_{M_0}\} \subseteq \{m_1, \ldots, m_{M_M}\}. \quad (174)$$

$N_V$ can represent a valence band, which may be present in all q-sets. This condition may be expressed mathematically as:

$$N_r \in {}^m M, \forall m \in \{m_1, \ldots, m_{M_M}\}. \quad (175)$$

$N_e$ can represent a conduction band, which may also be present in all q-sets, e.g.:

$$N_e \in {}^m M, \forall m \in \{m_1, \ldots, m_{M_M}\}. \quad (176)$$

Each absorption building block ${}^m B_{s_1 s_2}{}^\alpha$ identified or proposed for a particular material can be subjected to certain exemplary constraints. These constraints can include, e.g.: $[s_1, s_2, m] \in \Box_0{}^3$; $\alpha \in \Box \backslash \{0\}$ with $m \in \{m_1, \ldots, m_{M_M}\}$; $s_2 \neq 0$; $N_{s_1} \neq N_e$; and $N_{s_2} \neq N_V$. These constraints can assist to provide consistent building block formulations for describing the absorption behavior of the nonlinear materials in accordance with certain exemplary embodiments of the present invention.

In a similar manner, each relaxation building block $${}^{m_1 m_2} R_{s_1 s_2}^t$$

identified or proposed for a particular material can also be subjected to certain exemplary constraints. For example, such constraints on relaxation building blocks can include: $[s_1, s_2, m_1, m_2] \in \Box_0{}^4$, $m \in \{m_1, \ldots, m_{M_M}\}$; $(m_1, m_2) \in \{m_1, \ldots, m_{M_M}\}^2$; $s_1 \neq 0$; $N_{s_2} \neq N_e$; and $N_{s_1} \neq N_V$.

In certain exemplary embodiments of the present invention, steady-state solutions of the rate and propagation equations described herein may provide an approximation of population density dynamics. Such exemplary solution can correspond to a solution of a nonlinear system of rate equations for population densities in which the right-hand sight of the equations are set equal to zero, e.g., $\partial N/\partial t = 0$. Update procedures provided in Eqs. (169), (170), (172) and (173) may be omitted when obtaining such steady-state approximate solutions.

Exemplary Computational Procedures

Figure 21:
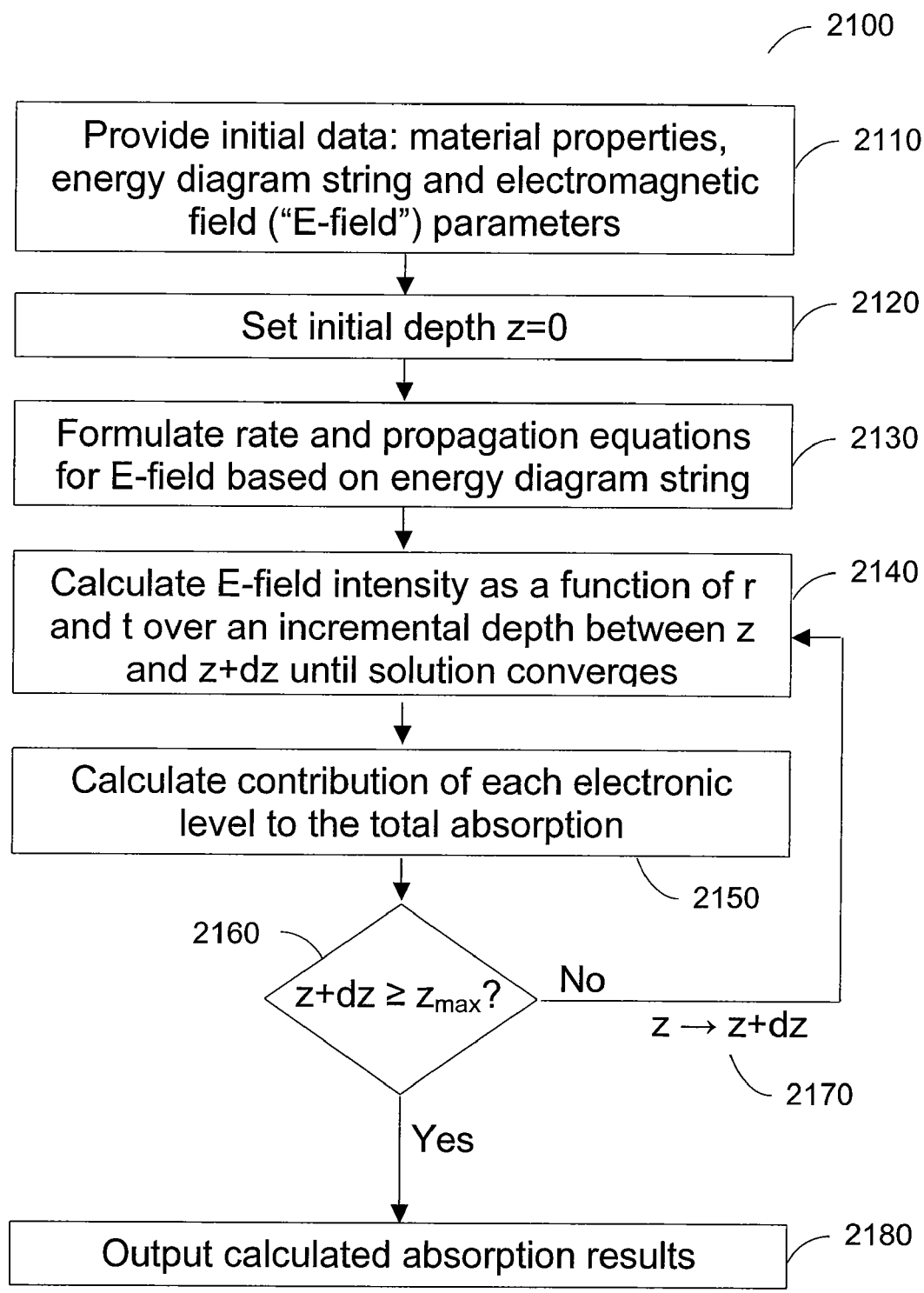
FIG. 21 is a general flow diagram of an exemplary embodiment of a method according to the present invention.

An exemplary flow diagram of a method 2100 according to certain exemplary embodiments of the present invention is shown in FIG. 21. For example, initial data may be provided for the determination of an interaction between, e.g., an electromagnetic wave and a nonlinear absorbing material (step 2110). Such data can include, for example, an identification of the absorbing material together with material properties, which may include an energy level diagram or an energy diagram string. The initial data may also include properties of the coherent electromagnetic wave which may be, e.g., one or more laser pulses, etc. Properties of the coherent electromagnetic wave can include a wavelength or a plurality of wavelengths, pulse duration and/or number, interval between a plurality of pulses, intensity, fluence, radius or diameter of a collimated or focused beam at an incident surface of the absorbing material, etc. Numerical parameters may also be provided and can include, e.g., temporal and/or spatial resolution and/or extent of numerical determinations to be performed.

After initial parameters can be established (step 2110), an initial depth z within the material can be initialized to a value of 0 (step 2120). This can correspond to the incident coherent electromagnetic wave first contacting an outer surface of the absorbing material. Propagation and rate equations such as, e.g., Eqs. (15) and (16) can be formulated based on the parameters such as the energy level diagram or an energy diagram string associated with the absorbing material using procedures such as, e.g., those described herein (step 2130).

An intensity of the coherent electromagnetic wave or laser pulse(s) can then be determined as a function of time t and, optionally, radial distance r from the center of the incident wave at a depth between z and z+dz (step 2140). The determinations intensity values can be based at least in part on intensity values determined at a depth z, which can be initially set equal to 0 (step 2120), e.g., at the material surface. The parameter dz can represent an incremental depth interval used in the exemplary computational techniques described herein. The determination of intensity as a function of r and t may be performed using several iterations of the rate and propagation equations to obtain convergent and/or consistent values at a depth interval between z and z+dz. After the intensity is obtained at the depth z, contributions of each energy level in the material to absorption within that depth interval can optionally be determined (step 2150).

If the depth z is greater than or equal to a maximum depth $z_{max}$ of interest (step 2160), the absorption results can be provided to, e.g., a database, data file and/or a display arrangement (step 2180). The maximum depth $z_{max}$ can be, e.g., a sample thickness of the absorbing material. The absorption results can include, e.g., electric field, intensity, energy level populations and/or contributions of individual levels to absorption. These exemplary results can be provided as a function of depth within the absorbing material, time and optionally radial distance from a center of the incident wave.

If the depth z is less than the maximum depth $z_{max}$ of interest (step 2160), the current depth can be incremented by an amount dz (step 2170). The electric field intensity can then be determined at a depth interval between the new depth z and z+dz (step 2140) and the absorption contributions by individual electronic levels within this new depth interval can also be determined (step 2150). This exemplary procedure can be repeated at increasing depths until the maximum depth $z_{max}$ is reached (step 2160).

Figure 22A:
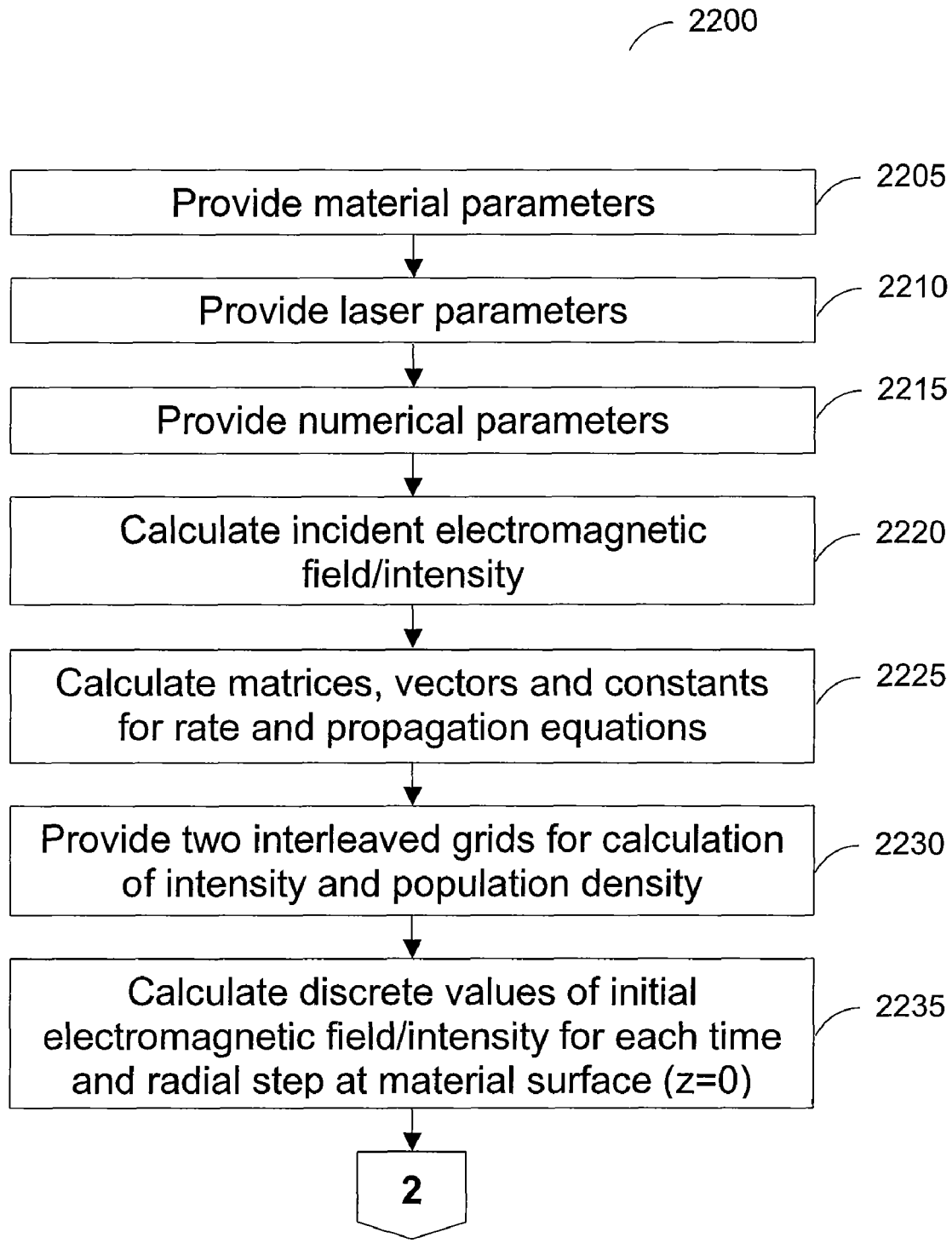
FIG. 22a is an illustrative portions of a detailed flow diagram of an exemplary embodiment of a method according to the present invention.
Figure 22B:
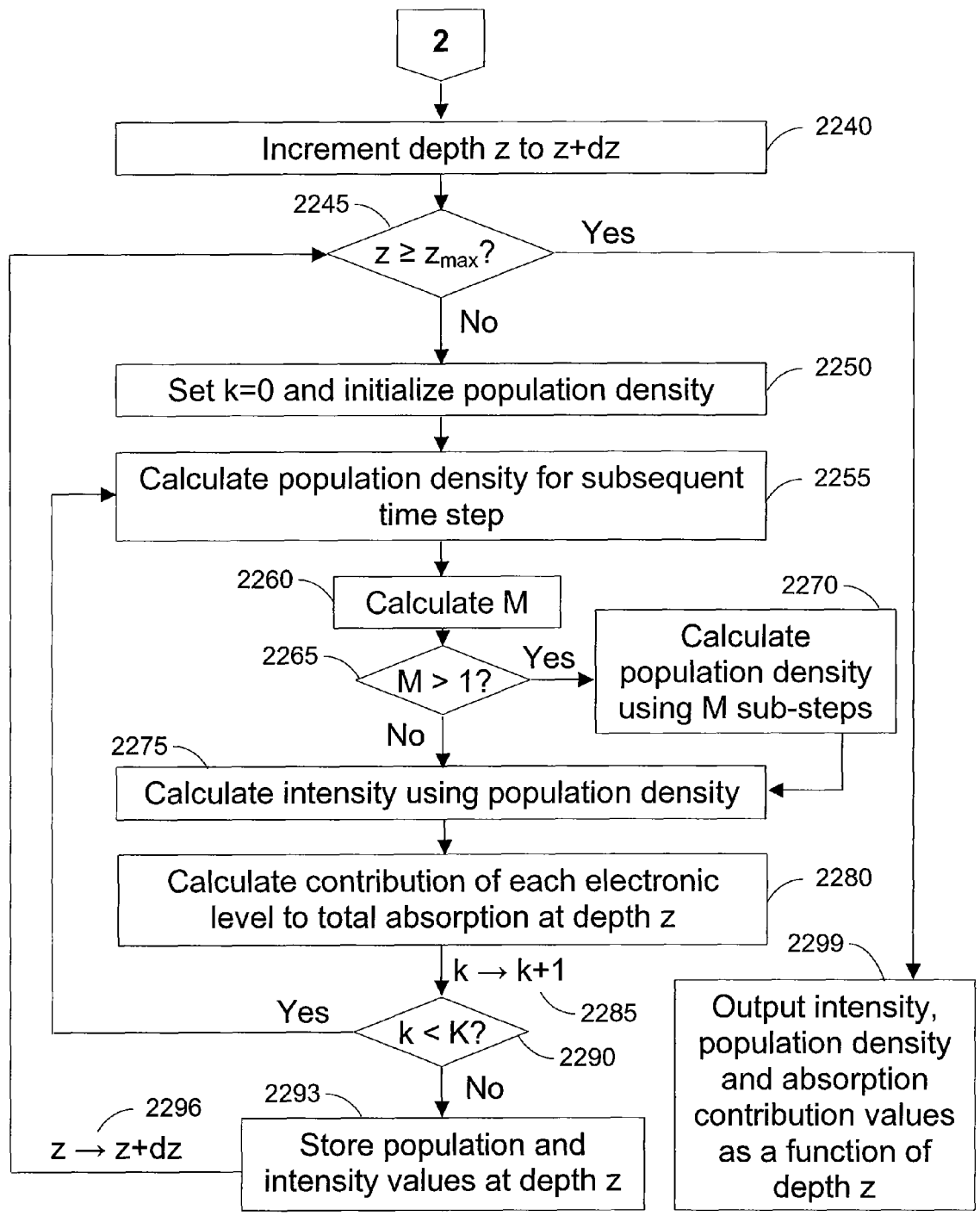
FIG. 22b is a further illustrative portion of a detailed flow diagram of an exemplary embodiment of a method according to the present invention.

A detailed exemplary flow diagram of a method 2200 according to particular exemplary embodiments of the present invention is shown in FIGS. 22a-22b. For example, the material parameters associated with a nonlinear absorbing material of interest may be provided (step 2205). Such material parameters can include, for example, a sample thickness (which may be set equal to the maximum depth of interest, $z_{max}$) and/or an index of refraction. The material parameters can also include a concentration of light-activated atoms, molecules and/or radiators in gas, liquid or solid. Further material parameters that may be provided include, e.g., cross sections for single- and/or multi-photon absorptions, a linear absorption coefficient, and/or decay rates for energy levels associated with the material. Certain material parameters may be optionally provided in a form of one or more absorption blocks and/or relaxation blocks, and/or an energy diagram string.

Parameters associated with an incident laser pulse or pulses, or with another form of incident electromagnetic wave, may also be provided (step 2210). Such parameters can include, e.g., one or more central wavelengths or a carrier frequency, a temporal pulse width (e.g., a pulse duration), a beam radius or diameter or other physical dimension associated with the incident pulse or wave, and optionally an incident pulse function if the pulse intensity is not uniform over its cross-sectional area and/or over its temporal functional shape. If the laser or coherent electromagnetic wave is provided, e.g., as a plurality of incident pulses, such parameters can be provided for each pulse. Further parameters can include, e.g., a number of pulses and a temporal interval between successive pulses.

Numerical parameters which can be used to obtain a solution to the appropriate absorption equations may also be provided (step 2215). These numerical parameters may include, e.g., a time step or temporal resolution dt, a depth interval dz, and/or a radial distance increment dr. Other numerical parameters that may be provided include a number of iterations K and/or a sub-sampling threshold value $\epsilon$, which are described herein.

An intensity of the incident electromagnetic wave (e.g., a laser pulse) can be determined (step 2220) using, for example, provided electromagnetic wave parameters (step 2210).

Matrices, vectors and constants associated with propagation and rate equations may then be formulated (step 2225), and can be based at least in part on material parameters such as, e.g., an energy level diagram or an energy diagram string associated with the absorbing material. The rate equation may have a form as provided, e.g., in Eqs. (15), (72) or (74). The propagation equation may have a form as provided, e.g., in Eqs. (16), (76) or (82). The matrices, vectors and/or constants may be formulated, for example, using exemplary procedures such as those provided in Eqs. (169)-(173).

Computational grids may then be provided for solving the rate and propagation equations numerically (step 2230). These grids may have a form, e.g, such as provided in Eq. (21) which may be used to solve the population density equation, and Eq. (22) may be used to solve the intensity or electric field propagation equation. The size scale of these can be based at least in part on the provided numerical parameters (step 2215), and they can be related to, e.g., a spatial and/or a temporal resolution at which the intensity and/or population densities may be determined.

Discrete values of the intensity or electric field of the incident coherent electromagnetic wave (e.g., a laser pulse) can be determined at a first surface of the material (e.g., z=0) (step 2235) using, for example, provided numerical parameters (step 2215) and a provided incident intensity of the electromagnetic wave (step 2220). The incident intensity or electric field may be determined as a function of time and/or location at certain points on the provided grids (step 2230). An initial spatial distribution of intensity or electric field at entrance of the material sample may be expressed in terms of, e.g., a radial distance from a center of a pulse, polar coordinates, rectangular coordinates, etc., and such spatial distribution may further be provided at various times. An initial spatial and/or temporal distribution of intensity or electric field at an initial surface of the material sample may be obtained from experimental measurements, or by applying analytic or numerical calculations of various optical configurations which may be present outside of the surface of the material. Such measurements or calculations can be converted into discrete values and used as initial beam or field parameters in certain exemplary embodiments of the present invention.

An incremental depth dz may be added to a current depth z within the material (step 2240). The total depth z+dz can then be compared to a maximum depth, e.g., $z_{max}$ (step 2245), and if z+dz is greater than or equal to $z_{max}$ then various determined absorption values associated with interactions between the material and the coherent electromagnetic wave can be provided, e.g., to an output device or storage medium (step 2299). The distance $z_{max}$ can correspond to a sample thickness or to some other depth at which it may be provided that interactions in the material are not calculated further.

Absorption interactions, which may include changes in intensity of the coherent electromagnetic wave and/or population densities of energy levels within the material, can be determined within a portion of the material that lies between the depths z and z+dz. The parameter k, which can represent a number of iterations to be performed within the portion of material between z and z+dz, may be set equal to zero initially and vectors $N_{-1/2,j}^{n+1/2}[k]$ can be initialized to unit vectors (step 2250). Such vectors can be associated, for example, with population densities of electronic levels within the portion of the material.

The population densities can then be updated to new values which may be present after a subsequent time procedure has elapsed (step 2255) using, e.g., Eq. (29), (83), (84), (131) or (132). A parameter M which may be related to the time step can then be determined (step 2260). If M is greater than 1 (step 2265), then population density changes over the time step may be redetermined using a refined set of sub-steps (step 2270). This determination can be performed, e.g., using Eq. (42).

When the population densities are determined over the time step, the intensity distribution of the coherent electromagnetic wave can be modified based on the new population densities (step 2275) using, e.g., Eq. (30), (133)-(136). Optionally, a contribution of each electronic level in the material to the total absorption within the portion of the material between z and z+dz may also be determined (step 2280). These contributions may be calculated, e.g., using Eqs. (48)-(52), or (54).

The parameter k can then be increased by 1 (step 2285), and compared to a further parameter K (step 2290). K can represent, for example, a preselected number of computational iterations to be performed at a particular depth interval within the material, e.g., between z and z+dz. If k is less than K (step 2290), then another iteration can be performed to update values of the population densities (step 2255) and intensity distribution (step 2275) over the depth interval. If k is greater than or equal to K (step 2290), then the preselected number of computational iterations may have been performed over the depth interval between z and z+dz. The current determined values of population densities (step 2255), intensity distribution (step 2275), and energy level contributions to the total absorption (step 2280) associated with the depth interval between z and z+dz in the material may then be stored (step 2293). These values may be stored, e.g., by writing them to a computer-readable medium, printing them, providing them to a data analysis program and/or displaying them on a screen.

The depth z may then be increased by an amount dz (step 2296), and the new depth z may then be compared to a maximum depth, e.g., $z_{max}$ (step 2245). If z+dz is greater than or equal to $z_{max}$ then various absorption values and population densities associated with interactions between the material and the coherent electromagnetic wave may have been calculated throughout the region of interest in the material, and these values can be can be provided, e.g., to an output device or storage medium (step 2299).

The interaction between a nonlinear absorbing material and an coherent electromagnetic wave such as, e.g., a laser pulse, which may be determined using exemplary embodiments of the present invention, can optionally be compared to experimental measurements of such interactions. Such comparisons are shown, e.g., in FIGS. 2a-2c. If agreement between certain determined and experimental values associated with the interaction are not sufficiently close for a particular purpose, material parameters used in certain exemplary embodiments of the present invention may be modified to provide better agreement. Such parameters can be provided, e.g., in step 2110 of FIG. 21 and step 2205 of FIG. 22a. The material parameters may be modified by changing certain characteristics of an energy level diagram and/or one or more relaxation and/or absorption blocks associated with the material or, alternatively, adding additional energy levels and/or relaxation and/or absorption blocks to the existing material parameters. Such modifications may be made, e.g., based on physical models, expected improvements in agreement between the determinations and experiments, etc.

The results of the exemplary computational procedures shown in FIGS. 21, 22a and 22b, which may include a radial or other spatial dependence of the calculated values, can be compared to results obtained using conventional techniques which may assume a radially constant solutions. Such a comparison can provide information relating to whether a local peak intensity may exceed a critical value for a material and cause damage. Such localized values may not be provided by conventional techniques. Thus exemplary embodiments of the present invention may be used to provide more reliable prediction of damage in absorbing materials which may be caused by interactions with, e.g., one or more incident laser pulses.

In certain exemplary embodiments of the present invention, an absorbing material may include a plurality of layers, where two or more layers may each be associated with a different set of material properties. Each layer w may also have a particular thickness $z_w$ associated with it. To determine the absorption interactions in such multilayered absorbing materials, an exemplary method such as that shown in FIGS. 21, 22a and/or 22b can be used with respect to an upper layer that is first contacted by an incident coherent electromagnetic wave (e.g., w=1). This exemplary procedure may be applied throughout the first layer, e.g., until a depth of $z_1$ is reached, at which point a second layer (e.g., w=2) which may be formed of a different material may be present. An intensity or electric field distribution can thus be determined at a depth $z_1$, which can be based on interactions within the first layer. This distribution can be used as an initial condition to determine interactions within the second layer where the depth used in the determinations can range, e.g., from $z_1$ to $z_2$. Material properties associated with the second layer may be used in this second set of determinations. This exemplary procedure may be continued for additional layers, if present, to provide information relating to interactions between an coherent electromagnetic wave and a multilayered absorbing material. Optionally, reflection phenomena and/or enhanced absorption phenomena which can occur at an interface between two materials may also be accounted for in the calculations using conventional techniques.

Exemplary System

Figure 23:
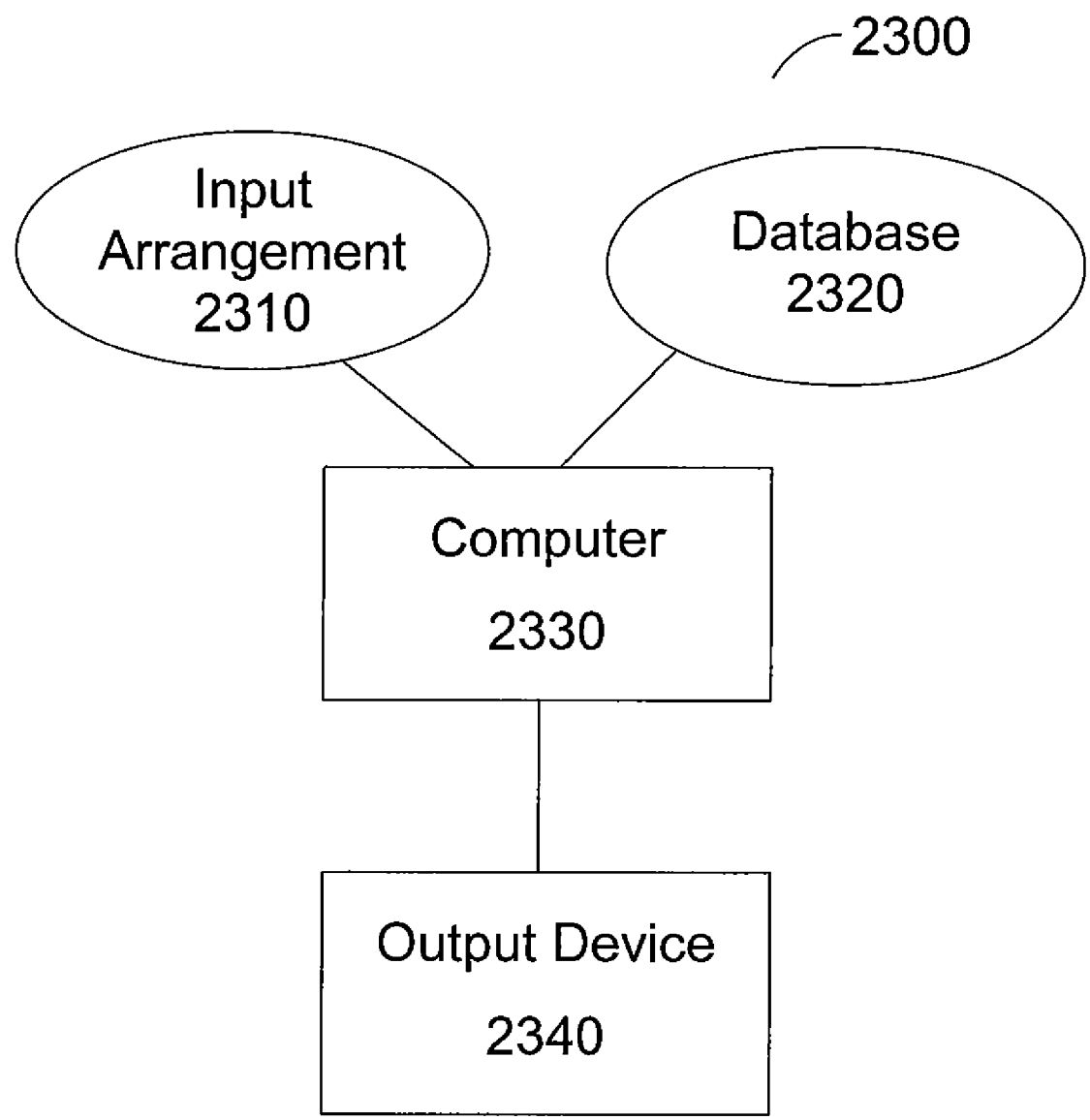
FIG. 23 is a schematic diagram of an exemplary system in accordance with certain exemplary embodiments of the present invention.

An exemplary embodiment of a system according to the present invention is shown in FIG. 23. For example, an input arrangement 2310 may be used to provide information to a computer 2330. Such information can include, e.g., parameters associated with a particular laser pulse or series of pulses, identification of a particular absorbing material, thickness of a sample of such material, etc. The input arrangement 2310 can include, but is not limited to, a keyboard, a mouse, or an arrangement capable of reading information from a computer-accessible medium such as, e.g., a hard drive, a CD-ROM, a DVD-ROM, a flash memory, a network connection, etc.

The exemplary system may further include a database 2320, which can also be configured to communicate with the computer 2330. The database 2320 can include, for example, numerical parameters that may be used to calculate an interaction between a nonlinear absorbing material and an coherent electromagnetic wave as described herein. The numerical parameters can include, e.g., incremental depth, radius and/or time intervals that may be used when performing calculations such as those described herein. The database 2320 can also include material parameters including, but not limited to, energy level diagram information, relaxation block parameters, absorption block parameters, etc. Some or all of such material parameters may optionally be provided to the computer 2330 using the input arrangement 2310.

The computer 2330 can include a processing arrangement, memory, etc. It may be configured, e.g., to determine an interaction between a nonlinear absorbing material and an coherent electromagnetic wave using exemplary techniques described herein and shown, e.g., in FIGS. 21 and 22a-22b. Information associated with such interaction may be communicated to an output device 2340. Such information can include, e.g., intensity or electric field distributions as a function of spatial position within the absorbing material and/or time, energy level populations, and/or contributions of individual levels to the total absorption. The output device 2340 may include, but is not limited to, a video monitor, a printer, a data storage medium, and the like. The computer 2330 can include a hard drive, CD ROM, RAM, and/or other storage devices or media which can include thereon software, which can be configured to execute the exemplary embodiments of the method of the present invention. Such storage devices or media may optionally contain the information associated with the database 2320.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced herein, to the extent applicable, are incorporated herein by reference in their entireties.

What is claimed is:

1. A method for analyzing interactions between electromagnetic radiation and an absorbing material having a plurality of energy states, comprising:
   obtaining on a computer processor first information related to the plurality of energy states associated with the absorbing material, the first information comprising a plurality of absorption and/or relaxation blocks where the absorption blocks characterize forward absorption and /or reverse absorption of electrons or excitons from one energy state to another energy state in the material and the relaxation blocks represent electron, exciton and/or phonon relaxations that occur between energy states in the material;
   obtaining on the computer processor second information related to electromagnetic radiation incident on the material; and
   generating on the computer processor a third information based on the first and second information, where the third information is a solution to a rate equation for a population density vector function for the energy states of the material and a propagation equation for an electric field in the material.

2. The method according to claim 1, wherein the electromagnetic radiation is an electromagnetic wave.

3. The method according to claim 1, wherein the electromagnetic radiation is an electric field.

4. The method according to claim 1, where the electromagnetic radiation comprises a laser pulse.

5. The method according to claim 1, where the electromagnetic radiation comprises a plurality of laser pulses, and where the second information comprises at least one of a duration, an intensity or an electric field associated with each of the pulses.

6. The method according to claim 1, where the electromagnetic radiation comprises a continuous electromagnetic wave.

7. The method of claim 1, wherein the electromagnetic radiation is coherent.

8. The method of claim 1, wherein the electromagnetic radiation is a fundamental mode of a cylindrically symmetric waveguide.

9. The method according to claim 1, wherein the first information comprises at least one of an energy level diagram or an energy level string.

10. The method according to claim 1, wherein the second information comprises at least one of a wavelength, a pulse width, an intensity or an electric field level.

11. A system for analyzing interactions between electromagnetic radiation and an absorbing material having a plurality of energy states comprising:
a non-transitory computer-accessible medium which includes thereon a set of instructions, wherein the set of instructions are configured to program a processing arrangement to:
receive first information related to the plurality of energy states associated with the absorbing material, the first information comprising a plurality of absorption and/or relaxation blocks where the absorption blocks characterize forward absorption and /or reverse absorption of electrons or excitons from one energy state to another energy state in the material and the relaxation blocks represent electron, exciton and/or phonon relaxations that occur between energy states in the material;
receive second information related to electromagnetic radiation incident on the material; and
generate on the processing arrangement third information based on the first and second information, where the third information is a solution to a rate equation for a population density vector function for the energy states of the material and a propagation equation for an electric field in the material.

12. A software arrangement embedded in a suitable non-transitory recording medium for analyzing interactions between electromagnetic radiation and an absorbing material having a plurality of energy states, comprising:
a first set of instructions which, when executed by a processing arrangement, is capable of receiving first information related to the plurality of energy states associated with the absorbing material the first information comprising a plurality of absorption and/or relaxation blocks where the absorption blocks characterize forward absorption and /or reverse absorption of electrons or excitons from one energy state to another energy state in the material and the relaxation blocks represent electron, exciton and/or phonon relaxations that occur between energy states in the material;
a second set of instructions which, when executed by the processing arrangement, is capable of receiving second information related to electromagnetic radiation incident on the material; and
a third set of instructions which, when executed by the processing arrangement, is capable of generating a third information based on the first and second information, where the third information is a solution to a rate equation for a population density vector function for the energy states of the material and a propagation equation for an electric field in the material.

13. The method of claim 1 wherein the rate and propagation equations are coupled and solved iteratively.

14. The method of claim 1 wherein the absorption blocks and/or relaxation blocks are used to populate matrices in the rate equation.

15. The method of claim 1 wherein the absorption blocks and/or the relaxation blocks are used to determine an electronic population for at least one of the plurality of energy levels or to determine a transmission or absorption of electromagnetic radiation in the material.

16. A method for characterizing a material having a plurality of energy states using a rate equation for a population density vector function comprising:
forming in a computer processor a plurality of absorption blocks and/or relaxation blocks where the absorption blocks characterize forward absorption and/or reverse absorption of electrons or excitons from one energy state to another energy state in the material and the relaxation blocks represent electron, exciton and/or phonon relaxations that occur between energy states in the material;
populating in the computer processor matrices of the rate equation with the absorption and/or relaxation blocks; and
solving the rate equation using the computer processor.

17. The method of claim 16 wherein the rate equation is solved iteratively using a Taylor series expansion.

18. The method of claim 17 wherein the Taylor series expansion is a second-order Taylor series expansion.

19. A method for analyzing an interaction between a beam of electromagnetic radiation and a material having a plurality of energy states, said method using a rate equation for a population density vector function for the material and a propagation equation for an electric field associated with the beam of electromagnetic radiation incident on the material, said method comprising:
forming in a computer processor a plurality of absorption blocks and/or relaxation blocks where the absorption blocks characterize forward absorption and/or reverse absorption of electrons or excitons from one energy state to another energy state in the material and the relaxation blocks represent electron, exciton and/or phonon relaxations that occur between energy states in the material;
populating in the computer processor matrices of the rate equation and vectors of the propagation equation with the absorption and/or relaxation blocks: and
solving the rate and propagation equations using the computer processor.

20. The method of claim 19 wherein the rate and propagation equations are coupled and solved iteratively.

21. A method for analyzing an interaction between electromagnetic radiation and a material having a plurality of energy levels comprising:
forming on a computer a plurality of absorption blocks and/or relaxation blocks that describe optical transitions between the plurality of energy levels of the material wherein each of the absorption blocks and the relaxation blocks includes at least one numerical parameter, and
forming on the computer a general numerical model that allows for determining the interaction between the electromagnetic radiation and the material using the absorption blocks and/or the relaxation blocks to determine an electronic population for at least one of the plurality of energy levels or to determine a transmission or absorption of the electromagnetic radiation in the material.

* * * * *